US007615651B2

(12) United States Patent
Ruggeri et al.

(10) Patent No.: US 7,615,651 B2
(45) Date of Patent: Nov. 10, 2009

(54) DIARYL, DIPYRIDINYL AND ARYL-PYRIDINYL DERIVATIVES AND USES THEREOF

(75) Inventors: Roger B. Ruggeri, Waterford, CT (US); George T. Magnus-Aryitey, Ledyard, CT (US); Benjamin A. Thuma, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/938,821

(22) Filed: Nov. 13, 2007

(65) Prior Publication Data
US 2008/0167371 A1 Jul. 10, 2008

Related U.S. Application Data

(60) Provisional application No. 60/865,479, filed on Nov. 13, 2006.

(51) Int. Cl.
C07C 211/00 (2006.01)
(52) U.S. Cl. ...................... 549/426; 564/157
(58) Field of Classification Search ................ 549/426; 514/459, 620; 564/157
See application file for complete search history.

(56) References Cited

U.S. PATENT DOCUMENTS

| 5,177,067 A | 1/1993 | Guerry et al. | 514/183 |
|---|---|---|---|
| 5,239,084 A | 8/1993 | Guerry et al. | 548/578 |
| 5,348,968 A | 9/1994 | Lavielle et al. | 514/380 |
| 5,637,771 A | 6/1997 | Aebi et al. | 564/337 |
| 6,020,357 A | 2/2000 | Pinto et al. | 514/406 |
| 6,060,491 A | 5/2000 | Pruitt et al. | 514/355 |
| 6,187,797 B1 | 2/2001 | Pruitt et al. | 514/380 |
| 6,329,527 B1 | 12/2001 | Zhou et al. | 548/241 |
| 6,339,099 B1 | 1/2002 | Lam et al. | 514/352 |
| 6,376,515 B2 | 4/2002 | Zhu et al. | 378/378 |
| 6,399,627 B1 | 6/2002 | Song et al. | 514/252.12 |
| 6,407,256 B1 | 6/2002 | Pinto et al. | 514/406 |
| 6,413,980 B1 | 7/2002 | Fevig et al. | 514/300 |
| 6,599,926 B2 | 7/2003 | Pinto et al. | 514/370.1 |
| 6,620,811 B2 | 9/2003 | Flohr et al. | 514/233.8 |
| 6,632,815 B2 | 10/2003 | Zhu et al. | 514/402 |
| 6,686,368 B1 | 2/2004 | Zhu et al. | 546/275.4 |
| 6,720,317 B1 | 4/2004 | Zhu et al. | 514/217.09 |
| 6,794,412 B1 | 9/2004 | Wong et al. | 514/309 |
| 6,800,651 B2 | 10/2004 | Coleman et al. | 514/357 |
| 6,835,739 B2 | 12/2004 | Zhu et al. | 514/352 |
| 6,844,367 B1 | 1/2005 | Zhu et al. | 514/620 |
| 7,074,801 B1 | 7/2006 | Yoshida et al. | 514/266.23 |
| 7,285,565 B2 | 10/2007 | Zhu et al. | 514/352 |
| 2003/0065176 A1 | 4/2003 | Kang et al. | 549/6 |
| 2003/0073862 A1 | 4/2003 | Gustavsson et al. | 562/434 |
| 2003/0135055 A1 | 7/2003 | Dorsch et al. | 548/132 |
| 2003/0176465 A1 | 9/2003 | Mederski et al. | 546/330 |
| 2004/0006114 A1 | 1/2004 | Coleman et al. | 514/345 |
| 2004/0077628 A1 | 4/2004 | Ishihara et al. | 514/412 |
| 2004/0116399 A1 | 6/2004 | Zhu et al. | 514/183 |
| 2004/0132720 A1 | 7/2004 | Marshall et al. | 540/598 |
| 2005/0107436 A1 | 5/2005 | Xie et al. | 514/438 |
| 2005/0148633 A1 | 7/2005 | Xie et al. | 514/332 |
| 2005/0245543 A1 | 11/2005 | Howard et al. | 514/256 |
| 2007/0129389 A1 | 6/2007 | Bilbe | 514/275 |
| 2007/0259919 A1 | 11/2007 | Rheinheimer et al. | 514/334 |

FOREIGN PATENT DOCUMENTS

| AU | 780787 | 4/2005 |
|---|---|---|
| AU | 781880 | 6/2005 |
| EP | 1259485 | 11/2002 |
| GB | 2273930 | 7/1994 |
| GB | 2276161 | 9/1994 |
| GB | 2276163 | 9/1994 |
| WO | WO 9723212 | 7/1997 |
| WO | WO 9828269 | 7/1998 |
| WO | WO 9828282 | 7/1998 |
| WO | WO 9857934 | 12/1998 |
| WO | WO 9857937 | 12/1998 |
| WO | WO 9932454 | 7/1999 |
| WO | WO 2004011427 | 7/2003 |
| WO | WO 2005063690 | 7/2005 |

OTHER PUBLICATIONS

Chi, et al., Development and validation of a liquid chromatography-mass spectrometric method for the determination of DPC 423, an antithrombotic agent, in rat and dog plasma. *Journal of Chromatography, B*: Analytical Technologies in the Biomedical and Life Sciences (2003), vol. 783(1), pp. 163-172.

(Continued)

*Primary Examiner*—Daniel M Sullivan
*Assistant Examiner*—Chukwuma O Nwaonicha
(74) *Attorney, Agent, or Firm*—Gregg C. Benson; Lisa A. Samuels

(57) ABSTRACT

Compounds of Formula (I) that act as antagonists at the mu, kappa and/or delta opioid receptors and therefore useful in the treatment of diseases, conditions and/or disorders that benefit from such antagonism in animals are described herein.

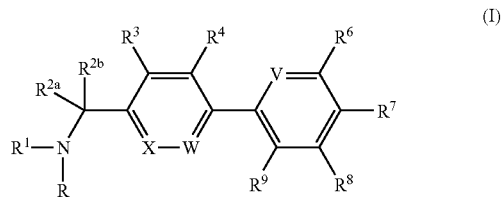

(I)

where R, $R^1$, $R^{2a}$, $R^{2b}$, $R^3$, $R^4$, V, $R^6$, $R^7$, $R^8$, $R^9$, W and X are described herein.

15 Claims, No Drawings

OTHER PUBLICATIONS

Denny, et al., Potential antitumor agents. 29. Quantitative structure-activity relationships for the antileukemic bisquaternary ammonium heterocycles. *Journal of Medicinal Chemistry* (1979), vol. 22(2), pp. 134-150.

Hadcock, et al., Role of opiates and their receptors in the regulation of food intake and body weight. *Drug Discovery Today: Therapeutic Strategies* (2005), vol. 2(2), pp. 171-175.

Leban, et al., Discovery of a novel series of DHODH inhibitors by a docking procedure and QSAR refinement, *Bioorganic & Medicinal Chemistry Letters 14*, (2004), pp. 55-58.

Tanaka, et al., Inhibitors of acyl -CoA:cholesterol O-acyltransferase (ACAT). Part 1: indentification and structure-activity relationships of a novel series of substituted N-alkyl-N-biphenylylmethyl-N'-arylureas. *Bioorganic & Medicinal Chemistry* (1998), vol. 6(1), pp. 15-30.

Zhang, et al., Design, Synthesis, and SAR of Monobenzamidines and Aminoisoquinolines as faxtor Xa Inhibitors, *Bioorganic & Medicinal Chemistry Letters 12*, (2002), pp. 1657-1661.

International Publication No. WO 2008/021849, Pub. Date Feb. 21, 2008, Cowan, et al.

Presentation by Roger Ruggeri entitled "Predicted Human Dose in Drug Design" given at the Gordon Research conference on Medicinal Chemistry on Sep. 9, 2008.

DIARYL, DIPYRIDINYL AND ARYL-PYRIDINYL DERIVATIVES AND USES THEREOF

FIELD OF THE INVENTION

The present invention relates to diaryl, dipyridinyl and aryl-pyridinyl derivatives and the uses thereof for treating diseases, conditions and/or disorders mediated by the opioid receptors. The compounds are particularly useful as mu, kappa and/or delta opioid receptor antagonists.

BACKGROUND

Obesity is a significant health problem due to its serious medical complications that include co-morbidities such as hypertension, insulin resistance, diabetes, coronary artery disease and heart failure (collectively referred to as Metabolic Syndrome). Obesity and its related co-morbidities continue to cause rising health issues in the developed world and are beginning to affect the developing world as well. The negative health consequences of obesity make it the second leading cause of preventable death in the United States and impart a significant economic and psychosocial effect on society. See, McGinnis M, Foege W H., "Actual Causes of Death in the United States," *JAMA,* 270, 2207-12 (1993). Clearly, there is a need to identify and develop new medications that treat and/or prevent obesity and its associated co-morbidities.

Although the clinical data using naltrexone have been inconsistent, there is considerable support in the literature implicating opioid receptors in the regulation of energy homeostasis, thus suggesting that antagonism of one or more of the opiate receptor subtypes can be a suitable target for the treatment of obesity. See, e.g., Hadcock, J. R., et al., "Role of opiates and their receptors in the regulation of food intake and body weight," *Drug Discovery Today: Therapeutic Strategies,* 2(2), 171-175 (2005). Although naltrexone is useful for the treatment of alcohol abuse and dependence, poor weight loss efficacy was observed in rodents and humans. It is speculated that this poor weight loss may be due to partial agonism at the kappa and delta opioid receptors.

Pan-selective opioid receptor antagonists (e.g., LY255582) have been shown to provide robust anorectic effects. See, e.g., Gackenheimer, S. L., et al., "Localization of opioid receptor antagonist [3H]-LY255582 binding sites in mouse brain: Comparison with the distribution of mu, delta and kappa binding sites," *Neuropeptide,* 39, 559-567 (2005): Shaw, W. N, et al., "The effect of the opioid antagonist LY255582 on body weight of the obese Zucker rat," *Int J Obes,* 15(6), 387-95 (1991): Shaw, W. N., "Long-term treatment of obese Zucker rats with LY255582 and other appetite suppressants," *Pharmacol Biochem Behav,* 46(3), 653-9 (1993): and Levine, A. S., et al., "Central administration of the opioid antagonist, LY255582, decreases short- and long-term food intake in rats," *Brain Res,* 566(1-2), 193-7 (1991). Compounds that act as inverse agonists or antagonists at the mu, kappa and delta opioid receptors have also been reported. In particular, LY515300 (1-(3-cyclohexyl-3-hydroxypropyl)-3(R),4(R)-dimethyl-4-(3-hydroxyphenyl)piperidine) has been shown to have subnanomolar binding affinity for the mu and kappa opioid receptor subtypes, but has a lower affinity for the delta opioid receptor. See, e.g., Statnick, M. A., et al., "Na+-dependent high affinity binding of [3H]LY515300, a 3,4-dimethyl-4-(3-hydroxyphenyl)piperidine opioid receptor inverse agonist," *Eur J Pharm,* 482, 139-150 (2003): and Zimmerman, D. M., et al., "Structure-activity relations of trans-3,4-dimethyl-4-(3-hydroxyphenyl)piperidine antagonists for mu- and kappa-opioid receptor," *J Med Chem* 36(20), 2833-2841 (1993).

Although many opioid receptor antagonists are known, there remains a need to identify compounds having improved efficacy and therapeutic indices, in particular for the treatment of obesity and obesity-related co-morbidities.

SUMMARY

The present invention provides compounds of Formula (I)

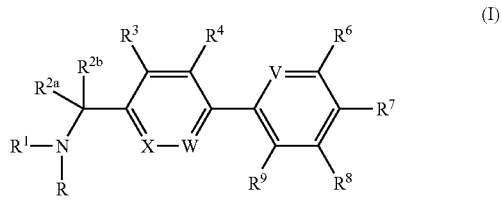

wherein R is hydrogen or R taken together with $R^1$ and the nitrogen to which they are attached form a pyrrolidine optionally fused to a benzene ring or a piperidine ring optionally fused to a benzene ring, where the pyrrolidine, the pyrrolidine fused to a benzene ring, the piperidine, and the piperidine fused to a benzene ring are optionally substituted with 1 to 3 substituents each independently selected from methyl, halo, —OH, or —C(O)—O($C_1$-$C_4$)alkyl;

$R^1$ is
  (a) ($C_3$-$C_8$)alkyl,
  (b) ($C_3$-$C_8$)alkenyl,
  (c) partially or fully saturated ($C_6$-$C_6$)carbocycle optionally fused to a benzene ring,
  (d) partially or fully saturated 5- to 6-membered heterocycle containing 1 to 2 heteroatoms independently selected from O, S or N optionally fused to a benzene ring, or
  (e) ($C_1$-$C_3$)alkyl substituted with a chemical moiety selected from the group consisting of
    (i) partially or fully saturated ($C_3$-$C_6$)carbocycle optionally fused to a benzene ring,
    (ii) ($C_1$-$C_4$)alkoxy,
    (iii) partially or fully saturated 5- to 6-membered heterocycle containing 1 to 2 heteroatoms independently selected from O, S or N optionally fused to a benzene ring,
    (iv) 5- to 6-membered heteroaryl containing 1 to 3 heteroatoms independently selected from O, S or N optionally fused to a benzene ring,
    (v) phenyl optionally fused to a 5- to 6-membered heterocycle containing 1 to 2 heteroatoms independently selected from O, S or N,
    (vi) naphthyl,
    (vii) phenoxy, and
    (viii) 2-oxo-2,3-dihydrobenzimidazolyl, where the substituents (a) through (e) and the chemical moieties (i) through (viii) are each optionally substituted with one to three substituents independently selected from hydroxyl, halo, methyl, or HO—($C_1$-$C_3$)alkyl;

$R^{2a}$ and $R^{2b}$ are each hydrogen;

$R^3$ is hydrogen, halo, ($C_1$-$C_3$)alkyl, hydroxyl, ($C_1$-$C_3$) alkoxy, or benzyloxy;

$R^4$ is hydrogen, halo, ($C_1$-$C_3$)alkyl, hydroxyl, ($C_1$-$C_3$) alkoxy, or fluoro-substituted methyl;

V is nitrogen or C—$R^5$, where $R^5$ is hydrogen, halo, ($C_1$-$C_3$)alkyl, hydroxyl, ($C_1$-$C_3$)alkoxy, fluoro-substituted methyl, or benzyloxy;

$R^6$ is hydrogen, ($C_1$-$C_3$)alkyl, hydroxyl, ($C_1$-$C_3$)alkoxy, or halo;

$R^7$ is —C(O)$NH_2$, —$NHSO_2$($C_1$-$C_4$)alkyl, or 1H-1,2,4-triazol-5-yl, and $R^8$ is hydrogen, fluoro, or —OH; or $R^7$ is hydrogen, fluoro, or —OH, and $R^8$ is —C(O)$NH_2$, —$NHSO_2$($C_1$-$C_4$)alkyl, or 1H-1,2,4-triazol-5-yl;

$R^9$ is hydrogen, hydroxyl, ($C_1$-$C_3$)alkyl, fluoro-substituted methyl, ($C_1$-$C_3$)alkoxy, or halo; and W is C—$R^{10}$ and X is nitrogen, or W is nitrogen and X is C—$R^{11}$, or W is C—$R^{10}$ and X is C—$R^{11}$, where $R^{10}$ is hydrogen, ($C_1$-$C_3$)alkyl, hydroxyl, ($C_1$-$C_3$)alkoxy, fluoro-substituted methyl, cyano, or halo; and $R^{11}$ is hydrogen, ($C_1$-$C_3$)alkyl, hydroxyl, ($C_1$-$C_3$)alkoxy, or halo;

a pharmaceutically acceptable salt thereof or a solvate or hydrate of said compound or said salt.

In a preferred embodiment,

R is hydrogen;

$R^1$ is (a) a non-linear ($C_4$-$C_6$) alkyl, (b) fully saturated ($C_5$-$C_6$)carbocycle fused to a benzene ring, (c) fully saturated 5- to 6-membered heterocycle containing 1 to 2 heteroatoms independently selected from O, S or N fused to a benzene ring, or (d) ($C_1$-$C_3$)alkyl substituted with a chemical moiety selected from the group consisting of (i) fully saturated ($C_3$-$C_6$)carbocycle optionally fused to a benzene ring, (ii) ($C_1$-$C_4$)alkoxy, (iii) fully saturated 5- to 6-membered heterocycle containing 1 to 2 heteroatoms independently selected from O, S or N optionally fused to a benzene ring, (iv) 5- to 6-membered heteroaryl containing 1 to 3 heteroatoms independently selected from O, S or N optionally fused to a benzene ring, (v) phenyl optionally fused to a 5- to 6-membered heterocycle containing 1 to 2 heteroatoms independently selected from O, S or N, (vi) naphthyl, and (vii) phenoxy, where the substituents (a) through (d) and the moieties (i) through (vii) are each optionally substituted with one to three substituents independently selected from —OH, chloro, fluoro, or methyl;

$R^{2a}$ and $R^{2b}$ are each hydrogen;

$R^3$ is hydrogen, chloro, fluoro, hydroxyl, or methoxy;

$R^4$ is hydrogen, chloro, fluoro, methyl, or fluoro-substituted methyl;

V is nitrogen or C—$R^5$, where $R^5$ is hydrogen, methyl, ethyl, fluoro-substituted methyl, chloro, fluoro, or methoxy;

$R^6$ is hydrogen or fluoro, $R^9$ is hydrogen, ($C_1$-$C_3$)alkyl, fluoro-substituted methyl, chloro, or fluoro; and W is C—$R^{10}$ and X is nitrogen, or W is nitrogen and X is C—$R^{11}$, or W is C—$R^{10}$ and X is C—$R^{11}$, where $R^{10}$ is hydrogen, methyl, fluoro-substituted methyl, cyano, chloro, or fluoro, and $R^{11}$ is hydrogen, methyl, methoxy, chloro, or fluoro;

a pharmaceutically acceptable salt thereof or a solvate or hydrate of said compound or said salt.

More preferably, $R^1$ is a non-linear ($C_4$-$C_6$) alkyl, a fully saturated ($C_5$-$C_6$)carbocycle fused to a benzene ring, or a ($C_1$-$C_3$)alkyl substituted with a chemical moiety selected from the group consisting of (i) fully saturated ($C_3$-$C_6$)carbocycle optionally fused to a benzene ring, (ii) ($C_1$-$C_4$)alkoxy, (iii) fully saturated 5- to 6-membered heterocycle containing an oxygen optionally fused to a benzene ring, (iv) phenyl optionally substituted with a chloro or fluoro, and (v) phenoxy;

a pharmaceutically acceptable salt thereof or a solvate or hydrate of said compound or said salt.

Preferred compounds include 3',5'-Difluoro-2-methyl-4'-[(3-methyl-butylamino)-methyl]-biphenyl-4-carboxylic acid amide; 2,2'-Dimethyl-4'-[(3-methyl-butylamino)-methyl]-biphenyl-4-carboxylic acid amide; and 3'-Chloro-2-methyl-4'-[(3-methyl-butylamino)-methyl]-biphenyl-4-carboxylic acid amide hydrochloride; a pharmaceutically acceptable salt thereof or a solvate or hydrate of said compound or said salt. A more preferred compound is 3',5'-Difluoro-2-methyl-4'-[(3-methyl-butylamino)-methyl]-biphenyl-4-carboxylic acid amide; a hydrochloride salt thereof or a hydrate of said hydrochloride salt. The most preferred compound is 3',5'-Difluoro-2-methyl-4'-[(3-methyl-butylamino)-methyl]-biphenyl-4-carboxylic acid amide hydrochloride monohydrate.

Some of the compounds described herein may contain at least one chiral center; consequently, those skilled in the art will appreciate that all stereoisomers (e.g., enantiomers and diastereomers) of the compounds illustrated or otherwise described herein are within the scope of the present invention. In addition, tautomeric forms of the compounds are also within the scope of the present invention.

Compounds of Formula (I) have been found to act as antagonist at the mu, kappa and/or delta opioid receptors and therefore may be used in the treatment of diseases, conditions and/or disorders that benefit from such antagonism (e.g., diseases related to obesity and obesity-related co-morbidities). In particular, the compounds of Formula (I) provide combined mu and kappa receptor antagonism resulting in improved food intake, efficacy, and potency. Consequently, another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents (described herein below) and most preferred are CB-1 antagonists (described herein below).

In yet another embodiment of the present invention, methods for treating a disease, condition and/or disorder that are mediated by antagonizing the mu, kappa and/or delta opioid receptors in animals are provided which comprise the step of administering to an animal (preferably, a human) in need of such treatment a therapeutically effective amount of a compound of the present invention (or a pharmaceutical composition thereof), e.g., to reduce body weight, lower blood pressure, and/or lower insulin resistance.

Diseases, conditions, and/or disorders mediated by antagonizing the mu, kappa and/or delta opioid receptors include obesity (including weight control or weight maintenance), and obesity-related co-morbidities (e.g., dyslipidemia, hypertension, insulin resistance, diabetes, coronary artery disease and heart failure).

Compounds of the present invention may be administered in combination with other pharmaceutical agents. Preferred pharmaceutical agents include anti-obesity agents, such as apo-B/MTP Inhibitors, Cannabinold-1 (CB-1) antagonists (or Inverse agonists), 11β-hydroxy steroid dehydrogenase-1 (11β-HSD type 1) inhibitors, peptide $YY_{3-36}$ (including analogs thereof, MCR-4 agonists, CCK-A agonists, monoamine reuptake inhibitors, sympathomimetic agents, $β_3$ adrenergic agonists, dopamine agonists, melanocyte-stimulating hormone analogs, 5-HT2c agonists, melanin concentrating hormone antagonists, leptin (including analogs thereof, leptin agonists, galanin antagonists, lipase inhibitors, bombesin agonists, neuropeptide-Y antagonists (e.g., NPY Y5 antagonists such as those described herein below), thyromimetic agents, dehydroepiandrosterone (including analogs thereof), glucocorticoid antagonists, orexin antagonists, glucagon-like peptide-1 agonists, ciliary neurotrophic factors, human agouti-related protein antagonists, ghrelin antagonists, histamine 3 antagonists or inverse agonists, and neuromedin U agonists, and the like.

The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DETAILED DESCRIPTION

Definitions

As used herein, the term "alkyl" refers to a hydrocarbon radical of the general formula $C_nH_{2n+1}$. The alkane radical may be straight or branched. For example, the term "$(C_1-C_6)$ alkyl" refers to a monovalent, straight, or branched aliphatic group containing 1 to 6 carbon atoms (e.g., methyl, ethyl, n-propyl, i-propyl, n-butyl, 1-butyl, s-butyl, t-butyl, n-pentyl, 1-methylbutyl, 2-methylbutyl, 3-methylbutyl, neopentyl, 1,1-dimethylpropyl, hexyl, 2-methylpentyl, and the like). Similarly, the alkyl portion (i.e., alkyl moiety) of an alkoxy group has the same definition as above. When indicated as being "optionally substituted", the alkane radical or alkyl moiety may be unsubstituted or substituted. Unless specified otherwise, a substituted alkyl is generally substituted with one to three substituents except in the case of halogen substituents such as perchloro or perfluoroalkyls. "Halo-substituted alkyl" refers to an alkyl group substituted with one or more halogen atoms (e.g., fluoromethyl, difluoromethyl, trifluoromethyl, perfluoroethyl, and the like).

The term "non-linear alkyl" refers to alkyl radicals that are primary alkyl radicals having at least one side chain, secondary alkyl radicals, and/or tertiary alkyl radicals. Suitable non-linear alkyl groups include, for example, t-butyl, 2-methylpropyl, 2,2-dimethylpropyl, 1,1-dimethylpropyl, 3,3-dimethylbutyl, 2-ethylbutyl, 3-methylbutyl, 2-ethylpentyl, 3-ethylpentyl, 2-ethylhexyl, 3-ethylhexyl, 2,4-dimethyl-3-pentyl, and the like.

The terms "carbocycle" refers to nonaromatic rings that are either partially or fully saturated (i.e., hydrogenated) and may exist as a single ring, bicyclic ring or a spiral ring. Fully saturated carbocyclic rings are also referred to as "cycloalkyl." Unless specified otherwise, the carbocyclic ring is generally a 3- to 8-membered ring. For example, partially or fully saturated carbocyclic rings include groups such as cyclopropyl, cyclopropenyl, cyclobutyl, cyclobutenyl, cyclopentyl, cyclopentenyl, cyclopentadienyl, cyclohexyl, cyclohexenyl, cyclohexadienyl, norbornyl (bicyclo[2.2.1]heptyl), norbornenyl, bicyclo[2.2.2]octyl, spiro[2.5]octanyl and the like. When designated as being "optionally substituted", the partially saturated or fully saturated carbocyclic group may be unsubstituted or substituted (typically, one to three substituents). When fused to a benzene ring, substituents may be attached to either the carbocyclic group or the fused benzene ring. A carbocyclic ring fused to a benzene ring includes groups such as 2,3-dihydroindenyl (or indanyl) and indenyl. The carbocyclic group may be attached to the chemical entity or moiety by any one of the carbon atoms within the carbocyclic or fused ring system.

The term "heterocyclic ring" refers to nonaromatic rings that are either partially or fully saturated (i.e., hydrogenated) and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, oxetanyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be substituted or unsubstituted (typically, one to three substituents). When fused to a benzene ring, substituents may be attached to either the heterocyclic group or the fused benzene ring.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted (typically, one to three substituents). The aryl group may be attached to the chemical entity or moiety by any one of the carbon atoms within the aromatic ring system.

The term "heteroaryl" or "heteroaromatic ring" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl group may be unsubstituted or substituted (typically, one to three substituents). When fused to a benzene ring, substituents may be attached to either the heteroaryl group or the fused benzene ring. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl).

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of on a hydroxy group that blocks or protects the hydroxy functionality. Suitable protecting groups include acetyl and tert-butyldimethylsilyl. A "carboxy-protecting group" refers to a substituent of the carboxy group that blocks or protects the carboxy functionality. Common carboxy-protecting groups include lower alkyls (e.g., methyl, ethyl, t-butyl), benzyl, allyl, —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991. Theodora W. Greene, Peter G. M. Wuts, Protective Groups in Organic Synthesis (Third Edition) Copyright © 1999 by John Wiley & Sons, Inc.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulating opioid receptor activity" or "Opioid-mediated" refers to the activation or deactivation of the mu, kappa and/or delta opioid receptors.

The term "compound(s) of the present invention" (unless specifically identified otherwise) refers to the compound of Formula (I) and pharmaceutically acceptable salts thereof. Included within the definition of compound(s) of the present invention are all stereoisomers (including diastereomers and enantiomers), tautomers, isotopically labeled compounds and inherently formed moieties (e.g., solvates and/or hydrates) and are therefore considered equivalents of the compounds of the present invention.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991. Theodora W. Greene, Peter G. M. Wuts, Protective Groups in Organic Synthesis (Third Edition) Copyright © 1999 by John Wiley & Sons, Inc.

Scheme I outlines the general procedures one could use to provide compounds of the present invention where $R^7$ is —C(O)NH$_2$ (or $R^8$ is —C(O)NH$_2$ using the appropriate starting material (sm-4) described below).

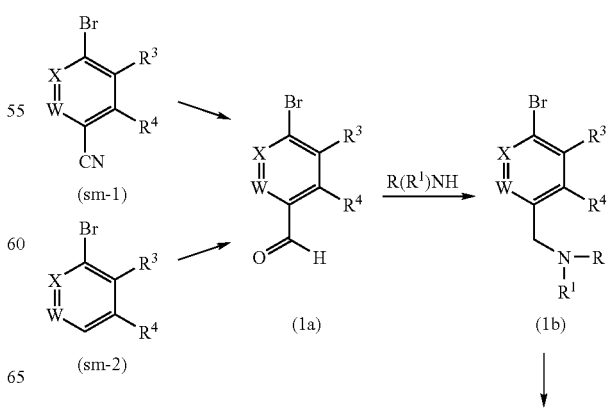

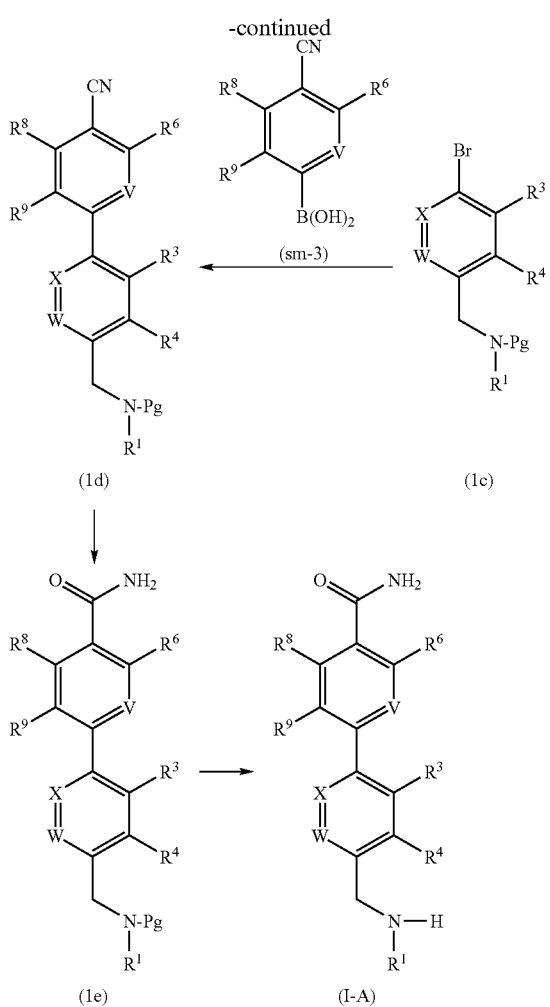

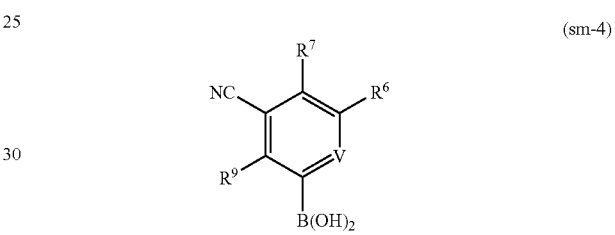

The reaction is then quenched with a strong base and/or acid (e.g., potassium hydroxide or hydrochloric acid).

An amino protecting group is added to the amino compound (1b) to form (1c) prior to condensing with the desired para-substituted cyano aryl or heteroaryl boronic acid compound (sm-3) to form intermediate (1d). A preferred protecting group is the t-butoxycarbonyl (BOC) group. Intermediate (1d) may be prepared by condensing the desired para-substituted cyano boronic acid (sm-3) with the amino-protected intermediate (1c) in the presence of palladium tetrakis(triphenylphosphine) and bicarbonate followed by heating to elevated temperatures (about 95° C.). In the preparation of compounds of Formula (I) where $R^8$ is $C(O)NH_2$, the desired meta-substituted cyano boronic acid (sm-4) is used in place of the para-substituted cyano boronic acid (sm-3). For those compounds where R is other than hydrogen, an amino-protecting group is not necessary and the boronic acid compounds (sm-3 and sm-4) may be coupled directly with intermediate (1b) to produce the compounds of the present invention where R is other than hydrogen.

The cyano group is then converted to the amido group using standard procedures well-known to those of skill in the art. For example, intermediate (1d) may be treated with hydrogen peroxide in water in the presence of potassium carbonate. The protecting group is removed from intermediate (1e) using the appropriate conditions to remove the particular protecting group used. For example, the BOC group may be removed by treating with 4.0 M hydrogen chloride in dioxane to produce a compound of the present invention (I-A).

Scheme II below provides an alternative synthesis for intermediate (1b) used in Scheme I above.

The intermediate aldehyde (1a) may be prepared from the corresponding nitrile compound (sm-1) using standard reduction procedures well-known to those of skill in the art. For example, the nitrile compound (sm-1) may be treated with diisobutylaluminum hydride at a cooled temperature (about 60° C.) in a non-protic solvent (e.g., toluene and dichloromethane). The reaction is then worked up with a strong acid (e.g., hydrochloric acid). Alternatively, aldehyde (1a) may be prepared from the aryl or heteroaryl compound (sm-2) by treating with lithium diisopropylamide at cooled temperature (about −78° C.) followed by formylation of the corresponding aryl anion with e.g., dimethylformamide. The reaction is worked up with an aqueous solution of a weak acid (e.g., acetic acid). Such aryl aldehydes may also be prepared by oxidation of the corresponding benzyl alcohol, oxidation of the corresponding aryl methyl group, oxidative cleavage of an arylvinyl species, hydrolysis of the corresponding acetal, or selective reduction of an aryl acid or aryl amide species (e.g., mono reduction of the N,O-dimethylhydroxylamine amide with a suitable hydride species). The desired amino compound ($R^1NH_2$) is added to the molecule to produce the amino compound (1b) via reductive amination procedures well-known to those of skill in the art. For example, the aldehyde (1a) in the presence of the desired amine compound or after the corresponding imine has been formed by condensation is treated with a borohydride (e.g., sodium triacetoxyborohydride, sodium cyanoborohydride or sodium borohydride).

Scheme II

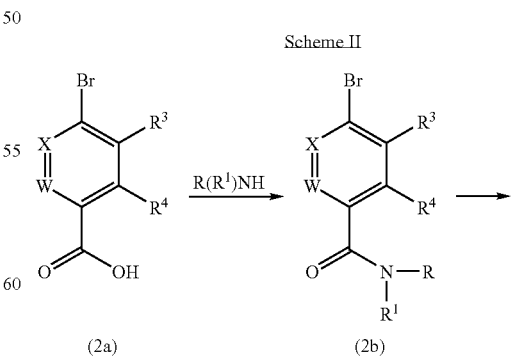

-continued

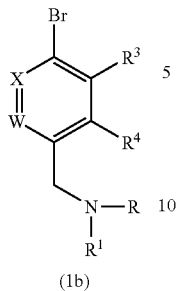

(1b)

The carboxylic acid derivative (2a) may be converted to the corresponding amide using procedures well-known to those of skill in the art. For example, amide (2b) may be formed by reacting the acid (2a) with the desired amine (R(R¹)NH) in the presence of a coupling reagent. Suitable coupling reagents include dicyclohexylcarbodiimide (DCCI), 1-hydroxybenzotriazole (HOBT), 6-chloro-1 hydroxybenzotriazole (Cl-HOBT), 1-ethyl-3-(3'-dimethylaminopropyl)carbodiimide (EDC), N-[(1H-benzotriazol-1-yl)(dimethylamino)methylene]-N-methylmethanaminium hexafluorophosphate N-oxide (HBTU), N-[(dimethylamino)-1H-1,2,3-triazolo[4,5b]pyridine-1-ylmethylene]-N-methylmethanaminium hexafluorophosphate (HATU), and benzotriazol-1-yl-N-oxytris(pyrrolidino)phosphonium hexafluorophosphate (PyBOP). The amide group may then be reduced to the corresponding alkyl amine using conventional reduction procedures. For example, the amide (2b) may be treated with lithium aluminum hydride, diisobutylaluminum hydride, borane or tetrabutylammonium borohydride in an inert solvent to produce the amino compound (1b).

Scheme III below provides an alternative synthesis for intermediate (1d) used in Scheme I above.

Scheme III

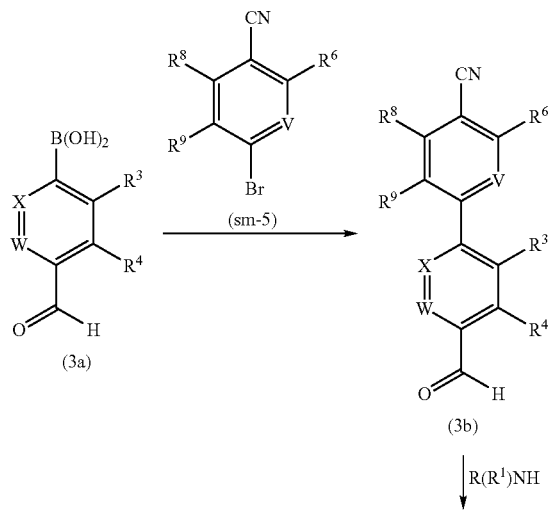

In Scheme III above, the aryl or heteroaryl compounds (3a) and (sm-5) are coupled prior to the reductive amination to produce intermediate (3c). For example, intermediate (3b) may be prepared by condensing the desired para-substituted cyano bromide compound (sm-5) with the desired boronic aldehyde (3a) in the presence of palladium tetrakis(triphenylphosphine) and bicarbonate followed by heating to elevated temperatures (about 95° C.). In the preparation of compounds of Formula (I) where $R^8$ is —C(O)NH$_2$, the desired meta-substituted cyano bromide compound (sm-6) is used in place of the para-substituted cyano bromide compound (sm-5).

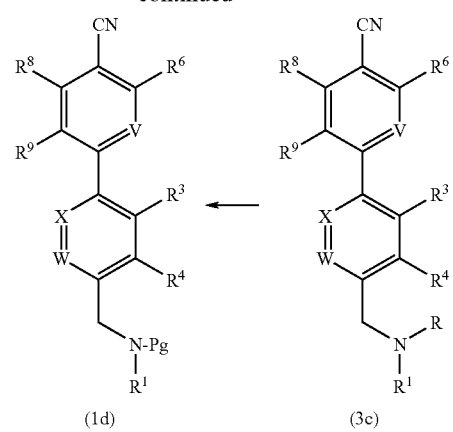

(sm-6)

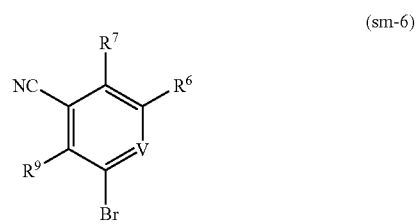

Intermediate (3a) is then prepared by reductive amination with the desired amino compound (R(R¹)NH) followed by the introduction of an appropriate amino-protecting group (if necessary, i.e., R=H) to produce intermediate (1d). Similar to the procedures described above in Scheme I, the amino intermediate (3b) may be produced via reductive amination of aldehyde (3a) with the desired amine compound in the presence a borohydride (e.g., sodium triacetoxyborohydride or sodium borohydride). The reaction is then quenched with a strong base and/or acid (e.g., potassium hydroxide or hydrochloric acid). When R is other than hydrogen, the cyano group of intermediate (3b) may be hydrolyzed to the corresponding amide group to produce a compound of the present invention.

Scheme IV below outlines an alternative procedure for preparing intermediate (3b).

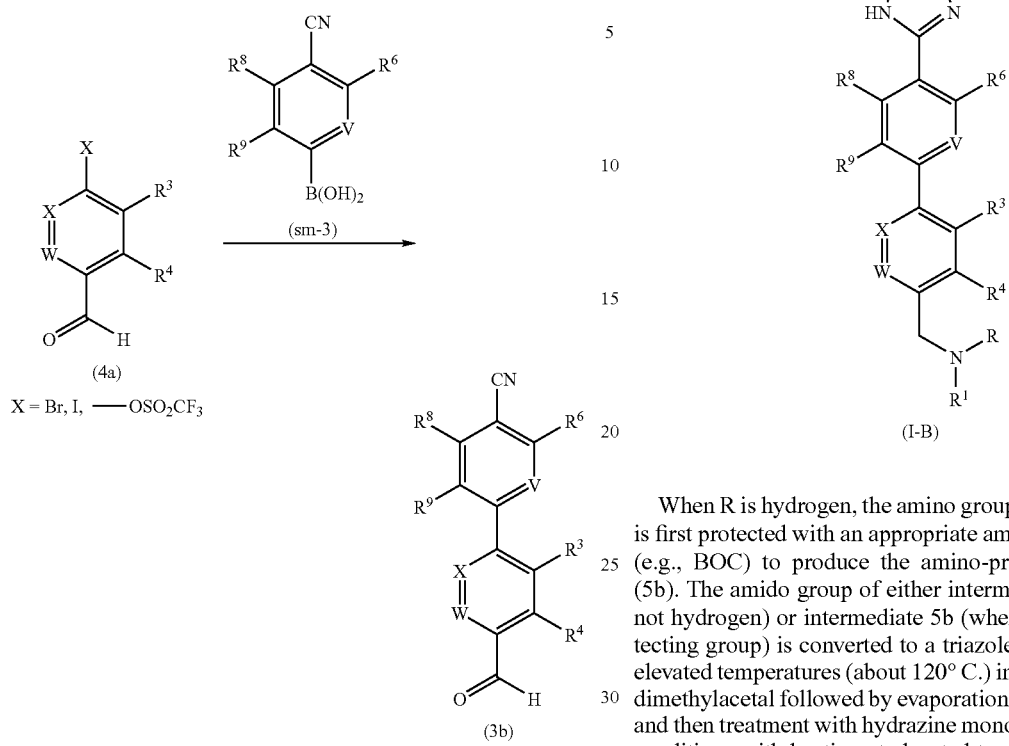

Intermediate (3b) may also be produced by coupling the aldehyde (4a) with the boronic acid (sm-3) in the presence of palladium tetrakis(triphenylphosphine) and bicarbonate followed by heating to elevated temperatures (about 95° C.). In the preparation of compounds of Formula (I) where $R^8$ is —C(O)NH$_2$, the desired meta-substituted cyano boronic acid compound (sm-4) is used in place of the para-substituted cyano boronic acid compound (sm-3).

Scheme V outlines the general procedures one could use to provide compounds of Formula (I) where $R^7$ is 1H-1,2,4-triazol-5-yl.

When R is hydrogen, the amino group of intermediate (5a) is first protected with an appropriate amino-protecting group (e.g., BOC) to produce the amino-protected intermediate (5b). The amido group of either intermediate 5a (when R is not hydrogen) or intermediate 5b (when R is an amino protecting group) is converted to a triazole group by heating at elevated temperatures (about 120° C.) in dimethylformamide dimethylacetal followed by evaporation of the excess reagent and then treatment with hydrazine monohydrate under acidic conditions with heating at elevated temperatures (about 90° C.). Deprotection of the amine protecting group as described above provides the product 1-B from intermediate 5b.

Compound of the present invention where $R^8$ is 1H-1,2,4-triazol-5-yl may be prepared using the same general procedures described above for preparing (1-B) except starting with the appropriate starting materials (sm-4 or sm-6) to produce the corresponding meta intermediate of the para intermediates 5a or 5b above.

Scheme VI below outlines the procedures one could use to produce compounds of Formula (I) where $R^7$ is —NHSO$_2$(C$_1$-C$_4$)alkyl.

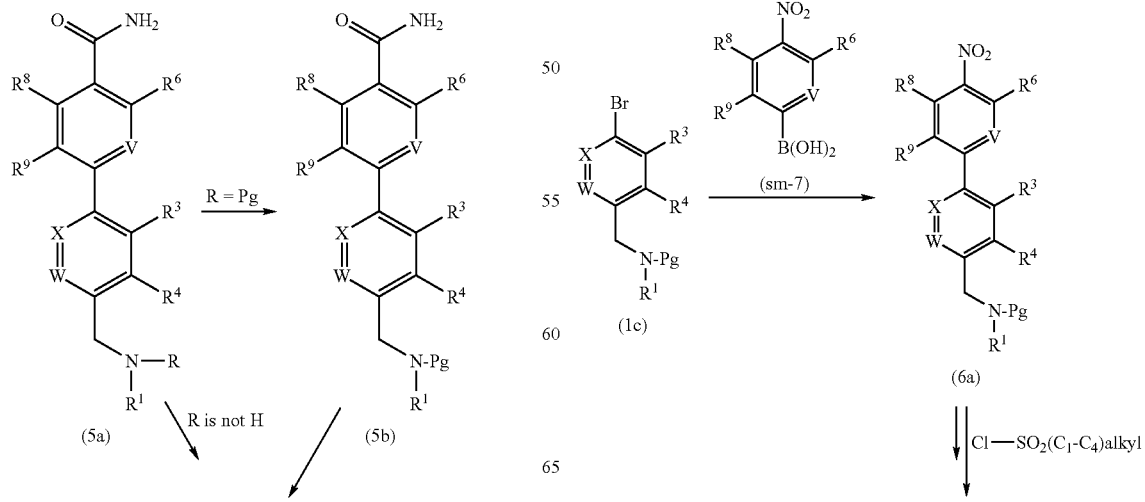

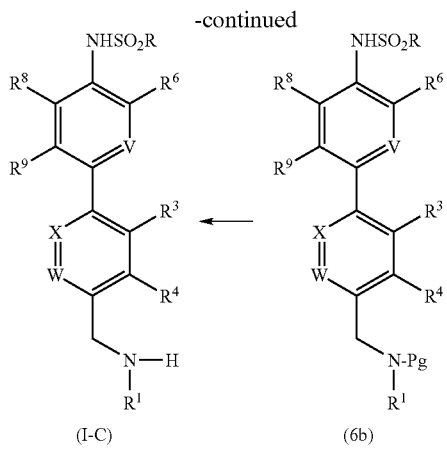

(I-C)    (6b)

The nitro intermediate (6a) is formed by coupling intermediate (1c) with the para-substituted nitro boronic acid compound (sm-7) in the presence of a coupling agent (e.g., tetrakis(triphenylphosphine) palladium) under basic conditions (e.g., sodium carbonate) followed by heating at elevated temperatures (about 80° C.). The nitro group is then reduced to the corresponding amino group using standard reduction procedures well-known to those of skill in the art. For example, the nitro group may be reduced via hydrogenation in the presence of Pd on carbon catalyst. The amino group is then condensed with the desired sulfonyl chloride (($C_1$-$C_4$)alkyl-$SO_2$—Cl) to produce intermediate (6b). The amino-protecting group is then removed using the appropriate conditions for the particular amino-protecting group used. For example, the BOC group may be removed by treating with 4.0 M hydrogen chloride in dioxane to produce a compound of the present invention (I-C).

Compounds of the present invention where $R^8$ is —$NHSO_2$($C_1$-$C_4$)alkyl may be prepared using the same basic procedures described above except using the corresponding meta-substituted nitro boronic acid compound (sm-8) in place of the para-substituted nitro boronic acid compound (sm-7).

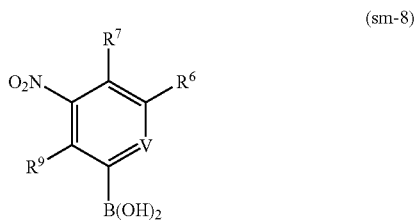

(sm-8)

For compounds where R is other than hydrogen, then the use of an amino-protecting group is not necessary. The same procedures described above may be used for the coupling reaction with the starting materials (sm-7 or sm-8), the reduction of the nitro group and condensation with the desired sulfonyl chloride to produce the desired compound.

The compounds of the present invention may be isolated and used per se or in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds and salts of the present invention may inherently form solvates with pharmaceutically acceptable solvents (including water) and R is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, 18O, $^{31}$P, $^{32}$P, $^{35}$, S$^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with more stable isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and/or disorders modulated by the mu, kappa and/or delta opioid receptors; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides methods of treating diseases, conditions and/or disorders modulated by the opioid receptor(s) in an animal that include administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from antagonizing the mu, kappa and/or delta opioid receptors (in particular, the mu and kappa opioid receptors).

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared (kg/m$^2$). Overweight is typically defined as a BMI of 2529.9 kg/m$^2$, and obesity is typically defined as a BMI of 30 kg/m$^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant (p<0.05) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant (p<0.05) reduction in glucose serum levels.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents.

Suitable anti-obesity agents include cannabinoid-1 (CB-1) antagonists (such as rimonabant), 11β-hydroxy steroid dehydrogenase-1 (11β-HSD type 1) inhibitors, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPYY5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB-secretion inhibitors (e.g., gut-selective MTP inhibitors, such as dirlotapide) and the like.

Preferred anti-obesity agents for use in the combination aspects of the present invention include CB-1 antagonists, gut-selective MTP inhibitors, CCKa agonists, 5HT2c agonists, $PYY_{1-36}$ (more preferably $PYY_{3-36}$, including analogs, such as pegylated $PYY_{3-36}$), NPYY5 antagonists, bromocriptine, orlistat, and sibutramine. Preferably, compounds of the present invention and combination therapies are administered in conjunction with exercise and a sensible diet.

Sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and $PYY_{3-36}$ (including analogs thereof) can be prepared as described in US Publication No. 2002/0141985 and WO 03/027637; and 5HT2c agonists can be prepared as described in U.S. Pat. No. 6,825,198.

Preferred CB-1 antagonists include: rimonabant (SR141716A also known under the tradename Acomplia™) is available from Sanofi-Synthelabo or can be prepared as described in U.S. Pat. No. 5,624,941; N-(piperidin-1-yl)-1-(2,4-dichlorophenyl)-5-(4-iodophenyl)-4-methyl-1H-pyrazole-3-carboxamide (AM251) is available from Tocris™, Ellisville, Mo.; [5-(4-bromophenyl)-1-(2,4-dichloro-phenyl)-4-ethyl-N-(1-piperidinyl)-1H-pyrazole-3-carboxamide] (SR147778) which can be prepared as described in U.S. Pat. No. 6,645,985; N-(piperidin-1-yl)-4,5-diphenyl-1-methylimidazole-2-carboxamide, N-(piperidin-1-yl)-4-(2,4-dichlorophenyl)-5-(4-chlorophenyl)-1-methylimidazole-2-carboxamide, N-(piperidin-1-yl)-4,5-di-(4-methylphenyl)-1-methylimidazole-2-carboxamide, N-cyclohexyl-4,5-di-(4-methylphenyl)-1-methylimidazole-2-carboxamide, N-(cyclohexyl)-4-(2,4-dichlorophenyl)-5-(4-chlorophenyl)-1-methylimidazole-2-carboxamide, and N-(phenyl)-4-(2,4-dichlorophenyl)-5-(4-chlorophenyl)-1-methylimidazole-2-carboxamide which can be prepared as described in PCT Publication No. WO 03/075660; the hydrochloride, mesylate and besylate salt of 1-[9-(4-chloro-phenyl)-8-(2-chloro-phenyl)-9H-purin-6-yl]-4-ethylamino-piperidine-4-carboxylic acid amide which can be prepared as described in U.S. Publication No. 2004/0092520; 1-[7-(2-chloro-phenyl)-8-(4-chloro-phenyl)-2-methyl-pyrazolo[1,5-a][1,3,5]triazin-4-yl]-3-ethylamino-azetidine-3-carboxylic acid amide and 1-[7-(2-chloro-phenyl)-8-(4-chloro-phenyl)-2-methyl-pyrazolo[1,5-a][1,3,5]triazin-4-yl]-3-methylamino-azetidine-3-carboxylic acid amide which can be prepared as described in U.S. Publication No. 2004/0157839; 3-(4-chloro-phenyl)-2-(2-chloro-phenyl)-6-(2,2-difluoro-propyl)-2,4,5,6-tetrahydro-pyrazolo[3,4-c]pyridin-7-one which can be prepared as described in U.S. Publication No. 2004/0214855; 3-(4-chloro-phenyl-2-(2-chloro-phenyl)-7-(2,2-difluoro-propyl)-6,7-dihydro-2H,5H-4-oxa-1,2,7-triaza-azulen-8-one which can be prepared in U.S. Publication No. 2005/0101592; 2-(2-chloro-phenyl)-6-(2,2,2-trifluoro-ethyl)-3-(4-trifluoromethyl-phenyl)-2,6-dihydro-pyrazolo[4,3-d]pyrimidin-7-one which can be prepared as described in U.S. Publication No. 2004/0214838; (S)-4-chloro-N-[3-(4-chloro-phenyl)-4-phenyl-4,5-dihydro-pyrazol-1-yl]-methylamino-methylene)benzenesulfonamide (SLV-319) and (S)—N-{[3-(4-chloro-phenyl)-4-phenyl-4,5-dihydro-pyrazol-1-yl]-methylamino-methylene}-4-trifluoromethyl-benzenesulfonamide (SLV-326) which can be prepared as described in PCT Patent Application Publication No. WO 02/076949; N-piperidino-5-(4-bromophenyl)-1-(2,4-dichlorophenyl)-4-ethylpyrazole-3-carboxamide which can be prepared as described in U.S. Pat. No. 6,432,984; 1-[bis-(4-chloro-phenyl)-methyl]-3-[(3,5-difluoro-phenyl)-methanesulfonyl-methylene]-azetidine which can be prepared as described in U.S. Pat. No. 6,518,264; 2-(5-(trifluoromethyl)pyridin-2-yloxy)-N-(4-(4-chlorophenyl)-3-(3-cyanophenyl)butan-2-yl)-2-methylpropanamide which can be prepared as described in PCT Publication No. WO 04/048317; 4-{[6-methoxy-2-(4-methoxyphenyl)-1-benzofuran-3-yl]carbonyl}benzonitrile (LY-320135) which can be prepared as described in U.S. Pat. No. 5,747,524; 1-[2-(2,4-dichlorophenyl)-2-(4-fluorophenyl)-benzo[1,3]dioxole-5-sulfonyl]-piperidine which can be prepared as described in WO 04/013120; and [3-amino-5-(4-chlorophenyl)-6-(2,4-dichlorophenyl)-furo[2,3-b]pyridin-2-yl]-phenyl-methanone which can be prepared as described in PCT Publication No. WO 04/012671.

Preferred intestinal-acting MTP inhibitors include dirlotapide ((S)—N-{2-[benzyl(methyl)amino]-2-oxo-1-phenylethyl}-yl-methyl-5-[4'-(trifluoromethyl)[1,1'-biphenyl]-2-carboxamido]-1H-indole-2-carboxamide) and 1-methyl-5-[(4'-trifluoromethyl-biphenyl-2-carbonyl)-amino]-1H-indole-2-carboxylic acid (carbamoyl-phenyl-methyl)-amide which can both be prepared using methods described in U.S. Pat. No. 6,720,351; (S)-2-[(4'-trifluoromethyl-biphenyl-2-carbonyl)-amino]quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid ([(4-fluoro-benzyl)-methyl-carbamoyl]-phenyl-methyl)-amide, and (S)-2-[(4'-tert-butyl-biphenyl-2-carbonyl)-amino]-quinoline-6-carboxylic acid [(4-fluoro-benzylcarbamoyl)-phenyl-methyl]-amide which can all be prepared as described in U.S. Publication No. 2005/0234099; (−)-4-[4-[4-[4-[[(2S,4R)-2-(4-chlorophenyl)-2-[[(4-methyl-4H-1,2,4-triazol-3-yl)sulfanyl]methyl-1,3-dioxolan-4-yl]methoxy]phenyl]piperazin-1-yl]phenyl]-2-(1R)-1-methylpropyl]-2,4-dihydro-3H-1,2,4-triazol-3-one (also known as Mitratapide or R103757, also known under the tradename Yarvitan™) which can be prepared as described in U.S. Pat. Nos. 5,521,186 and 5,929,075; and implitapide (BAY 13-9952) which can be prepared as described in U.S. Pat. No. 6,265,431.

Most preferred is dirlotapide, mitratapide, (S)-2-[(4'-trifluoromethyl-biphenyl-2-carbonyl)-amino]-quinoline-6-carboxylic acid (pentylcarbamoyl-phenylmethyl)-amide, (S)-2-[(4'-tert-butyl-biphenyl-2-carbonyl)-amino]-quinoline-6-carboxylic acid {[(4-fluoro-benzyl-methyl-carbamoyl]-phenyl-methyl}-amide, or (S)-2-[(4'-tert-butyl-biphenyl-2-carbonyl-amino]-quinoline-6-carboxylic acid [(4-fluoro-benzylcarbamoyl)-phenyl-methyl]-amide.

A preferred CCKa agonist includes N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide which can be prepared as described in PCT Publication No. WO 2005/116034 or US Publication No. 2005-0267100 A1.

Preferred NPY Y5 antagonists include: 2-oxo-N-(5-phenylpyrazinyl)-spiro[isobenzofuran-1(3H), 4'-piperidine]-1'-carboxamide which can be prepared as described in U.S. Publication No. 2002/0151456; and 3-oxo-N-(5-phenyl-2-pyrazinyl)spiro[isobenzofuran-1(3H), 4'-piperidine]-1'-carboxamide; 3-oxo-N-(7-trifluoromethylpyrido[3,2-b]pyridin-2-yl)-spiro-[isobenzofuran-1(3H), 4'-piperidine]-1'-carboxamide; N-[5-(3-fluorophenyl)-2-pyrimidinyl]-3-oxospiro-[isobenzofuran-1(3H), [4'-piperidine]-1'-carboxamide; trans-3'-oxo-N-(5-phenyl-2-pyrimidinyl]spiro[cyclohexane-1,1'(3'H)-isobenzofuran]-4-carboxamide; trans-3'-oxo-N-[1-(3-quinolyl)-4-imidazolyl]spiro[cyclohexane-1,1'(3'H)-isobenzofuran]-4-carboxamide; trans-3-oxo-N-(5-phenyl-2-pyrazinyl)spiro[4-azaiso-benzofuran-1(3H), 1'-cyclohexane]-4'-carboxamide; trans-N-[5-(3-fluorophenyl)-2-pyrimidinyl]-3-oxospiro[5-azaisobenzofuran-1(3H), 1'-cyclohexane]-4'-carboxamide; trans-N-[5-(2-fluorophenyl)-2-pyrimidinyl]-3-oxospiro[5-azaisobenzofuran-1(3H), 1'-cyclohexane]-4'-carboxamide; trans-N-[1-(3,5-difluorophenyl)-4-imidazolyl]-3-oxospiro[7-azaisobenzofuran-1(3H),1'-cyclohexane]-4'-carboxamide; trans-3-oxo-N-(1-phenyl-4-pyrazolyl)spiro[4-azaisobenzofuran-1(3H),1'-cyclohexane]-4'-carboxamide; trans-N-[1-(2-fluorophenyl)-3-pyrazolyl]-3-oxospiro[6-azaisobenzofuran-1(3H), 1'-cyclohexane]-4'-carboxamide; trans-3-oxo-N-(1-phenyl-3-pyrazolyl)spiro[6-azaisobenzofuran-1(3H), 1'-cyclohexane]-4'-carboxamide; and trans-3-oxo-N-(2-phenyl-1,2,3-triazol-4-yl)spiro[6-azaisobenzofuran-1(3H), 1'-cyclohexane]-4'-carboxamide, all of which can be prepared as described in described in PCT Publication No. WO 03/082190; and pharmaceutically acceptable salts and esters thereof.

All of the above recited U.S. patents and publications are incorporated herein by reference.

Evidence in the literature has also been shown that opioid receptor antagonists would be useful in the treatment of type-2 diabetes (insulin resistance), inflammation, depression, and liver fibrosis. Consequently, the compounds of the present invention may also be used to treat these indications in addition to the obesity and obesity related diseases described above.

Insulin resistance: Cucinelli et al., *Fertility and Sterility*, 81(4)1047-1054 (2004). (Naltrexone was shown to improve insulin sensitivity in post-menopausal women with hyperinsulinemia); Fulghesu, et al., *Metabolism*, 47(2): 158-162 (1998). (Naltrexone was shown to improve insulin sensitivity in Polycystic Ovarian Syndrome (PCOS) women with hyperinsulinemia); and VilIa, et al., *Metabolism, Clinical and Experimental*, 46(5) 538-543 (1997). (Naltrexone was shown to improve insulin sensitivity in Polycystic Ovarian Syndrome (PCOS) women with hyperinsulinemia).

Inflammation: Greeneltech, et al., *Brain, Behavior and Immunity*, 18:476-484 (2004). (Naltrexone was shown to inhibit LPS-stimulated TNF-α production in rats).

Depression: Mague, *J Pharmacol Exp Ther*, 305: 323-330 (2003). (Kappa opioid receptor antagonists were shown to be active in rodent model for depression).

Liver fibrosis: Ebrahimkhani, et al., *Gut*, 55: 1606-1616 (2006). (Naltrexone was shown to attenuate liver fibrosis in bile duct ligated rats).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England). The following abbreviations are used in the preparations to represent the corresponding materials listed below.

EDCl: 1-ethyl-3-[3-(dimethylamino)propyl]-carbodiimide hydrochloride

General Experimental Procedures

NMR spectra were recorded on a Varian Unity™ 400 (available from Varian Inc., Palo Alto, Calif.) at room temperature at 400 MHz for proton. Chemical shifts are expressed in parts per million (6) relative to residual solvent as an internal reference. The peak shapes are denoted as follows: s, singlet; d, doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (Cl) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). Where the intensity of chlorine or bromine-containing ions are described, the expected intensity ratio was observed (approximately 3:1 for $^{35}Cl/^{37}Cl$ containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Preparation of Key Intermediates

Preparation of Intermediate 4-Bromo-2,6-difluoro-benzaldehyde (I-1a)

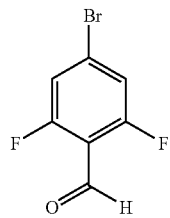

(I-1a)

A solution of diisopropylamine (194.4 mmol) in tetrahydrofuran (350 mL) was cooled in an ice/water bath as n-BuLi (69.5 mL of a 2.5 M solution in hexanes) was added slowly via syringe. After 30 minutes, the solution was cooled in a dry ice/acetone bath as 1-bromo-3,5-difluorobenzene (173.7 mmol in 50 mL of tetrahydrofuran) was added gradually over the course of 25 minutes. After stirring for 30 minutes, dimethylformamide (208.4 mmol) was added gradually to the reaction mixture over the course of 30 minutes. After stirring for 2 hours more in the cooling bath, acetic acid (35 mL) was added, the cooling bath removed, and water (500 mL) was added. The reaction mixture was then extracted with ether (1 L), and the organic phase was washed with 1 N HCl (250 mL), brine, dried over magnesium sulfate and filtered. After condensing the organic phase with a rotary evaporator, the resulting brown solid was tritrated with hexanes before filtration to afford the title compound (I-1a) as a colorless solid (37.8 g).

$^1$H NMR (CDCl$_3$): δ7.20 (d, 2H), 10.27 (s, 1H)
MS: (M+1) 220.

Preparation of intermediate (4-Bromo-2,6-difluoro-benzyl)-(3-methyl-butyl)-amine (I-1b)

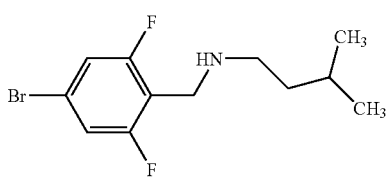

(I-1b)

4-Bromo-2,6-difluoro-benzaldehyde (I-1a: 30 g) and isoamyl amine (13 g) were combined in dichloroethane (1 L) at ambient temperature. After stirring for 2 hours, sodium triacetoxyborohydride (144 g) was added to the reaction mixture. After stirring overnight, the reaction mixture was treated with a 2 M aqueous potassium hydroxide solution. The layers were separated and the organic phase dried over magnesium sulfate before being filtered and concentrated with a rotary evaporator to provide the title compound (I-1b) as an oil, which was used in the subsequent transformation without further purification.

$^1$H NMR (CDCl$_3$): δ 0.84 (d, 6H), 1.22 (bs, 1H), 1.34 (dt, 2H), 1.57 (m, 1H), 2.54 (m, 2H), 3.80 (s, 2H), 7.04 (d, 2H).
MS: 292 (M+1).

Preparation of Intermediate (4-Bromo-2,6-difluoro-benzyl)-(3-methyl-butyl)-carbamic acid tert-butyl ester (I-1c)

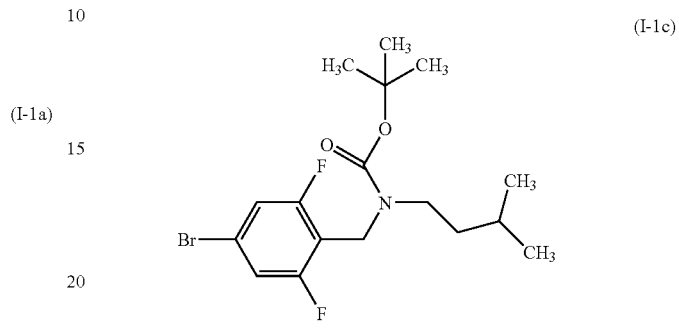

(I-1c)

(4-Bromo-2,6-difluoro-benzyl)-(3-methyl-butyl)-amine (I-1b: 40 g), Boc$_2$O (210 mmol) and potassium carbonate (29 g) were combined in ethyl acetate (250 mL) and the mixture heated to 60° C. After 8 hours, water was added to the reaction mixture and the organic layer was separated, dried over magnesium sulfate, filtered and concentrated. The residue was purified by chromatography on silica gel eluting with 1% to 5% ethyl acetate in heptane to afford the title compound (I-1c).

$^1$H NMR (CDCl$_3$): δ 0.85 (d, 6H), 1.30-1.60 (m, 12H), 3.00-3.20 (m, 2H), 4.40-4.55 (m, 2H), 7.00-7.10 (m, 2H).

Preparation of Intermediate (4'-Cyano-3,5-difluoro-2'-methyl-biphenyl-4-ylmethyl)-(3-methyl-butyl)-carbamic acid tert-butyl ester (I-1d)

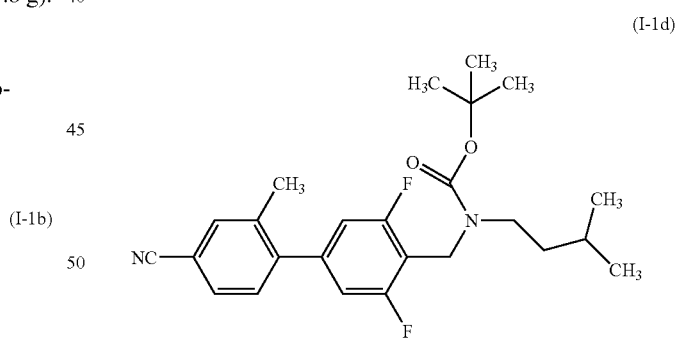

(I-1d)

4-Bromo-2,6-difluoro-benzyl)-(3-methyl-butyl)-carbamic acid tert-butyl ester (I-1c: 10.0 g) was combined with 4-cyano-2-methylphenylboronic acid (6.0 g), palladium tetrakis (triphenylphosphine) (2.2 g), 1,2-dimethoxy ethane (60 ml) and 2M aqueous sodium carbonate (5.0 ml) under a nitrogen atmosphere. After stirring vigorously while being heated at reflux for 12 hours, the reaction mixture was cooled to room temperature, diluted with water and extracted with ethyl acetate (2 times). The combined organic layers were washed with brine, dried over magnesium sulfate, filtered and concentrated under reduced pressure. The residue was purified by chromatography on silica eluting with ethyl acetate in heptane to provide the title compound (I-1d).

¹H NMR (CDCl₃): δ 0.87 (d, 6H), 1.3-1.6 (m, 12H), 2.28 (s, 3H), 3.1-3.3 (m, 2H), 4.5-4.7 (m, 2H), 6.81 (d, 2H), 7.27 (d, 1H), 7.20 (d, 1H), 7.56 (s, 1H).

Preparation of Intermediate (4'-Carbamoyl-3,5-difluoro-2'-methyl-biphenyl-4-ylmethyl)-(3-methyl-butyl)-carbamic acid tert-butyl ester (I-1e)

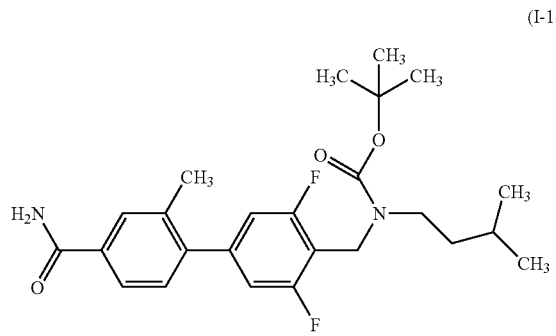

(I-1e)

(4'-Cyano-3,5-difluoro-2'-methyl-biphenyl-4-ylmethyl)-(3-methyl-butyl)-carbamic acid tert-butyl ester (I-1d: 30 g) was dissolved in 150 mL dimethyl sulfoxide and combined with potassium carbonate (20 g) and 20 mL of a 30% hydrogen peroxide solution in water. After stirring at room temperature for 12 hours, the reaction mixture was quenched with water and extracted using ethyl acetate (250 mL). The organic layer was washed with water (2 times), brine, dried over magnesium sulfate, filtered and concentrated. The residue was purified by chromatography on silica eluting with 50% ethyl acetate in heptane to provide 28 g of the title compound (I-1e).

¹H NMR (CDCl₃): δ 0.87 (d, 6H), 1.3-1.6 (m, 12H), 2.30 (s, 3H), 3.1-3.3 (m, 2H), 4.5-4.7 (m, 2H), 5.78 (bs, 1H), 6.14 (bs, 1H), 6.83 (d, 2H), 7.25 (d, 1H), 7.64 (d, 1H), 7.74 (s, 1H).

Preparation of Intermediate 4-Bromo-3-methyl-benzaldehyde (I-2a)

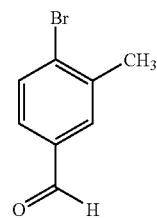

(I-2a)

The starting material (4-bromo-3-methyl-benzonitrile, 12.8 g, 65.3 mmol) was dissolved in toluene (120 mL) and dichloromethane (20 mL) and cooled to −60° C. as a 1.5M diisobutylaluminum hydride in toluene (67 mL, 100 mmol) was added dropwise over 30 minutes keeping the temperature between −60 and −50° C. The reaction was allowed to warm slowly to room temperature and stirred for an additional 3 hours. The reaction was quenched by adding ethyl acetate and stirring for 20 minutes before the addition of 1N aqueous hydrochloric acid at 0° C. The reaction mixture was then allowed to warm slowly to room temperature before extractive workup in the usual manner using ethyl acetate (2 times).

The combined organic layers were washed with brine, dried over sodium sulfate, filtered and concentrated under reduced pressure. The residue was purified by chromatography on silica eluting with 5% ethyl acetate in heptane to yield 5.6 μg of the title compound (I-2a).

¹H NMR (CDCl₃): δ 2.47 (s, 3H), 7.54 (dd, 1H), 7.69-7.72 (m, 2H), 9.94 (s, 1H)

Preparation of Intermediate (4-Bromo-3-methyl-benzyl)-(3-methyl-butyl)-amine (I-2b)

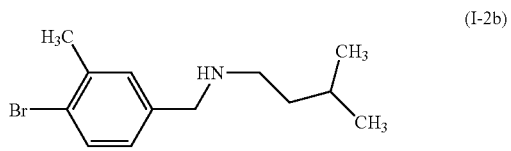

(I-2b)

4-bromo-3-methyl-benzaldehyde (2a: 10.20 g, 51.2 mmol) was dissolved in methanol (150 ml) before adding isoamyl amine (6.75 g, 77 mmol). After stirring overnight at room temperature, sodium borohydride (5.9 g, 154 mmol) was added. After stirring for 1 hour at room temperature, the reaction was quenched using concentrated (37%) hydrochloric acid and the volatiles were removed with a rotary evaporator under reduced pressure. The resulting residue was made basic with a 2 N aqueous sodium hydroxide solution and extracted twice with ethyl acetate. The combined organics were washed with a saturated aqueous sodium bicarbonate solution and dried over sodium sulfate, filtered and concentrated under reduced pressure to provide 13.7 g of the title compound (I-2b).

¹H NMR (CDCl₃): δ 0.87 (d, 6H), 1.38 (m, 2H), 1.44 (bs, 1H), 1.61 (m, 1H), 2.36 (s, 3H), 2.60 (m, 2H), 3.69 (s, 2H), 6.98 (dd, 1H), 7.19 (d, 1H), 7.44 (d, 1H). MS: 270 (M+1)

Preparation of Intermediate (4-Bromo-3-methyl-benzyl)-(3-methyl-butyl)-carbamic acid tert-butyl ester (I-2c)

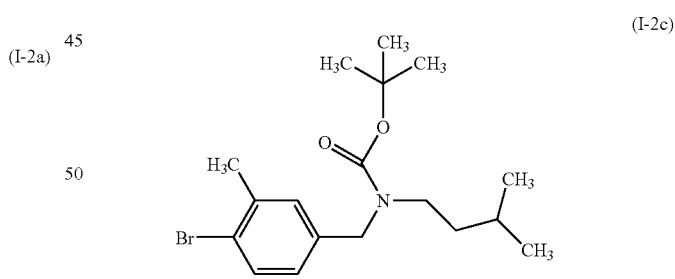

(I-2c)

(4-bromo-3-methyl-benzyl)-(3-methyl-butyl)-amine (I-2b: 13.7 g) was dissolved in 100 mL of ethyl acetate and treated with 200 mL of a saturated aqueous sodium bicarbonate solution and di-tert-butyl-carbonate (14.3 g, 65.5 mmol). The reaction mixture was stirred at 50° C. for 2 hours before cooling to room temperature and the aqueous phase extracted with ethyl acetate. The combined organic phases were washed with brine, dried over sodium sulfate, filtered and concentrated to provide the title compound (I-2c).

¹H NMR (CDCl₃): δ 0.86 (d, 6H), 1.35-1.56 (m, 12H), 2.36 (s, 3H), 3.0-3.3 (m, 2H), 4.3 (m, 2H), 6.9 (m, 1H), 7.1 (m, 1H), 7.44 (d, 1H).

Preparation of Intermediate (4-Cyano-2,2'-dimethyl-biphenyl-4-ylmethyl)-(3-methyl-butyl)carbamic acid tert-butyl ester (I-2d)

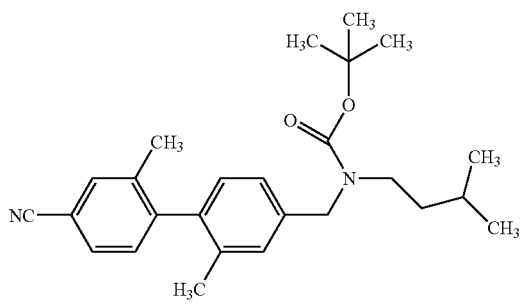

(I-2d)

(4-bromo-3-methyl-benzyl)-(3-methyl-butyl)-carbamic acid tert-butyl ester (I-2c: 12 g) was combined with 4-cyano-2-methylphenylboronic acid (7.20 g), palladium tetrakis (triphenylphosphine) (3.0 g), 1,2-dimethoxy ethane (100 ml) and 2M aqueous sodium carbonate (50 mL). After stirring vigorously while being heated at 95° C. for 48 hours, the reaction mixture was cooled to room temperature, diluted with water and extracted with ethyl acetate (2 times). The combined organic layers were washed with brine, dried over sodium sulfate, filtered and concentrated under reduced pressure. The residue was purified by chromatography on silica eluting with 10% ethyl acetate in heptane to provide the title compound (I-2d).

$^1$H NMR (CDCl$_3$): δ 0.87 (d, 6H), 1.3-1.6 (m, 12H), 1.99 (s, 3H), 2.06 (s, 3H), 3.1-3.3 (m, 2H), 4.4 (m, 2H), 6.97 (d, 1H), 7.08-7.11 (m, 2H), 7.18 (d, 1H), 7.50 (d, 1H), 7.55 (s, 1H).

Preparation of Intermediate (4-Carbamoyl-2,2'-dimethyl-biphenyl-4-ylmethyl)-(3-methyl-butyl)-carbamic acid tert-butyl ester (I-2e)

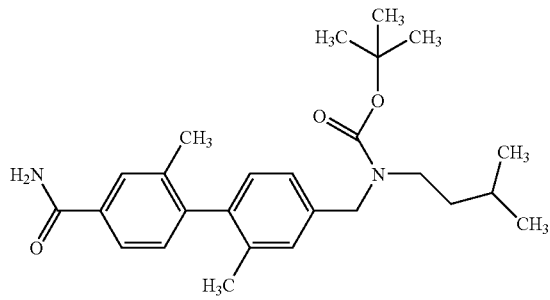

(I-2e)

(4'-cyano-2,2-dimethyl-biphenyl-4-ylmethyl)-(3-methyl-butyl)-carbamic acid tert-butyl ester (I-2d: 12.5 g) was dissolved in 100 mL dimethyl sulfoxide and combined with potassium carbonate (4.3 g) and 4.0 mL of a 30% hydrogen peroxide solution in water. After stirring at room temperature for 2 hours, the reaction mixture was quenched with water and extracted using ethyl acetate (2 times). The combined organic layers were washed with water (5 times), brine, dried over sodium sulfate, filtered and concentrated. The residue was purified by chromatography on silica eluting with 50-60% ethyl acetate in heptane to provide the title compound (I-2e).

$^1$H NMR (CDCl$_3$): δ 0.87 (d, 6H), 1.3-1.6 (m, 12H), 2.00 (s, 3H), 2.08 (s, 3H), 3.1-3.3 (m, 2H), 4.4 (m, 2H), 5.6 (m, 1H), 6.1 (m, 1H), 6.99 (d, 1H), 7.08 (d, 1H), 7.11 (s, 1H), 7.16 (d, 1H), 7.62 (d, 1H), 7.73 (s, 1H).

Preparation of Intermediate 4-Bromo-2-chloro-benzaldehyde (I-3a)

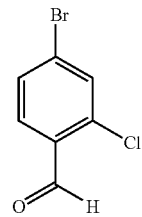

(I-3a)

The 4-Bromo-2-chloro-benzaldehyde was prepared using procedures described in *J. Med. Chem.* 1981, 24, 1155-1161.

4-bromo-2-chloro-benzonitrile (7.05 g, 32.5 mmol) was dissolved in toluene (60 mL) and dichloromethane (10 mL) and cooled to −60° C. as a 1.5M solution of diisobutylaluminum hydride in toluene (33.4 ml, 49.8 mmol) was added dropwise over 30 minutes keeping the temperature between −60 and −50° C. The reaction was allowed to warm slowly to room temperature and stirred for an additional 3 hours. The reaction was quenched using ethyl acetate and stirred for 20 minutes before the addition of 1N hydrochloric acid at 0° C. The reaction was then allowed to warm slowly to room temperature. The reaction was extracted using ethyl acetate (2 times). Removal of the solvent provided the title compound (I-3a).

$^1$H NMR (CDCl$_3$): δ 7.52 (dd, 1H), 7.84 (d, 1H), 7.77 (d, 1H), 10.4 (s, 1H)

Preparation of Intermediate (4-Bromo-2-chloro-benzyl)-(3-methyl-butyl)-amine (I-3b)

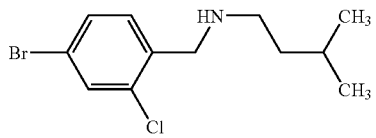

(I-3b)

4-bromo-2-chloro-benzaldehyde (I-3a: 10.0 g, 46.0 mmol) was dissolved in methanol and treated with isoamylamine (4.78 g, 54.7 mmol). After stirring overnight at room temperature, sodium borohydride (5.2 g, 138 mmol) was added to the reaction mixture. After stirring for 1 hour at room temperature, the reaction mixture was quenched using concentrated (37%) hydrochloric acid and the volatiles were removed under reduced pressure. The residue was taken up in an aqueous 2 N sodium hydroxide solution and extracted with ethyl acetate (2 times). The combined organic phases were washed with a saturated aqueous sodium bicarbonate solution, dried over sodium sulfate, filtered and concentrated under reduced pressure to afford the title product (I-3b: 12.7 g)

¹H NMR (CDCl₃): δ 0.87 (d, 6H), 1.40 (dt, 2H), 1.62 (th, 1H), 1.8 (bs, 1H), 2.61 (t, 2H), 3.82 (s, 2H), 7.28 (d, 1H), 7.36 (d, 1H), 7.50 (s, 1H).

Preparation of Intermediate (4-Bromo-2-chloro-benzyl)-(3-methyl-butyl)-carbamic acid tert-butyl ester (I-3c)

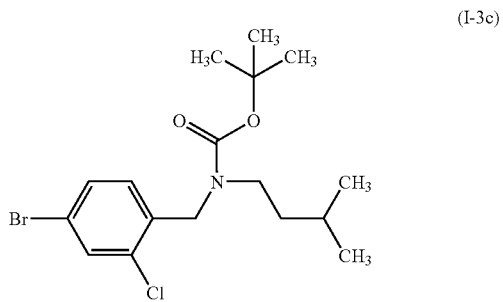

(4-bromo-2-chloro-benzyl)-(3-methyl-butyl)-amine (I-3b: 12.7 g, 43.7 mmol), dissolved in ethyl acetate (100 mL), was combined with a saturated aqueous sodium bicarbonate solution (200 mL)) and di-tert-butyl-dicarbonate (14.3 g, 65.5 mmol). After stirring at 50° C. for 2 hours, the reaction mixture was cooled to room temperature, diluted with water and transferred to a separatory funnel. The aqueous layer was extracted with ethyl acetate. The combined organic layers were washed with brine, dried over sodium sulfate, filtered and concentrated. The product was purified column chromatography using flash silica gel and eluting with 10% ethyl acetate in heptane to provide the title compound (I-3c).

¹H NMR (CDCl₃): δ 0.87 (d, 6H), 1.35-1.56 (m, 12H), 3.1-3.3 (m, 2H), 4.4-4.5 (m, 2H), 7.0-7.15 (m, 1H), 7.3-7.4 (m, 1H), 7.49 (bs, 1H).

Preparation of Intermediate (3-Chloro-4-cyano-2-methyl-biphenyl-4-ylmethyl)-(3-methyl-butyl)-carbamic acid tert-butyl ester (I-3d)

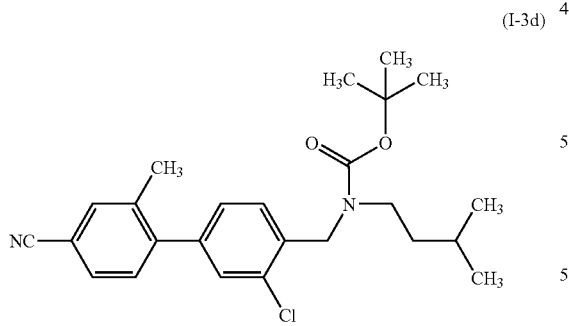

To a 250 ml round bottom flask was added (4-bromo-2-chloro-benzyl)-(3-methyl-butyl)-carbamic acid tert-butyl ester (I-3c: 12 g) followed by the 4-cyano-2-methylphenylboronic acid (7.20 g), 1,2-dimethoxy ethane (100 mL), 2M aqueous sodium carbonate (50 ml) and palladium tetrakis (triphenylphosphine) (3.0 g). After heating the reaction mixture at 95° C. for 48 hours, the mixture was cooled to room temperature, diluted with water and extracted with ethyl acetate (2 times). The combined organic layers were washed with brine, dried over sodium sulfate, filtered and concentrated under reduced pressure to afford the title compound (I-3d).

¹H NMR (CDCl₃): δ 0.89 (d, 6H), 1.3-1.6 (m, 12H), 2.28 (s, 3H), 3.2-3.3 (m, 2H), 4.5-4.6 (m, 2H), 7.15 (d, 1H), 7.28 (bs, 3H), 7.51 (d, 1H), 7.55 (s, 1H).

Preparation of Intermediate (4'-Carbamoyl-3-chloro-2'-methyl-biphenyl-4-ylmethyl)-(3-methyl-butyl)-carbamic acid tert-butyl ester (I-3e)

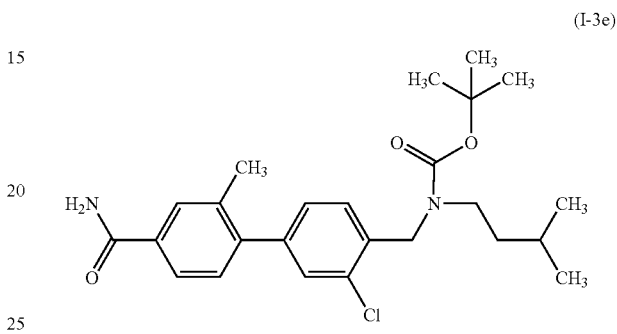

(3-Chloro-4'-cyano-2'-methyl-biphenyl-4-ylmethyl)-(3-methyl-butyl)-carbamic acid tert-butyl ester (I-3d) was dissolved in 100 mL dimethyl sulfoxide (DMSO) and to which was added potassium carbonate and 4.0 mL of 30% hydrogen peroxide in water. The reaction was stirred at room temperature for 2 hours. The reaction was quenched with water and extracted using ethyl acetate (2 times). The combined organic layers were washed with water (5 times), brine, dried over sodium sulfate, filtered and concentrated. The product (I-3e) was isolated by dissolving the crude product in ethyl acetate and addition of heptane.

¹H NMR (CDCl₃): δ 0.89 (d, 6H), 1.3-1.6 (m, 12H), 2.30 (s, 3H), 3.1-3.3 (m, 2H), 4.5-4.6 (m, 2H), 5.6 (m, 1H), 6.1 (m, 1H), 7.17 (d, 1H), 7.2-7.3 (m, 3H), 7.61 (d, 1H), 7.74 (s, 1H).

Preparation of Intermediate 4'-formyl-2-methylbiphenyl-4-carboxamide (I-4a)

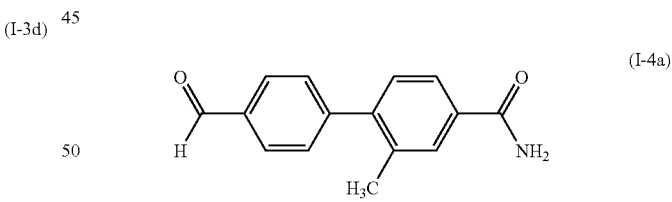

4-Bromo-3-methyl-benzamide (15.02 g), 70 mmol), 4-formylphenylboronic acid (14.039, 91 mmol) and palladium tetrakis(triphenylphosphine) (5.03 g, 4 mmol) were combined in 1,2-dimethoxy ethane (5 ml) and 2M aqueous sodium carbonate (2.5 ml). After heating at 95° C. for 48 hours, the reaction mixture was cooled to ambient temperature and passed through a plug of Celite, rinsing with 1,2-dimethoxy ethane. The volatiles were removed under reduced pressure to yield 16 g of the title compound (I-4a) as a colorless solid.

¹H NMR (400 MHz, Chloroform-d) δ ppm 2.31 (s, 3H), 5.66 (s, 1H), 6.10 (s, 1H), 7.30 (d, J=7.89 Hz, 1H), 7.48 (d, J=8.10 Hz, 2H), 7.67 (d, J=7.89 Hz, 1H), 7.77 (s, 1H), 7.95 (d, J=7.89 Hz, 2 H), 10.07 (s, 1H). Mass Spec.: (m/z+1=240)

Preparation of (4'-carbamoyl-2'-methyl-biphenyl-4-ylmethyl)-(3-methyl-butyl)-carbamic acid tert-butyl ester (I-4-b)

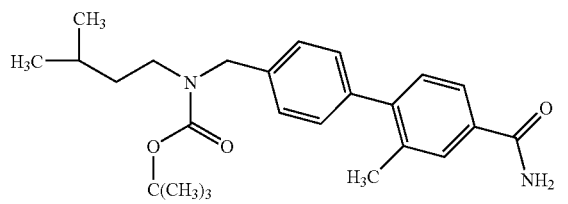

[2-Methyl-4'-[(3-methyl-butylamino)-methyl]-biphenyl-4-carboxylic acid amide (A: 5.8 g, 19 mmol) was dissolved in ethyl acetate (25 ml) and treated with an aqueous saturated sodium bicarbonate solution (50 ml) and di-tert-butyl dicarbonate (6.12 g, 28 mmol). The reaction mixture was heated to 50° C. and after 2 hours cooled to room temperature, diluted with water and the layers were separated. The organic layer was washed with brine, dried over sodium sulfate, filtered and concentrated under reduced pressure. The residue was purified using chromatography on silica gel eluting with 10% ethyl acetate in hexanes to yield 7.0 g of (4'-carbamoyl-2'-methyl-biphenyl-4-ylmethyl)-(3-methyl-butyl)-carbamic acid tert-butyl ester (I-4b).

Preparation of Intermediate 4-Bromo-3-fluoro-N-(3-methylbutyl)benzamide (I-5a)

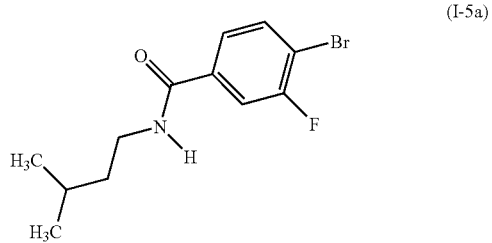

4-Bromo-3-fluorobenzoic acid (2.00 g, 9.13 mmol) was dissolved in dichloromethane (20 mL) and cooled in an ice/water bath as EDCl (2.10 g, 10.9 mmol) was added. After addition, the reaction mixture was allowed to warm to ambient temperature and stirred for 30 minutes before adding isoamylamine (1.59 g, 18.3 mmol). After 12 hours, water was added and the reaction mixture was extracted with ethyl ether. The combined organic layers were washed sequentially with 1N HCl, 1N NaOH and brine. The organic phase was dried over sodium sulfate, filtered and concentrated. The resulting residue was purified by chromatography on silica gel eluting with 5% ethyl acetate in heptane to afford the title compound (I-5a).

$^1$H NMR (400 MHz, Chloroform-d) δ ppm 0.94 (d, J=6.44 Hz, 6H), 1.46-1.53 (m, 2H), 1.66 (dt, J=13.44, 6.67 Hz, 1H), 3.42-3.48 (m, 2H), 6.01 (s, 1H), 7.38 (dd, J=8.20, 1.97 Hz, 1H), 7.52 (dd, J=9.03, 1.97 Hz, 1H), 7.60 (dd, J=8.31, 6.64 Hz, 1H). Mass Spec.: (m/z+1=289)

Preparation of Intermediate (4-Bromo-3-fluoro-benzyl)-(3-methyl-butyl)-amine (I-5b)

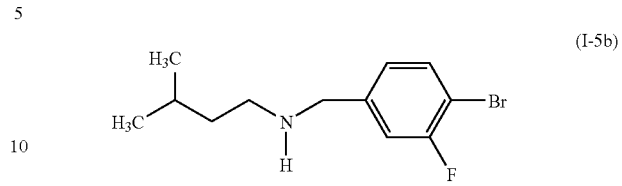

4-Bromo-3-fluoro-N-(3-methylbutyl)benzamide (I-5a: 2.6 g, 9.02 mmol) was dissolved in tetrahydrofuran (20 ml) and treated with 1M borane in tetrahydrofuran (20 ml, 18.04 mmol) at room temperature. After heating at reflux for 24 hours, the reaction mixture was carefully treated with concentrated HCl and then heated at reflux for 1 additional hour. After cooling to ambient temperature, the reaction mixture was filtered and the resulting solid suspended in 1N aqueous NaOH and the mixture extracted twice with ethyl acetate. The combined organic layers were washed with brine, dried over sodium sulfate, filtered and evaporated under reduced pressure. The resulting material used in the subsequent reaction without further purification.

$^1$H NMR (400 MHz, Chloroform-d) δ ppm 0.87 (dd, J=6.64, 1.04 Hz, 6H), 1.32-1.42 (m, 2H), 1.62 (dt, J=13.24, 6.57 Hz, 1H), 2.59 (t, J=7.48 Hz, 2H), 3.73 (s, 2H), 6.98 (d, J=8.10 Hz, 1H), 7.11 (d, J=9.55 Hz, 1H), 7.45 (t, J=7.68 Hz, 1H).

Mass Spec.: (m/z+1=275)

Preparation of Intermediate (4-Bromo-3-fluoro-benzyl)-(3-methyl-butyl)carbamic acid tert-butyl ester (I-5c)

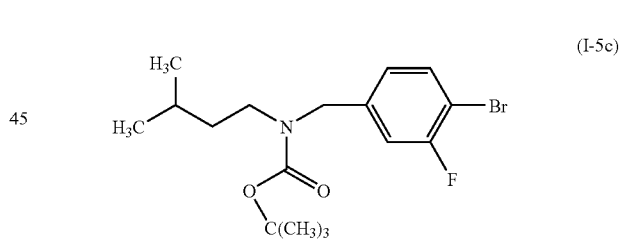

(4-Bromo-3-fluoro-benzyl)-(3-methyl-butyl)-amine (I-5b: 1.78 g, 6.5 mmol) was dissolved in ethyl acetate (20 ml) and treated with an aqueous saturated sodium bicarbonate solution (40 ml) and di-tert-butyl dicarbonate (2.13 g, 9.73 mmol). After 2 hours, the reaction mixture was diluted with water and extracted twice with ethyl acetate. The combined organic layers were washed with water, brine, dried over sodium sulfate, filtered and concentrated under reduced pressure. The residue was purified using chromatography on silica gel eluting with 5% ethyl acetate in hexanes to yield 2.45 g of the title product (I-5c).

$^1$H NMR (400 MHz, Chloroform-d) δ ppm 0.87 (d, J=6.64 Hz, 6H), 1.33-1.50 (m, 3H), 1.51 (s, 9H), 3.16 (d, 2H), 4.35 (s, 2H), 6.88 (s, 1H), 6.98 (s, 1H), 7.46 (t, J=7.58 Hz, 1H). Mass Spec.: (m/z+1=375)

Preparation of Intermediate (3'-Cyano-2-fluoro-biphenyl-4-ylmethyl)-(3-methyl-butyl)-carbamic acid tert-butyl ester (I-5d)

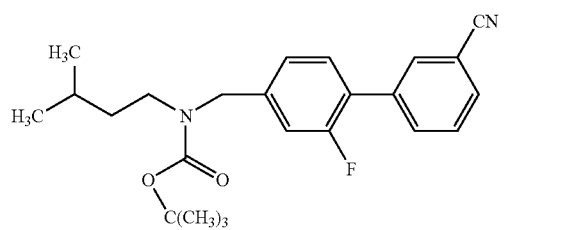
(I-5d)

(4-Bromo-3-fluoro-benzyl)-(3-methyl-butyl)-carbamic acid tert-butyl ester (I-5c: 1.5 g, 4.00 mmol) was dissolved in 1,2-dimethoxyethane (15 ml) under nitrogen. Palladium tetrakis(triphenylphospine) (5 mol %) was added followed by an aqueous 2 M sodium carbonate solution (7 ml) and 3-cyanophenyl boronic acid (0.883 g, 6.01 mmol) was added. The reaction mixture was heated at reflux for 24 hours before being cooled to room temperature and filtered through Celite, rinsing with dimethoxyethane. The filtrate was concentrated under reduced pressure and the residue purified by chromatography on silica gel eluting with 10% ethyl acetate in hexanes to afford 1.25 g (78%) of title product (I-5d).

$^1$H NMR (400 MHz, Chloroform-d) δ ppm 0.89 (d, J=6.44 Hz, 6H), 1.35-1.55 (m, 12H), 3.12-3.32 (m, 2H), 4.45 (s, 2H), 7.02-7.13 (m, J=11.63 Hz, 2H), 7.35 (t, J=7.89 Hz, 1H), 7.53 (t, J=7.79 Hz, 1H), 7.63 (d, J=7.68 Hz, 1H), 7.76 (d, J=7.68 Hz, 1H) 7.82 (s, 1H). Mass Spec.: (m/z+1=397)

(3'-Carbamoyl-2-fluoro-biphenyl-4-ylmethyl)-(3-methyl-butyl)-carbamic acid tert-butyl ester (I-5e)

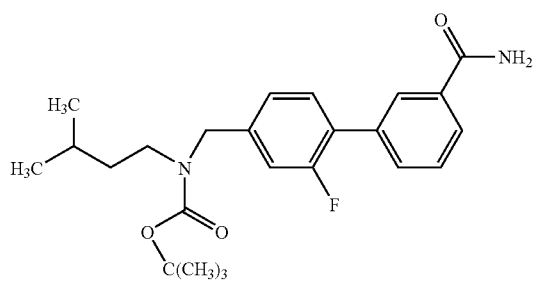
(I-5e)

(3'-Cyano-2-fluoro-biphenyl-4-ylmethyl)-(3-methyl-butyl)-carbamic acid tert-butyl ester (I-5d: 1.20 g, 3.02 mmol) was dissolved in dimethyl sulfoxide (5.5 ml) and treated with potassium carbonate (0.502 g, 3.6 mmol) and 0.250 ml of a 30% hydrogen peroxide solution. After 18 hours, the reaction mixture was diluted with water and extracted with ethyl acetate (3×). The combined organic layers were washed with water and brine, dried over sodium sulfate, filtered and concentrated under reduced pressure to afford the title compound (1.25 g, 99%), which was pure enough to be taken on and used directly in the next reaction.

$^1$H NMR (400 MHz, Chloroform-d) δ ppm 0.88 (t, J=6.96 Hz, 6H), 1.40-1.52 (m, 12H), 3.09-3.33 (m, 2H), 4.45 (s, 2H), 5.64 (s, 1H), 6.11 (s, 1H), 7.05 (s, 2H), 7.40 (t, J=7.89 Hz, 1H), 7.51 (t, J=7.79 Hz, 1H), 7.70 (d, J=7.68 Hz, 1H), 7.79 (dt, J=7.89, 1.45 Hz, 1H), 7.97 (s, 1H).

Preparation of Intermediate trifluoro-methanesulfonic acid 2-chloro-4-formyl-phenyl ester (I-6a)

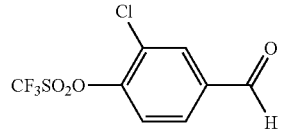
(I-6a)

3-Chloro-4-hydroxy-benzaldehyde (10.0 g) and pyridine (9.16 g) were combined in 250 mL of dichloromethane and the resulting solution was cooled in an ice/water bath as trifluoromethylsulfonic acid anhydride (19.6 g) was added gradually over the course of 15 minutes. After 1 hour, the ice/water bath was removed and the reaction mixture stirred for an additional hour as it warmed to ambient temperature. The reaction mixture was combined with a sodium bicarbonate solution that has been cooled with ice, the organic layer was separated, washed twice with a 1 N aqueous HCl solution, dried over magnesium sulfate, filtered and concentrated under reduced pressure. The resulting residue was purified by chromatography on silica gel eluting with 5% ethyl acetate in heptane to afford the title compound (I-6a).

$^1$H NMR (400 MHz, Chloroform-d) δ ppm 7.54 (d, J=8.51 Hz, 1H), 7.86 (dd, J=8.41, 1.97 Hz, 1H), 8.03 (d, J=2.08 Hz, 1H), 9.98 (s, 1H).

Preparation of Intermediate 2'-Chloro-4'-formyl-biphenyl-3-carbonitrile (I-6b)

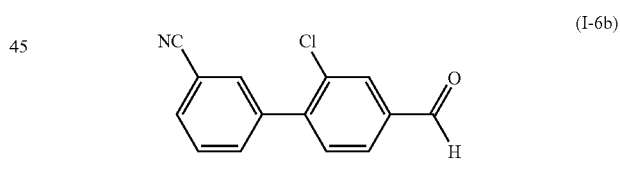
(I-6b)

Trifluoro-methanesulfonic acid 2-chloro-4-formyl-phenyl ester (I-6a: 10.0 g), 3-cyano-phenyl-boronic acid (5.26 g) and palladium tetrakis(triphenylphosphine) (3.00 g) were combined in 100 mL of dimethoxyethane, then treated with 10 mL of a 2M aqueous sodium carbonate solution before being heated in a 100° C. oil bath. After 24 hours, the reaction mixture was cooled to ambient temperature, the organic phase was separated, dried over magnesium sulfate, filtered and concentrated under reduced pressure. The resulting residue was purified by chromatography on silica gel eluting with 10% ethyl acetate in heptane to afford the title compound (I-6b).

$^1$H NMR (400 MHz, Chloroform-d) δ ppm 7.49 (d, J=7.89 Hz, 1H), 7.59 (t, J=7.99 Hz, 1H), 7.68-7.76 (m, 3H), 7.86 (dd, J=7.79, 1.56 Hz, 1H), 8.01 (d, J=1.45 Hz, 1H), 10.03 (s, 1H).

Preparation of Intermediate 2'-Chloro-4'-hydroxymethyl-biphenyl-3-carbonitrile (I-6c)

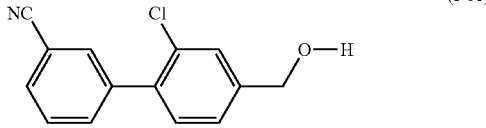

(I-6c)

2'-Chloro-4'-formyl-biphenyl-3-carbonitrile (I-6b: 6.0 g) was dissolved in 150 mL of methanol before sodium borohydride (3.4 g) was added gradually. After 1 hour, the reaction mixture was concentrated under reduced pressure, the resulting residue was taken up in 100 mL of ethyl acetated and washed twice with 20 mL of water. The organic phase was dried over magnesium sulfate, filtered, and concentrated under reduced pressure to afford the title compound (I-6c).

$^1$H NMR (400 MHz, Chloroform-d) δ ppm 4.74 (d, J=5.81 Hz, 2H), 7.27-7.30 (m, 1H), 7.32-7.35 (m, 1H), 7.51-7.55 (m, 2H), 7.64-7.68 (m, 2H), 7.71-7.72 (m, 1H).

Preparation of Intermediate 2'-Chloro-4'-hydroxymethyl-biphenyl-3-carboxylic acid amide (I-6d)

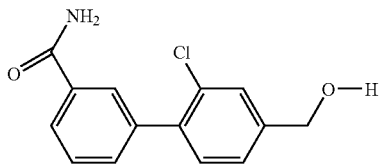

(I-6d)

2'-Chloro-4'-hydroxymethyl-biphenyl-3-carbonitrile (I-6c) was dissolved in 50 mL of dimethylsulfoxide and treated with potassium carbonate (2.8 g) followed by an aqueous hydrogen peroxide solution (10 mL of a 30% solution). After 18 hours, the reaction mixture was combined with 200 mL of water and extracted with ethyl acetate. The organic layer was washed twice with water, dried over magnesium sulfate, filtered and concentrated under reduced pressure to afford the title compound (I-6d).

$^1$H NMR (400 MHz, Chloroform-d) δ ppm 4.73 (d, J=4.57 Hz, 2H), 5.73 (bs, 1H), 6.13 (bs, 1H), 7.31-7.33 (m, 2H), 7.48-7.53 (m, 2H), 7.60 (ddd, J=7.89, 1.45, 1.25 Hz, 1H), 7.81 (dt, J=7.73, 1.53 Hz, 1H), 7.86 (t, J=1.56 Hz, 1H).

Preparation of Intermediate 2'-Chloro-4'-formyl-biphenyl-3-carboxylic acid amide (I-6e)

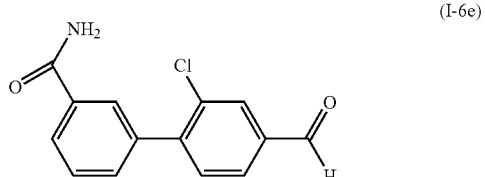

(I-6e)

2'-Chloro-4'-hydroxymethyl-biphenyl-3-carboxylic acid amide (I-6d: 5.0 g) was suspended in 500 mL of ethyl acetate and treated with activated manganese dioxide (5 equivalents). After stirring for 12 hours, the reaction mixture was filtered through a pad of Celite and concentrated under reduced pressure to afford the title compound (I-6e).

$^1$H NMR (400 MHz, Chloroform-d) δ ppm 5.79 (bs, 1H), 6.14 (bs, 1H), 7.52-7.57 (m, 2H), 7.62-7.65 (m, 1H), 7.82-7.87 (m, 2H), 7.91 (t, J=1.66 Hz, 1H), 7.99 (d, J=1.66 Hz, 1H), 10.00 (s, 1H).

Preparation of Intermediate (4'-{[1-Dimethylaminomethylidene]-carbamoyl}-2'-methyl-biphenyl-4-ylmethyl)-(3-methyl-butyl)-carbamic acid tert-butyl ester (I-7a-1)

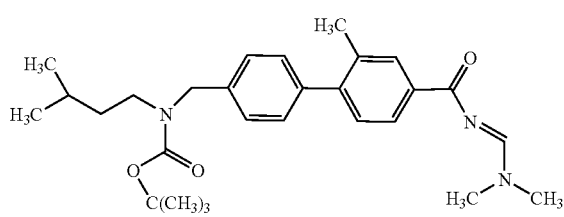

(I-7a-1)

(4'-Carbamoyl-2'-methyl-biphenyl-4-ylmethyl)-(3-methyl-butyl)-carbamic acid tert-butyl ester (I-4-b: 200.0 mg, 0.487 mmol) was dissolved in dimethylformamide dimethylacetal (5.0 ml) and heated to 120° C. After 2 hours, the reaction mixture was cooled to room temperature and the volatiles removed under reduced pressure. The resulting residue was used in the next reaction without further purification.

$^1$H NMR (400 MHz, Chloroform-d) δ ppm 0.87 (d, J=6.44 Hz, 6H), 1.24-1.63 (m, 12H), 2.31 (s, 3H), 3.12-3.27 (m, 2H), 3.31 (s, 6H), 4.44 (d, J=20.56 Hz, 2H), 7.27 (s, 5H), 8.12 (d, J=7.89 Hz, 1H), 8.15 (s, 1H) 8.65 (s, 1H). Mass Spec.: (m/Z=466).

Preparation of Intermediate [3'-(Dimethylaminomethylene-carbamoyl)-2-fluoro-biphenyl-4-ylmethyl]-(3-methyl-butyl)-carbamic acid tert-butyl ester (I-7a-2)

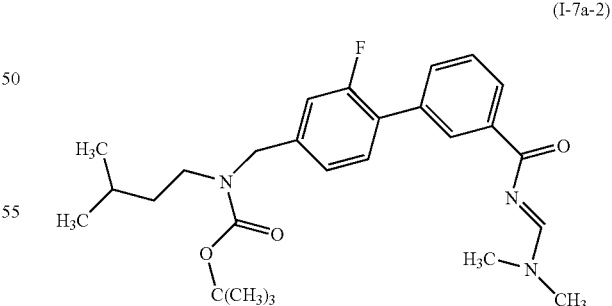

(I-7a-2)

(3'-Carbamoyl-2-fluoro-biphenyl-4-ylmethyl)-(3-methyl-butyl)-carbamic acid tert-butyl ester (I-5e; 0.8 g, 1.92 mmol) was dissolved in dimethylformamide dimethyl acetal (10 ml) and heated to 120° C. for 2 hours. The reaction mixture was then cooled to room temperature and volatiles were removed under reduced pressure. The crude residue (0.9 g) used in the next reaction without purification. Mass Spec.: (m/z+1=470).

Preparation of Intermediate (3-Methyl-butyl)-(2-methyl-4'-nitro-biphenyl-4-ylmethyl)-carbamic acid tert-butyl ester (I-8a)

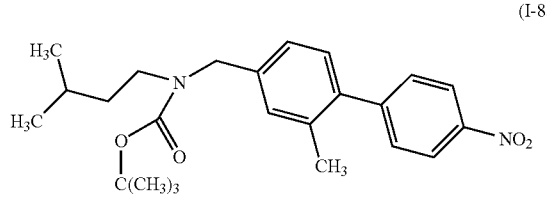
(I-8a)

(4-Bromo-3-methyl-benzyl)-(3-methyl-butyl)-carbamic acid tert-butyl ester (I-2c: 250 mg, 0.675 mmol) was added to a 5 mL microwave vial and dissolved in 2 mL of 1,2-dimethoxyethane. To this solution was added 4-nitro-phenyl boronic acid (146 mg, 0.878 mmol) and 1 mL of a 2M aqueous sodium carbonate solution and tetrakis(triphenylphosphine) palladium (0.040 g, 0.0338 mmol). The reaction mixture was purged with nitrogen and sealed before heating to 80° C. by microwave irradiation for 15 minutes. The reaction mixture was diluted with water (10 mL) and extracted with ethyl acetate (2×10 mL). The combined organic layers were washed with brine, dried over sodium sulfate, filtered and concentrated under reduced pressure. The residue was purified using preparative thin layer chromatography eluting with 15% ethyl acetate in heptane. Collection and extraction of the product-containing band followed by concentration under reduced pressure afforded the title compound (I-8a: 0.150 g).

$^1$H NMR (400 MHz, Chloroform-d) δ ppm 0.89 (d, J=6.64 Hz, 6H), 1.49 (s, 12H), 2.25 (s, 3H), 3.20 (d, J=25.96 Hz, 2H), 4.44 (d, J=0.83 Hz, 2H), 6.99-7.21 (m, 3H), 7.47 (d, J=8.51 Hz, 2H), 8.26 (d, J=8.72 Hz, 2H).

Preparation of Intermediate (4'-Amino-2-methyl-biphenyl-4-ylmethyl)-(3-methyl-butyl)-carbamic acid tert-butyl ester (I-8b)

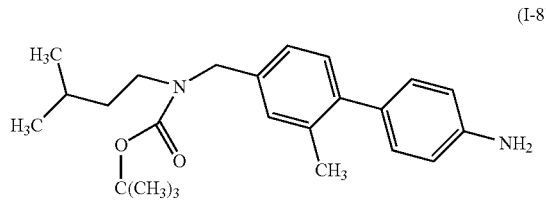
(I-8b)

(3-Methyl-butyl)-(2-methyl-4'-nitro-biphenyl-4-ylmethyl)-carbamic acid tert-butyl ester (I-9a: 0.150 mg, 0.364 mmol) in methanol (12.1 ml) was hydrogenated employing an H-cube apparatus (atmospheric pressure, flow rate=1 mL/min, hydrogen level=full hydrogen, temperature=35° C.). The reaction mixture was allowed to proceed through a palladium on carbon cartridge and the contents collected and concentrated under reduced pressure. The resulting title compound (I-8b) was carried on to the next reaction without further purification.

$^1$H NMR (500 MHz, Chloroform-d) δ ppm 0.91 (d, J=6.74 Hz, 6H), 1.52 (s, 12H), 2.27 (s, 3H), 3.21 (d, J=36.29 Hz, 2H), 4.45 (s, 2H), 7.01 (d, J=8.03 Hz, 2H), 7.12 (s, 2H), 7.15-7.19 (m, 1H), 7.22 (d, J=8.29 Hz, 2H).

Preparation of Intermediate (4'-Methanesulfonylamino-2-methyl-biphenyl-4-ylmethyl)-(3-methyl-butyl)-carbamic acid tert-butyl ester (I-8c)

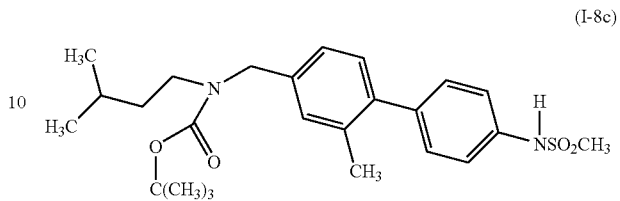
(I-8c)

(4'-Amino-2-methyl-biphenyl-4-ylmethyl)-(3-methyl-butyl)-carbamic acid tert-butyl ester, (I-9b: 128 mg, 0.335 mmol) was dissolved in 7 ml of dichloromethane and treated with triethylamine (0.188 mL, 1.34 mmol) and methylsulfonyl chloride (0.077 mL, 1.0 mmol). After 12 hours, the volatiles were removed under reduced pressure and the residue was then dissolved in methanol (15 mL) and treated with a 2N sodium hydroxide solution (15 mL). After stirring at 50° C. for 1 hour, the reaction mixture was then concentrated under reduced pressure and residue dissolved in ethyl acetate and extracted with water. The organic layer was washed with brine, dried over sodium sulfate, filtered and concentrated under reduced pressure. The residue was purified using preparative thin layer chromatography eluting with 65% ethyl acetate in heptane to afford the title compound (I-8c).

$^1$H NMR (400 MHz, Chloroform-d) δ ppm 0.88 (d, J=6.64 Hz, 6H), 1.31-1.52 (m, 12H), 2.24 (s, 3H), 3.06 (s, 3H), 3.19 (d, J=31.35 Hz, 2H), 4.42 (s, 2H), 6.35 (s, 1H), 7.09 (s, 2H), 7.12-7.15 (m, 1H), 7.22-7.24 (m, 2H), 7.27-7.32 (m, 2H). Mass Spec.: (m/z+1=461)

Example 1

Preparation of 3',5'Difluoro-2-methyl-4'-[(3-methyl-butylamino)-methyl]-biphenyl-4-carboxylic acid amide hydrochloride salt (E1-01)

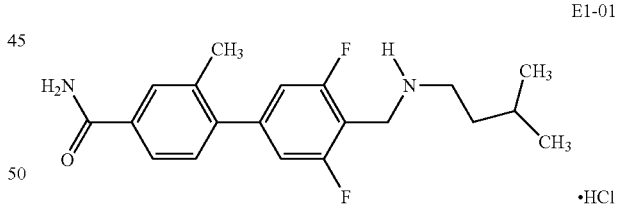
E1-01
•HCl (4'-Carbamoyl-3,5-difluoro-2'-methyl-biphenyl-4-ylmethyl)-(3-methyl-butyl)-carbamic acid tert-butyl ester (I-1e: 40 g) was dissolved in 500 mL of dichloromethane and treated with 34 ml of a 4.0 M hydrogen chloride solution in dioxane. After stirring overnight at room temperature, the volatiles were removed under reduced pressure and the resulting crude material was suspended in ethanol (200 mL), heated at reflux for 20 minutes and stirred overnight at room temperature. The resulting slurry was collect via filtration, rinsing with chilled ethanol, and dried under vacuum to provide the title compound (E1-01: 25 g).

$^1$H NMR (CD$_3$OD): 0.98 (d, 6H, J=6.6 Hz), 1.6-1.8 (m, 3H), 2.32 (s, 3H), 3.10-3.2 (m, 2H), 4.39 (s, 2H), 7.17 (d, 2H, J=8.3 Hz), 7.31 (d, 1H, J=7.9 Hz), 7.76 (d, 1H, J=7.9 Hz), 7.83 (s, 1H). MS: 347 (M+1).

Preparation of 3',5-Difluoro-2-methyl-4'-[(3-methyl-butylamino)-methyl]-biphenyl-4-carboxylic acid amide hydrochloride monohydrate (E1-02)

3',5'-Difluoro-2-methyl-4'-[(3-methyl-butylamino)-methyl]-biphenyl-4-carboxylic acid amide hydrochloride (E1-01: 1 g) was dissolved in 10 mL of anhydrous ethanol with heating. After the solid was dissolved, the heating was discontinued and the solution was stirred as 10 mL of water was added. While stirring for 24 hours at ambient temperature, a precipitate was formed that was collected by filtration and air dried to afford the title compound (E1-02) as a colorless solid.

m.p.=229° C.; Analysis calculated for $C_{20}H_{24}F_2N_2O$—$HCl.H_2O$: C, 59.92; H, 6.79; N, 6.99; Cl, 8.84; F, 9.48. Found: C, 59.97; H, 6.82; N, 6.80; Cl, 8.97; F, 9.65.

The compounds listed in Tables 1A and 1B below were prepared using procedures analogous to those described above for the synthesis of 3',5'-difluoro-2-methyl-4'-[(3-methyl-butylamino)-methyl]-biphenyl-4-carboxylic acid amide hydrochloride salt (E1-01) using the appropriate starting materials which are available commercially, prepared using preparations well-known to those skilled in the art, or prepared in a manner analogous to routes described above for other intermediates.

TABLE 1A

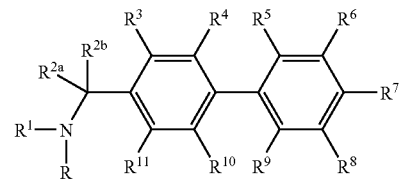

| Comp. No. | R | $R^1$ | $R^{2a}$ $R^{2b}$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|
| 1A-01[2] | H | $(CH_3)_2CH(CH_2)_2$— | H | H | H | H | H | H | —C(O)NH$_2$ | H | CH$_3$ | H |

$^1$H NMR (400 MHz, Methanol-d4) δ ppm 0.97 (d, J = 6.44 Hz, 6 H), 1.57-1.64 (m, 2 H), 1.66-1.71 (m, 1 H), 2.29 (s, 3 H), 3.05-3.11 (m, 2 H), 4.20 (s, 2 H), 7.30-7.34 (m, 1 H), 7.35-7.39 (m, 1 H), 7.42 (s, 1 H), 7.49 (dt, J = 7.68, 1.56 Hz, 1 H), 7.54 (t, J = 7.58 Hz, 1 H), 7.81 (t, J = 1.56 Hz, 1 H), 7.87 (dt, J = 7.68, 1.58 Hz, 1 H).
Mass Spec.: (m/z + 1 = 311)

| 1A-02[2] | H | $(CH_3)_2CH(CH_2)_2$— | H | H | CH$_3$ | H | H | H | —C(O)NH$_2$ | H | CH$_3$ | H |

$^1$H NMR (400 MHz, Methanol-d4) δ ppm 0.97 (d, J = 6.44 Hz, 6 H), 1.57-1.63 (m, 2 H), 1.65-1.71 (m, 1 H), 2.04 (s, 6 H), 3.04-3.10 (m, 2 H), 4.15 (s, 2 H), 7.24 (s, 2 H), 7.29 (dt, J = 7.53, 1.43 Hz, 1 H), 7.57 (t, J = 7.68 Hz, 1 H), 7.62 (t, J = 1.76 Hz, 1 H), 7.89 (dt, J = 7.89, 1.45 Hz, 1 H).
Mass Spec.: (m/z + 1 = 325)

| 1A-03[2] | H | $(CH_3)_2CH(CH_2)_2$— | H | H | Cl | H | H | H | —C(O)NH$_2$ | H | Cl | H |

$^1$H NMR (400 MHz, Methanol-d4) δ ppm 0.98 (d, J = 6.44 Hz, 6 H), 1.58-1.65 (m, 2 H), 1.65-1.74 (m, 1 H), 3.08-3.13 (m, 2 H), 4.24 (s, 2 H), 7.41 (ddd, J = 7.99, 1.45, 1.14 Hz, 1 H), 7.59 (t, J = 7.79 Hz, 1 H), 7.68 (s, 2 H), 7.76 (t, J = 1.56 Hz, 1 H), 7.94-7.97 (m, 1 H).
Mass Spec.: (m/z + 1 = 365)

| 1A-04[2] | H | $(CH_3)_2CH(CH_2)_2$— | H | H | H | H | H | H | —C(O)NH$_2$ | H | CN | H |

$^1$H NMR (400 MHz, METHANOL-d4) δ ppm 0.98 (d, J = 6.44 Hz, 6 H), 1.58-1.67 (m, 2 H), 1.70 (dd, J = 12.98, 6.54 Hz, 1 H), 3.07-3.16 (m, 2 H), 4.33 (s, 2 H), 7.63 (t, J = 7.79 Hz, 1 H), 7.74 (d, J = 8.10 Hz, 1 H), 7.77-7.81 (m, 1 H), 7.91 (dd, J = 8.10, 2.08 Hz, 1 H), 7.99 (ddd, J = 7.79, 1.45, 1.35 Hz, 1 H), 8.03 (d, J = 1.66 Hz, 1 H), 8.08 (t, J = 1.56 Hz, 1 H).
Mass Spec.: (m/z + 1 = 322)

| 1A-05[2] | H | $(CH_3)_2CH(CH_2)_2$— | H | H | H | H | H | H | —C(O)NH$_2$ | H | H | OCH$_3$ |

$^1$H NMR (400 MHz, Methanol-d4) δ ppm 0.97 (d, J = 6.44 Hz, 6 H), 1.58-1.70 (m, 3 H), 3.04-3.11 (m, 3 H), 4.02 (s, 3 H), 4.24 (s, 2 H), 7.33-7.35 (m, 1 H), 7.38 (d, J = 1.66 Hz, 1 H), 7.47 (d, J = 7.89 Hz, 1 H), 7.56 (t, J = 7.68 Hz, 1 H), 7.83-7.89 (m, 2 H), 8.16 (t, J = 1.87 Hz, 1 H).
Mass Spec.: (m/z + 1 = 327)

| 1A-06[2] | H | $(CH_3)_2CH(CH_2)_2$— | H | H | H | H | H | H | —C(O)NH$_2$ | H | H | OH |

$^1$H NMR (400 MHz, Methanol-d4) δ ppm 0.96 (d, J = 6.44 Hz, 6 H), 1.58-1.70 (m, 3 H), 3.03-3.08 (m, 2 H), 4.23 (s, 2 H), 7.19 (d, J = 1.87 Hz, 1 H), 7.22 (dd, J = 7.89, 1.87 Hz, 1 H), 7.41 (d, J = 7.68 Hz, 1 H), 7.54 (t, J = 7.79 Hz, 1 H), 7.75-7.79 (m, 1 H), 7.85 (ddd, J = 7.79, 1.45, 1.35 Hz, 1 H), 8.10 (t, J = 1.66 Hz, 1 H).
Mass Spec.: (m/z + 1 = 313)

| 1A-07[2] | H | $(CH_3)_2CH(CH_2)_2$— | H | H | H | F | H | H | —C(O)NH$_2$ | H | F | H |

$^1$H NMR (400 MHz, methanol-d4) δ ppm 0.98 (d, J = 6.44 Hz, 6 H), 1.58-1.65 (m, 2 H), 1.70 (dt, J = 13.24, 6.57 Hz, 1 H), 3.08-3.14 (m, 2 H), 4.28 (s, 2 H), 7.29-7.35 (m, 1 H), 7.40-7.46 (m, 2 H), 7.57 (t, J = 7.79 Hz, 1 H), 7.95-8.01 (m, 2 H).
Mass Spec.: (m/z + 1 = 333)

TABLE 1A-continued

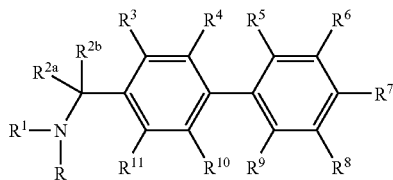

| Comp. No. | R | $R^1$ | $R^{2a}$ $R^{2b}$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|
| 1A-08[2] | H | $(CH_3)_2CH(CH_2)_2$— | H H | H | F | H | H | H | —C(O)NH$_2$ | H | F | H |

$^1$H NMR (400 MHz, Methanol-d4) δ ppm 0.97 (d, J = 6.44 Hz, 6 H), 1.60-1.67 (m, 2 H), 1.67-1.75 (m, J = 13.19, 6.54, 6.44 Hz, 1 H), 3.11-3.18 (m, 2 H), 4.38 (s, 2 H), 7.52 (d, J = 8.93 Hz, 2 H), 7.60 (t, J = 7.79 Hz, 1 H), 7.88 (ddd, J = 7.73, 1.92, 1.14 Hz, 1 H), 7.94 (dt, J = 7.73, 1.43 Hz, 1 H), 8.18 (t, J = 1.66 Hz, 1 H).
Mass Spec.: (m/z + 1 = 333)

| 1A-09[2] | H | $(CH_3)_2CH(CH_2)_2$— | H H | H | F | H | F | H | H | —C(O)NH$_2$ | H | F | H |

$^1$H NMR (400 MHz, Methanol-d4) δ ppm 0.98 (d, J = 6.44 Hz, 6 H), 1.58-1.66 (m, 2 H), 1.71 (ddd, J = 13.19, 6.54, 6.44 Hz, 1 H), 3.10-3.19 (m, 2 H), 4.39 (s, 2 H), 7.35 (dd, J = 10.49, 8.62 Hz, 1 H), 7.44 (d, J = 7.89 Hz, 2 H), 7.99 (ddd, J = 8.67, 4.72, 2.39 Hz, 1 H), 8.09 (dd, J = 7.37, 2.39 Hz, 1 H).
Mass Spec.: (m/z + 1 = 351)

| 1A-10[2] | H | (2-indanyl) | H H | H | F | H | H | H | —C(O)NH$_2$ | H | H | F |

$^1$H NMR (400 MHz, Methanol-d4) δ ppm 3.22 (dd, J = 16.30, 6.33 Hz, 2 H), 3.53 (dd, J = 16.40, 7.89 Hz, 2 H), 4.21-4.29 (m, 1 H), 4.46 (s, 2 H), 7.20-7.25 (m, 2 H), 7.29 (ddd, J = 8.82, 3.63, 3.53 Hz, 2 H), 7.51-7.56 (m, 2 H), 7.60 (t, J = 7.79 Hz, 1 H), 7.88 (ddd, J = 7.79, 1.97, 1.04 Hz, 1 H), 7.94 (dt, J = 7.68, 1.35 Hz, 1 H), 8.18 (t, J = 1.56 Hz, 1 H).
Mass Spec.: (m/z + 1 = 379)

| 1A-11[2] | H | (2-indanyl) | H H | H | F | H | F | H | H | —C(O)NH$_2$ | H | H | F |

$^1$H NMR (400 MHz, Methanol-d4) δ ppm 3.21 (dd, J = 16.30, 6.13 Hz, 2 H), 3.53 (dd, J = 16.51, 7.99 Hz, 2 H), 4.22-4.29 (m, J = 7.11, 7.11, 7.11, 7.11 Hz, 1 H), 4.47 (s, 2 H), 7.21-7.25 (m, 2 H), 7.27-7.31 (m, 2 H),, 7.35 (dd, J = 10.59, 8.72 Hz, 2 H), 7.45 (d, J = 7.89 Hz, 2 H), 7.98 (ddd, J = 8.57, 4.72, 2.28 Hz, 1 H), 8.09 (dd, J = 7.48, 2.28 Hz, 1 H).
Mass Spec.: (m/z + 1 = 397)

| 1A-12[2] | H | $(CH_3)_2CH(CH_2)_2$— | H H | H | H | H | F | H | H | —C(O)NH$_2$ | H | H | F |

$^1$H NMR (400 MHz, Methanol-d4) δ ppm 0.97 (d, J = 6.44 Hz, 6 H), 1.59-1.67 (m, 2 H), 1.68-1.72 (m, 1 H), 3.10-3.15 (m, 2 H), 4.34 (s, 2 H), 7.33 (dd, J = 10.49, 8.62 Hz, 1 H), 7.50-7.56 (m, 2 H), 7.64-7.70 (m, 1 H), 7.95 (ddd, J = 8.57, 4.72, 2.28 Hz, 1 H), 8.06 (dd, J = 7.37, 2.39 Hz, 1 H).
Mass Spec.: (m/z + 1 = 333)

| 1A-13[2] | H | $(CH_3)_2CH(CH_2)_2$— | H H | H | H | H | H | H | H | —C(O)NH$_2$ | H | H | Cl |

$^1$H NMR (500 MHz, Methanol-d4) δ ppm 1.02 (d, J = 6.22 Hz, 6 H), 1.65-1.70 (m, 2 H), 1.72-1.76 (m, 1 H), 3.17-3.22 (m, 2 H), 4.45 (s, 2 H), 7.62 (t, J = 7.78 Hz, 1 H), 7.72 (d, J = 8.03 Hz, 1 H), 7.79 (dd, J = 7.91, 1.43 Hz, 1 H), 7.88 (d, J = 7.78 Hz, 1 H), 7.91-7.96 (m, 2 H) 8.20 (s, 1 H).
Mass Spec.: (m/z + 1 = 331)

[1]Isolated and characterized as the free base.
[2]Isolated and characterized as the hydrochloride salt.
[3]Isolated and characterized as the trifluoroacetic acid salt.

TABLE 1B

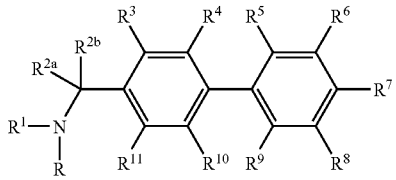

| Comp. No. | R | $R^1$ | $R^{2a}$ $R^{2b}$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|
| 1B-01[2] | H | $(CH_3)_2CH(CH_2)_2-$ | H H | H | H | H | H | $-C(O)NH_2$ | H | H | $CH_3$ | H |

$^1$H NMR (400 MHz, methanol-d4) δ ppm 0.97 (d, J = 6.64 Hz, 6 H), 1.57-1.63 (m, 2 H), 1.65-1.72 (m, 1 H), 2.29 (s, 3 H), 3.05-3.12 (m, 2 H), 4.20 (s, 2 H), 7.31 (d, J = 7.89 Hz, 1 H), 7.36 (d, J = 1.45 Hz, 1 H), 7.40 (ddd, J = 8.41, 1.87, 1.77 Hz, 2 H), 7.42 (d, J = 1.04 Hz, 1 H), 7.94 (dt, J = 8.31, 1.87 Hz, 2 H).
Mass Spec.: (m/z + 1 = 311)

| 1B-02[2] | H | $(CH_3)_2CH(CH_2)_2-$ | H H | H | H | H | H | $-C(O)NH_2$ | H | H | F | H |

$^1$H NMR (400 MHz, Methanol-d4) δ ppm 0.98 (d, J = 6.64 Hz, 6 H), 1.58-1.64 (m, 2 H), 1.66-1.72 (m, 1 H), 3.07-3.12 (m, 2 H), 4.26 (s, 2 H), 7.39-7.43 (m, 2 H), 7.62-7.68 (m, 3 H), 7.97 (ddd, J = 8.62, 1.97, 1.87 Hz, 2 H).
Mass Spec.: (m/z + 1 = 311)

| 1B-03[2] | H | $(CH_3)_2CH(CH_2)_2-$ | H H | H | H | $CH_3$ | H | $-C(O)NH_2$ | H | H | F | H |

$^1$H NMR (400 MHz, Methanol-d4) δ ppm 0.98 (d, J = 6.44 Hz, 6 H), 1.58-1.65 (m, 2 H), 1.67-1.74 (m, 1 H), 2.21 (s, 3 H), 3.09-3.14 (m, 2 H), 4.27 (s, 2 H), 7.27 (d, J = 7.89 Hz, 1 H), 7.37-7.43 (m, 3 H), 7.75 (dd, J = 8.10, 1.87 Hz, 1 H), 7.82 (d, J = 1.25 Hz, 1 H).
Mass Spec.: (m/z + 1 = 329)

| 1B-04[2] | H | (2-indanyl) | H H | H | F | H | H | $-C(O)NH_2$ | H | $CH_3$ | F | H |

$^1$H NMR (400 MHz, Methanol-d4) δ ppm 2.20 (s, 3 H), 3.18 (dd, J = 16.30, 5.09 Hz, 2 H), 3.48 (dd, J = 16.20, 6.64 Hz, 2 H), 4.15-4.24 (m, J = 5.61 Hz, 1 H), 4.39 (s, 2 H), 7.18-7.23 (m, 2 H), 7.24-7.29 (m, 2 H), 7.31 (d, J = 7.68 Hz, 2 H), 7.70 (d, J = 6.23 Hz, 1 H), 7.76 (d, J = 7.68 Hz, 1 H), 7.85 (s, 1 H).
Mass Spec.: (m/z + 1 = 393)

| 1B-05[2] | H | $(CH_3)_2CH(CH_2)_2-$ | H H | H | F | H | H | $-C(O)NH_2$ | H | H | H | F |

$^1$H NMR (400 MHz, Methanol-d4) δ ppm 0.97 (d, J = 6.23 Hz, 6 H), 1.61-1.68 (m, 2 H), 1.68-1.75 (m, 1 H), 3.11-3.18 (m, 2 H), 4.38 (s, 2 H), 7.51 (d, J = 8.93 Hz, 2 H), 7.79 (d, J = 8.51 Hz, 2 H), 7.99 (d, J = 8.72 Hz, 2 H).
Mass Spec.: (m/z + 1 = 333)

| 1A-06[2] | H | (2-indanyl) | H H | H | H | H | $CH_3$ | H | $-C(O)NH_2$ | H | H | F | H |

$^1$H NMR (400 MHz, Methanol-d4) δ ppm 2.21 (s, 3 H), 3.21 (dd, J = 16.51, 6.54 Hz, 2 H), 3.49 (dd, J = 16.20, 7.89 Hz, 2 H), 4.16-4.23 (m, 1 H), 4.38 (s, 2 H), 7.21-7.31 (m, 5 H), 7.38-7.47 (m, 3 H), 7.75 (dd, J = 7.99, 1.56 Hz, 1 H), 7.82 (s, 1 H).
Mass Spec.: (m/z + 1 = 375)

| 1A-07[2] | H | (2-indanyl) | H H | H | F | H | $CH_3$ | H | $-C(O)NH_2$ | H | H | H | F |

$^1$H NMR (400 MHz, Methanol-d4) δ ppm 2.32 (s, 3 H), 3.22 (dd, J = 16.40, 6.44 Hz, 2 H), 3.53 (dd, J = 16.30, 7.99 Hz, 2 H), 4.22-4.30 (m, J = 7.11, 7.11, 7.11, 7.11 Hz, 1 H), 4.47 (s, 2 H), 7.15-7.20 (m, 2 H), 7.21-7.25 (m, 2 H), 7.28-7.33 (m, 3 H), 7.76 (dd, J = 8.31, 1.66 Hz, 1 H) 7.83 (s, 1 H).
Mass Spec.: (m/z + 1 = 393)

| 1B-08[2] | H | $(CH_3)_2CH(CH_2)_2-$ | H H | H | H | H | $CH_3$ | $-C(O)NH_2$ | H | H | H | F |

$^1$H NMR (400 MHz, Methanol-d4) δ ppm 0.98 (d, J = 6.44 Hz, 6 H), 1.60-1.67 (m, 2 H), 1.68-1.72 (m, 1 H), 2.30 (s, 3 H), 3.11-3.16 (m, 2 H), 4.34 (s, 2 H), 7.24-7.31 (m, 3 H), 7.63 (t, J = 7.79 Hz, 1 H), 7.75 (dd, J = 7.89, 1.87 Hz, 1 H), 7.82 (d, J = 1.87 Hz, 1 H).
Mass Spec.: (m/z + 1 = 328)

| 1B-09[2] | H | $CH_3O(CH_2)_2-$ | H H | H | F | H | $CH_3$ | $-C(O)NH_2$ | H | H | H | F |

TABLE 1B-continued

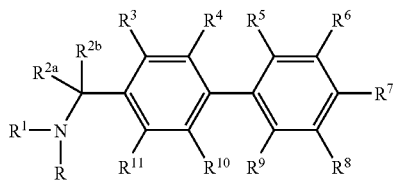

| Comp. No. | R | R¹ | $R^{2a}$ $R^{2b}$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|

¹H NMR (400 MHz, Chloroform-d) δ ppm 2.30 (s, 3 H), 2.82 (t, J = 5.19 Hz, 2 H), 3.34 (s, 3 H), 3.51 (t, J = 5.40 Hz, 2 H), 3.94 (s, 2 H), 5.82 (s, 1 H), 6.13 (s, 1 H) 6.80-6.87 (m, 2 H), 7.22-7.27 (m, 1 H), 7.63 (dd, J = 7.89, 1.66 Hz, 1 H), 7.74 (d, J = 1.25 Hz, 1 H).
Mass Spec.: (m/z + 1 = 335)

| 1B-10² | H | 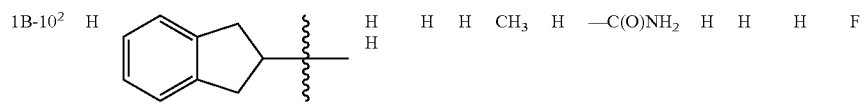 | H H | H | H | $CH_3$ | H | $-C(O)NH_2$ | H | H | H | F |

¹H NMR (400 MHz, Methanol-d4) δ ppm 2.30 (s, 3 H), 3.19 (dd, J = 6.20, 6.64 Hz, 2 H), 3.51 (dd, J = 16.30, 7.99 Hz, 2 H), 4.17-4.25 (m, 1 H), 4.42 (s, 2 H), 7.21-7.25 (m, 2 H), 7.26-7.32 (m, 5 H), 7.65 (t, J = 7.79 Hz, 1 H), 7.75 (dd, J = 7.89, 1.87 Hz, 1 H), 7.82 (d, J = 1.87 Hz, 1 H).
Mass Spec.: (m/z + 1 = 375)

[1] Isolated and characterized as the free base.
[2] Isolated and characterized as the hydrochloride salt.
[3] Isolated and characterized as the trifluoroacetic acid salt.
"Et" refers to ethyl and "OBn" refers to benzyloxy.

TABLE 1C

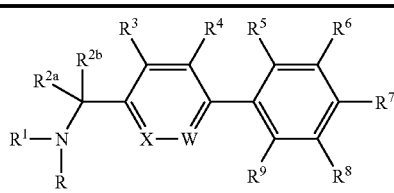

| Comp. No. | R | R¹ | $R^{2a}$ $R^{2b}$ | $R^3$ | $R^4$ | $R^5$ | $R^6$ | $R^7$ | $R^8$ | $R^9$ | W | X |
|---|---|---|---|---|---|---|---|---|---|---|---|---|
| 1C-01² | H | $(CH_3)_2CH(CH_2)_2-$ | H H | H | H | H | H | H | $-C(O)NH_2$ | H | C—H | N |

¹H NMR (400 MHz, Methanol-d4) δ ppm 0.99 (d, J = 6.23 Hz, 6 H), 1.63-1.75 (m, 3 H), 3.11-3.21 (m, 2 H), 4.46 (s, 2 H), 7.60-7.67 (m, 2 H), 7.88-7.91 (m, 1 H), 7.95 (dt, J = 7.73, 1.43 Hz, 1 H), 8.21 (t, J = 1.87 Hz, 1 H), 8.28 (dd, J = 8.10, 2.28 Hz, 1 H), 9.01 (d, J = 2.28 Hz, 1 H).
Mass Spec.: (m/z + 1 = 298)

[2] Isolated and characterized as the hydrochloride salt.

TABLE 1D

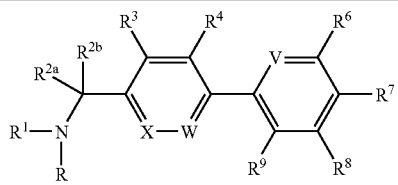

| Comp. No. | R | R¹ | $R^{2a}$ $R^{2b}$ | $R^3$ | $R^4$ | V | $R^6$ | $R^7$ | $R^8$ | $R^9$ | W | X |
|---|---|---|---|---|---|---|---|---|---|---|---|---|
| 1D-01² | H | $(CH_3)_2CH(CH_2)_2-$ | H H | H | H | C—$CH_3$ | H | $-C(O)NH_2$ | H | H | C—H | N |

¹H NMR (400 MHz, Methanol-d4) δ ppm 0.99 (d, J = 6.23 Hz, 6 H), 1.63-1.76 (m, 3 H), 2.32 (s, 3 H), 3.14-3.20 (m, 2 H), 4.46 (s, 2 H), 7.34 (d, J = 7.89 Hz, 1 H), 7.61 (d, J = 8.10 Hz, 1 H), TABLE 1D-continued

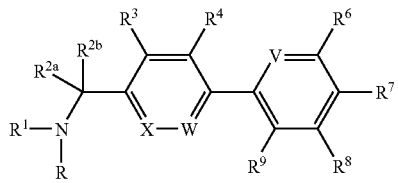

| Comp. No. | R | $R^1$ | $R^{2a}$ $R^{2b}$ | $R^3$ | $R^4$ | V | $R^6$ | $R^7$ | $R^8$ | $R^9$ | W | X |
|---|---|---|---|---|---|---|---|---|---|---|---|---|
| | | 7.79 (dd, J = 7.89, 1.87 Hz, 1 H), 7.86 (d, J = 1.87 Hz, 1 H), 7.94 (td, J = 5.29, 2.49 Hz, 1 H), 8.66-8.68 (m, 1 H). Mass Spec.: (m/z + 1 = 312) | | | | | | | | | | |
| 1D-02[2] | H | $(CH_3)_2CH(CH_2)_2$— | H H | H | H | C—$CH_3$ | H | —C(O)$NH_2$ | H | H | N | C—H |
| | | $^1$H NMR (400 MHz, Methanol-d4) δ ppm 1.00 (d, J = 6.44 Hz, 6 H), 1.62-1.75 (m, 3 H), 2.40 (s, 3 H), 3.18-3.23 (m, 2 H), 4.50 (s, 2 H), 7.58 (d, J = 8.10 Hz, 1 H), 7.89 (d, J = 8.31 Hz, 1 H), 7.94 (s, 1 H), 8.11 (d, J = 8.51 Hz, 1 H), 8.63 (dd, J = 8.31, 1.87 Hz, 1 H), 9.05 (s, 1 H). Mass Spec.: (m/z + 1 = 312) | | | | | | | | | | |
| 1D-03[2] | H | (indan-2-yl) | H H | H | H | C—$CH_3$ | H | —C(O)$NH_2$ | H | H | N | C—H |
| | | $^1$H NMR (400 MHz, Methanol-d4) δ ppm 2.40 (s, 3 H), 3.25-3.33 (m, 2 H), 3.53 (dd, J = 16.40, 7.68 Hz, 3 H), 4.24-4.31 (m, 1 H), 4.59 (s, 2 H), 7.22-7.27 (m, 3 H), 7.31 (dd, J = 5.29, 3.22 Hz, 2 H), 7.56 (d, J = 8.10 Hz, 1 H), 7.88 (dd, J = 8.10, 1.66 Hz, 1 H), 7.93 (s, 1 H), 8.06 (d, J = 8.31 Hz, 1 H), 8.59 (dd, J = 8.20, 2.18 Hz, 1 H), 9.06 (d, J = 2.08 Hz, 1 H). Mass Spec.: (m/z + 1 = 358) | | | | | | | | | | |
| 1D-04[2] | H | (indan-2-yl) | H H | H | H | C—$CH_3$ | H | —C(O)$NH_2$ | H | H | C—H | N |
| | | $^1$H NMR (500 MHz, Methanol-d4) δ ppm 2.35 (s, 3 H), 3.27 (dd, J = 16.07, 6.74 Hz, 2 H), 3.52 (dd, J = 6.33, 8.03 Hz, 2 H), 4.27 (t, J = 7.26 Hz, 1 H), 4.56 (s, 2 H), 7.24-7.28 (m, 2 H), 7.32 (dd, J = 5.05, 3.50 Hz, 2 H), 7.36 (d, J = 8.03 Hz, 1 H), 7.63 (d, J = 8.03 Hz, 1 H), 7.82 (dd, J = 7.90, 1.43 Hz, 1 H), 7.88 (s, 1 H), 7.93 (dd, J = 8.03, 2.33 Hz, 1 H), 8.68 (d, J = 1.81 Hz, 1 H). Mass Spec.: (m/z + 1 = 358) | | | | | | | | | | |
| 1D-05[2] | H | (indan-2-yl) | H H | H | H | C—H | H | —C(O)$NH_2$ | H | Cl | C—H | N |
| | | NMR is inconsistent Mass Spec.: (m/z + 1 = 378) | | | | | | | | | | |
| 1D-06[2] | H | (indan-2-yl) | H H | H | H | C—H | H | —C(O)$NH_2$ | H | Cl | N | C—H |
| | | $^1$H NMR (400 MHz, METHANOL-d4) δ ppm 3.27-3.33 (m, 2 H) 3.53 (dd, J = 16.40, 7.68 Hz, 2 H) 4.28 (t, J = 7.27 Hz, 1 H) 4.60 (s, 2 H) 7.21-7.26 (m, 2 H) 7.28-7.37 (m, 2 H) 7.76 (d, J = 7.89 Hz, 1 H) 8.01 (d, J = 8.10 Hz, 1 H) 8.13 (s, 2 H) 8.60 (d, J = 7.06 Hz, 1 H) 9.10 (s, 1 H). Mass Spec.: (m/z + 1 = 378) | | | | | | | | | | |
| 1D-07[2] | H | $(CH_3)_2CH(CH_2)_2$— | H H | H | $CH_3$ | N | H | —C(O)NH2 | H | $CH_3$ | C—H | C—H |
| | | $^1$H NMR (400 MHz, Methanol-d4) δ ppm 0.98 (d, J = 6.44 Hz, 6 H), 1.60-1.72 (m, 3 H), 2.19 (s, 3 H), 2.31 (s, 3 H), 3.09-3.14 (m, 2 H), 4.30 (s, 2 H), 7.50 (d, J = 7.68 Hz, 1 H), 7.59 (dd, J = 7.99, 1.35 Hz, 1 H), 7.64 (s, 1 H), 8.90 (d, J = 1.25 Hz, 1 H), 9.12 (d, J = 2.08 Hz, 1 H). Mass Spec.: (m/z + 1 = 326) | | | | | | | | | | |

[1]Isolated and characterized as the free base.
[2]Isolated and characterized as the hydrochloride salt.
[3]Isolated and characterized as the trifluoroacetic acid salt.

Example 2

Preparation of 2,2'-Dimethyl-4'-[(3-methyl-butylamino)-methyl]-biphenyl-4-carboxylic acid amide hydrochloride salt (E2-01)

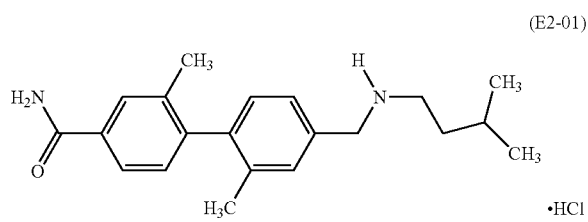

(E2-01)

(4'-Carbamoyl-2',2-dimethyl-biphenyl-4-ylmethyl)-(3-methyl-butyl)-carbamic acid tert-butyl ester (I-2e: 12 g, 28.3 mmol) was dissolved in ethyl acetate and treated with 20 mL of 4.0 M hydrogen chloride in dioxane. After stirring overnight at room temperature, the volatiles were removed under reduced pressure and the resulting crude material dissolved in methanol and then ethyl acetate was added to precipitate a white solid that was isolated via filtration. This solid was suspended in iso-propanol (1 g: 20 mL), heated at reflux for 20 minutes and stirred overnight at room temperature. The resulting slurry was collect via filtration, rinsing with chilled iso-propanol, and dried under vacuum to provide the title compound (E2-01).

$^1$H NMR (CD$_3$OD): δ 0.97 (d, 6H, J=6.6 Hz), 1.6-1.8 (m, 3H), 2.06 (s, 3H), 2.07 (s, 3H), 3.05-3.15 (m, 2H), 4.21 (s, 2H), 7.13 (d, 1H, J=7.9 Hz), 7.17 (d, 1H, J=7.9 Hz), 7.38 (d, 1H, J=7.9 Hz), 7.45 (s, 1H), 7.74 (d, 1H, J=7.9 Hz), 7.82 (s, 1H). MS: 325 (M+1)

Example 3

Preparation of 3-Chloro-2-methyl-4'-[(3-methyl-butylamino)-methyl]-biphenyl-4-carboxylic acid amide hydrochloride salt (E3-01)

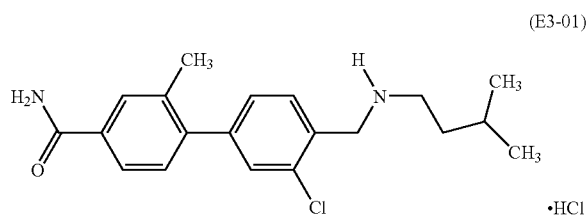

(E3-01)

(4'-Carbamoyl-3-chloro-2'-methyl-biphenyl-4-ylmethyl)-(3-methyl-butyl)-carbamic acid tert-butyl ester (I-3e: 12.6 g, 28.3 mmol) was dissolved in ethyl acetate and treated with 30 ml of 4.0M hydrogen chloride in dioxane. After stirring for 24 hours at room temperature, the volatiles were removed under reduced pressure and the product was isolated by dissolving the crude material in methanol and slowly adding ethyl acetate to precipitate the product, which was isolated via filtration. The solid was crystallized by dissolving in 10 parts of hot ethanol before cooling to room temperature. After stirring for 48 hours, the resulting slurry was collected via filtration, rinsing with chilled ethanol, to provide the title compound (E3-01) as a colorless solid.

$^1$H NMR (CD$_3$OD): δ 0.99 (d, 6H, J=6.2 Hz), 1.6-1.8 (m, 3H), 2.29 (s, 3H), 3.15-3.30 (m, 2H), 4.43 (s, 2H), 7.28 (d, 1H, J=7.9 Hz), 7.41 (d, 1H, J=7.9 Hz), 7.55 (s, 1H), 7.68 (d, 1H, J=7.9 Hz), 7.75 (d, 1H, J=7.9), 7.82 (s, 1H). MS: 345 (M+1)

Example 4

Preparation of 2-Methyl-4'-[(3-methyl-butylamino)-methyl]-biphenyl-4-carboxylic acid amide (E4-01)

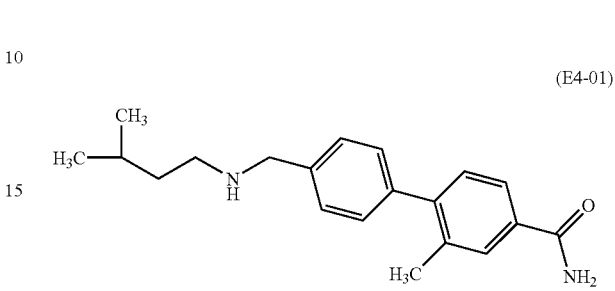

(E4-01)

4'-Formyl-2-methylbiphenyl-4-carboxamide (I-4a: 4.3 g, 18.0 mmol) and isoamylamine (36.2 mg, 0.425 mmol) were combined in methanol (100 ml). After 12 hours, the reaction mixture was treated with sodium borohydride (2.10 g, 53.9 mmol). After 1 hour, the reaction mixture was treated with concentrated (37%) aqueous hydrochloric acid solution and the volatiles were removed under reduced pressure. The residue was taken up in 2N sodium hydroxide and extracted with ethyl acetate (2 times). The combined organic phases were washed with a saturated aqueous sodium bicarbonate solution, dried over sodium sulfate, filtered and concentrated under reduced pressure to provide the title compound (E4-01).

$^1$H NMR (400 MHz, Chloroform-d) δ ppm 0.90 (d, J=6.64 Hz, 6H), 1.36-1.47 (m, 2H), 1.65 (dt, J=13.44, 6.67 Hz, 1H), 2.31 (s, 3H), 2.63-2.71 (m, 2H), 3.83 (s, 2H), 5.61 (s, 1H), 6.11 (s, 1H), 7.26 (d, J=8.51 Hz, 2H), 7.29 (d, J=8.10 Hz, 1H), 7.38 (d, J=8.31 Hz, 2H), 7.63 (dd, J=7.68, 1.66 Hz, 1H), 7.74 (d, J=1.87 Hz, 1H).

Mass Spec.: (m/z+1=311)

Conversion to the ammonium salt—(4'-carbamoyl-2'-methyl-biphenyl-4-ylmethyl)-(3-methyl-butyl)-ammonium chloride (E4-02)

(4'-Carbamoyl-2'-methyl-biphenyl-4-ylmethyl)-(3-methyl-butyl)-carbamic acid tert-butyl ester (I-4b: 8.0 g, 23 mmol) was dissolved in methanol (50 mL) and treated with 4M hydrogen chloride in dioxane (10 mL). After stirring for 12 hours, the volatiles were removed under reduced pressure and the resulting solid was titrated with hexanes and isolated by filtration to provide 7.1 g the title compound (E4-02) as a colorless solid.

$^1$H NMR (400 MHz, Methanol-d4) δ ppm 0.97 (d, J=6.44 Hz, 6H), 1.58-1.65 (m, 2H) 1.66-1.71 (m, 1H), 2.28 (s, 3H), 3.08-3.13 (m, 2H), 4.26 (s, 2H), 7.27 (d, J=8.10 Hz, 1H), 7.44 (d, J=8.31 Hz, 2H), 7.58 (d, J=8.31 Hz, 2H), 7.74 (dd, J=7.99, 1.97 Hz, 1H), 7.81 (s, 1H). Mass Spec.: (m/z+1=311)

The compounds listed in Tables 4A and 4B below were prepared using procedures analogous to those described above for the synthesis of 2-Methyl-4'-[(3-methyl-butylamino)-methyl]-biphenyl-4-carboxylic acid amide (E4-01) and (4'-carbamoyl-2'-methyl-biphenyl-4-ylmethyl)-(3-methyl-butyl)-ammonium chloride (E4-02) using the appropriate starting materials which are available commercially, prepared using preparations well-known to those skilled in the art, or prepared in a manner analogous to routes described above for other intermediates.

TABLE 4A

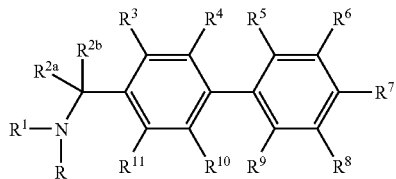

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4A-01[2] | H | (CH₃)₂CH(CH₂)₂— | H | H | H | H | H | H | —C(O)NH₂ | H | H | H |

$^1$H NMR (400 MHz, Methanol-d4) δ ppm 0.97 (d, J = 6.44 Hz, 6 H), 1.57-1.64 (m, 2 H), 1.65-1.71 (m, 1 H), 3.06-3.12 (m, 2 H), 4.25 (s, 2 H), 7.54-7.61 (m, 3 H), 7.77-7.89 (m, 4 H), 8.16 (t, J = 1.76 Hz, 1 H).
Mass Spec.: (m/z + 1 = 297)

| | | | | | | | | | | | | |
|---|---|---|---|---|---|---|---|---|---|---|---|---|
| 4A-02[2] | H | (CH₃)₂CH(CH₂)₂— | H | H | H | H | H | F | —C(O)NH₂ | H | H | H |

$^1$H NMR (400 MHz, Methanol-d4) δ ppm 0.96 (d, J = 6.44 Hz, 6 H), 1.58-1.64 (m, 2 H), 1.68 (dd, J = 13.19, 6.54 Hz, 1 H), 3.05-3.12 (m, 2 H), 4.24 (s, 2 H), 7.32 (dd, J = 10.80, 8.72 Hz, 1 H), 7.59 (d, J = 8.31 Hz, 2 H), 7.73 (d, J = 8.51 Hz, 2 H), 7.82 (ddd, J = 8.62, 4.78, 2.60 Hz, 1 H), 8.06 (dd, J = 6.85, 2.49 Hz, 1 H).
Mass Spec.: (m/z + 1 = 315)

| | | | | | | | | | | | | |
|---|---|---|---|---|---|---|---|---|---|---|---|---|
| 4A-03[2] | H | (indane-2-yl)methyl | H | H | H | H | H | F | —C(O)NH₂ | H | H | H |

$^1$H NMR (400 MHz, Methanol-d4) δ ppm 3.21 (dd J = 16.30, 6.75 Hz, 2 H), 3.47 (dd, J = 16.20, 8.10 Hz, 2 H), 4.17 (t, J = 7.48 Hz, 1 H), 4.35 (s, 2 H), 7.19-7.23 (m, 2 H), 7.25-7.29 (m, 2 H), 7.32 (dd, J = 10.69, 8.62 Hz, 1 H), 7.64 (d, J = 8.31 Hz, 2 H), 7.74 (d, J = 8.51 Hz, 2 H), 7.83 (ddd, J = 8.67, 4.72, 2.60 Hz, 1 H), 8.06 (dd, J = 7.06, 2.49 Hz, 1 H).
Mass Spec.: (m/z + 1 = 361)

| | | | | | | | | | | | | |
|---|---|---|---|---|---|---|---|---|---|---|---|---|
| 4A-04[2] | H | (CH₃)₂CH(CH₂)₂— | H | H | H | H | F | H | —C(O)NH₂ | H | H | H |

$^1$H NMR (400 MHz, Methanol-d4) δ ppm 0.97 (d, J = 6.44 Hz, 6 H), 1.57-1.64 (m, 2 H), 1.65-1.71 (m, 1 H), 3.06-3.12 (m, 2 H), 4.25 (s, 2 H), 7.61 (ddd, J = 1.42, 4.46, 2.39 Hz, 4 H), 7.81 (ddd, J = 8.41, 2.08, 1.97 Hz, 2 H), 8.00 (t, J = 1.56 Hz, 1 H).
Mass Spec.: (m/z + 1 = 315)

| | | | | | | | | | | | | |
|---|---|---|---|---|---|---|---|---|---|---|---|---|
| 4A-05[2] | H | (CH₃)₂CH(CH₂)₂— | H | H | H | Cl | H | H | —C(O)NH₂ | H | H | H |

$^1$H NMR (400 MHz, Methanol-d4) δ ppm 0.98 (d, J = 6.64 Hz, 6 H), 1.58-1.64 (m, 2 H), 1.69 (dd, J = 13.19, 6.75 Hz, 1 H), 3.08-3.13 (m, 2 H), 4.25 (s, 2 H), 7.52 (s, 2 H), 7.55 (t, J = 7.58 Hz, 1 H), 7.61 (dt, J = 7.73, 1.53 Hz, 1 H), 7.71 (s, 1 H), 7.89-7.93 (m, 2 H).

| | | | | | | | | | | | | |
|---|---|---|---|---|---|---|---|---|---|---|---|---|
| 4A-06[1] | H | (tetrahydropyran-3-yl)methyl | H | H | H | Cl | H | H | —C(O)NH₂ | H | H | H |

$^1$H NMR (400 MHz, Methanol-d4) δ ppm 1.18-1.29 (m, 1 H), 1.54-1.64 (m, 2 H), 1.80 (ddd, J = 10.02, 6.59, 3.53 Hz, 1 H), 1.83-1.92 (m, 1 H), 2.43 (d, J = 6.85 Hz, 2 H), 3.15 (dd, J = 11.11, 9.66 Hz, 1 H), 3.33-3.44 (m, 1 H), 3.76 (s, 2 H), 3.81 (ddd, J = 11.11, 3.53, 3.43 Hz, 1 H), 3.90-3.98 (m, 1 H), 7.35 (s, 2 H), 7.49-7.55 (m, 2 H), 7.58-7.63 (m, 1 H), 7.86-7.90 (m, 1 H), 7.91 (t, J = 1.45 Hz, 1 H).
Mass Spec. (m/z + 1 = 359).

| | | | | | | | | | | | | |
|---|---|---|---|---|---|---|---|---|---|---|---|---|
| 4A-07[2] | H | (tetrahydrofuran-2-yl)methyl | H | H | H | Cl | H | H | —C(O)NH₂ | H | H | H |

$^1$H NMR (400 MHz, Methanol-d4) δ ppm 1.57-1.67 (m, 1 H), 1.90-2.00 (m, 2 H), 2.08-2.17 (m, 1 H), 3.01 (dd, J = 12.67, 9.97 Hz, 1 H), 3.21 (dd, J = 12.77, 2.80 Hz, 1 H), 3.78-3.86 (m, 1 H), 3.92 (dt, J = 8.31, 6.75 Hz, 1 H), 4.16-4.23 (m, 1 H), 4.26-4.34 (m, 2 H), 7.49-7.58 (m, 3 H), 7.62 (ddd, J = 7.89, 1.45, 1.25 Hz, 1 H), 7.72 (d, J = 1.45 Hz, 1 H), 7.89-7.91 (m, 1 H), 7.93 (td, J = 3.06, 1.77 Hz, 1 H).
Mass Spec. (m/z + 1 = 345).

TABLE 4A-continued

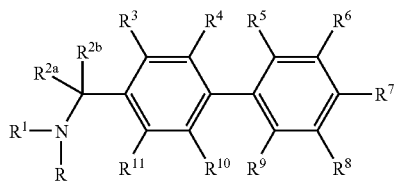

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4A-08[2] | H | ![tetrahydropyranylethyl] | H H | H | Cl | H | H | H | —C(O)NH$_2$ | H | H | H |

$^1$H NMR (400 MHz, Methanol-d4) δ ppm 1.25-1.36 (m, 1 H), 1.61-1.71 (m, 5 H), 3.14 (d, J = 15.78 Hz, 2 H), 3.40 (td, J = 11.78, 1.76 Hz, 2 H), 3.92 (dd, J = 11.01, 3.95 Hz, 2 H), 4.26 (s, 2 H), 7.50-7.58 (m, 3 H), 7.62 (ddd, J = 7.79, 1.56, 1.45 Hz, 1 H), 7.73 (d, J = 1.45 Hz, 1 H), 7.92 (dq, J = 1.76, 1.63 Hz, 1 H).
Mass Spec. (m/z + 1 = 373).

| 4A-09[2] | H | (CH$_3$)$_2$CH(CH$_2$)$_2$— | H H | H | Cl | H | H | H | —C(O)NH$_2$ | H | H | H |

$^1$H NMR (400 MHz, Methanol-d4) δ ppm 1.20 (d, J = 6.02 Hz, 6 H), 3.22-3.27 (m, 2 H), 3.62-3.69 (m, 1 H), 3.69-3.74 (m, 2 H), 4.29 (s, 2 H), 7.50-7.54 (m, 2 H), 7.56 (d, J = 7.68 Hz, 1 H), 7.61 (dt, J = 7.68, 1.56 Hz, 1 H), 7.71 (d, J = 1.04 Hz, 1 H), 7.89-7.91 (m, 1 H), 7.92 (dt, J = 3.17, 1.64 Hz, 1 H).
Mass Spec. (m/z + 1 = 347).

| 4A-10[1] | H | ![2,2-dimethyl-1,3-dioxolanylmethyl] | H H | H | Cl | H | H | H | —C(O)NH$_2$ | H | H | H |

$^1$H NMR (400 MHz, Methanol-d4) δ ppm 1.34 (d, J = 18.48 Hz, 6 H), 2.69 (d, J = 6.02 Hz, 2 H), 3.62 (dd, J = 8.20, 6.54 Hz, 1 H), 3.83 (s, 2 H), 4.05 (dd, J = 8.20, 6.33 Hz, 1 H), 4.25 (t, J = 6.23 Hz, 1 H), 7.36 (d, J = 0.83 Hz, 2 H), 7.51-7.54 (m, 2 H), 7.60 (ddd, J = 7.89, 1.56, 1.35 Hz, 1 H), 7.88 (dt, J = 7.68, 1.56 Hz, 1 H), 7.91 (t, J = 1.56 Hz, 1 H).
Mass Spec. (m/z + 1 = 375).

| 4A-11[1] | H | ![indanyl] | H H | H | Cl | H | H | H | —C(O)NH$_2$ | H | H | H |

$^1$H NMR (400 MHz, Methanol-d4) δ ppm 1.92-2.01 (m, 1 H), 2.35-2.44 (m, 1 H), 2.78-2.87 (m, 1 H), 3.06 (ddd, J = 15.99, 8.51, 4.57 Hz, 1 H), 3.83-3.92 (m, 2 H), 4.29 (t, J = 6.54 Hz, 1 H), 7.16-7.24 (m, 3 H), 7.35-7.43 (m, 3 H), 7.52 (t, J = 7.68 Hz, 1 H), 7.58-7.62 (m, 2 H), 7.87 (dt, J = 7.84, 1.48 Hz, 1 H), 7.91-7.92 (m, 1 H).
Mass Spec. (m/z + 1 = 377).

| 4A-12[1] | H | ![tetrahydropyranylmethyl] | H H | H | Cl | H | H | H | —C(O)NH$_2$ | H | H | H |

$^1$H NMR (400 MHz, Chloroform-d) δ ppm 1.27-1.38 (m, 1 H), 1.46-1.59 (m, 4 H), 1.83 (dd, J = 4.05, 1.76 Hz, 1 H), 2.59-2.68 (m, 2 H), 3.40-3.50 (m, 2 H), 3.76-3.85 (m, 2 H), 3.97 (dt, J = 11.42, 1.97 Hz, 1 H), 5.75 (s, 1 H), 6.14 (s, 1 H), 7.26-7.30 (m, 2 H), 7.45-7.53 (m, 2 H), 7.60 (ddd, J = 7.79, 1.56, 1.45 Hz, 1 H), 7.81 (dt, J = 7.68, 1.45 Hz, 1 H), 7.84 (t, J = 1.56 Hz, 1 H).
Mass Spec. (m/z + 1 = 359).

TABLE 4A-continued

| Comp. No. | R | R¹ | $R^{2a}$ $R^{2b}$ | R³ | R⁴ | R⁵ | R⁶ | R⁷ | R⁸ | R⁹ | R¹⁰ | R¹¹ |
|---|---|---|---|---|---|---|---|---|---|---|---|---|
| 4A-13[1] | H | tetrahydropyran-2-ylethyl | H H | H | Cl | H | H | H | —C(O)NH₂ | H | H | H |

$^1$H NMR (400 MHz, Chloroform-d) δ ppm 1.22-1.34 (m, 1 H), 1.45-1.54 (m, 2 H), 1.59-1.65 (m, 1 H), 1.66-1.75 (m, 1 H), 1.78-1.89 (m, 3 H), 2.74 (t, J = 6.85 Hz, 2 H), 3.33-3.44 (m, 2 H), 3.81 (s, 2 H), 3.95 (dt, J = 11.26, 2.05 Hz, 1 H), 5.76 (s, 1 H), 6.14 (s, 1 H), 7.26-7.30 (m, 2 H), 7.46 (s, 1 H), 7.50 (t, J = 7.68 Hz, 1 H), 7.60 (dt, J = 7.68, 1.45 Hz, 1 H), 7.81 (dt, J = 7.68, 1.45 Hz, 1 H), 7.85 (t, J = 1.56 Hz, 1 H).
Mass Spec. (m/z + 1 = 373).

[1]Isolated and characterized as the free base.
[2]Isolated and characterized as the hydrochloride salt.
[3]Isolated and characterized as the trifluoroacetic acid salt.

TABLE 4B

| Comp. No. | R | R¹ | $R^{2a}$ $R^{2b}$ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-01[2] | H | (CH₃)₂CH(CH₂)₂— | H H | H | H | H | H | —C(O)NH₂ | H | H | H | H |

$^1$H NMR (400 MHz, Methanol-d4) δ ppm 0.97 (d, J = 6.44 Hz, 6 H), 1.57-1.64 (m, 2 H), 1.65-1.71 (m, 1 H), 3.06-3.12 (m, 2 H), 4.25 (s, 2 H), 7.59 (d, J = 8.51 Hz, 2 H), 7.73-7.80 (m, J = 16.25, 8.57, 2.08, 1.97 Hz, 4 H), 7.96 (d, J = 8.72 Hz, 2 H).
Mass Spec.: (m/z + 1 = 297).

| 4B-02[2] | H | (CH₃)₂CH(CH₂)₂— | H H | H | H | CF₃ | H | —C(O)NH₂ | H | H | H | H |

$^1$H NMR (400 MHz, Methanol-d4) δ ppm 0.95-0.98 (m, 6 H), 1.58-1.64 (m, 2 H), 1.66-1.73 (m, 1 H), 3.07-3.12 (m, 2 H), 4.27 (s, 2 H), 7.46 (t, J = 7.68 Hz, 3 H), 7.56-7.60 (m, 2 H), 8.15 (dd, J = 8.10, 1.87 Hz, 1 H), 8.32 (d, J = 1.66 Hz, 1 H).
Mass Spec.: (m/z + 1 = 365).

| 4B-03[2] | H | benzyl | H H | H | H | CH₃ | H | —C(O)NH₂ | H | H | H | H |

$^1$H NMR (400 MHz, Methanol-d4) δ ppm 2.28 (s, 3 H), 4.29 (s, 2 H), 4.30 (s, 2 H), 7.27 (d, J = 7.89 Hz, 1 H), 7.43-7.52 (m, 7 H), 7.57 (d, J = 8.31 Hz, 2 H), 7.74 (dd, J = 7.89, 1.45 Hz, 1 H), 7.81 (d, J = 2.08 Hz, 1 H).
Mass Spec.: (m/z + 1 = 331).

| 4B-04[2] | H | indan-2-yl | H H | H | H | CH₃ | H | —C(O)NH₂ | H | H | H | H |

$^1$H NMR (400 MHz, Methanol-d4) δ ppm 2.29 (s, 3 H), 3.19 (dd, J = 6.61, 6.64 Hz, 2 H), 3.49 dd, J = 16.20, 7.89 Hz, 2 H), 4.14-4.22 (m, 1 H), 4.36 (s, 2 H), 7.21-7.25 (m, 2 H), 7.26-7.31 (m, 3 H), 7.44-7.47 (m, 2 H), 7.62 (d, J = 8.31 Hz, 2 H), 7.74 (dd, J = 7.89, 1.87 Hz, 1 H), 7.81 (d, J = 1.87 Hz, 1 H).
Mass Spec.: (m/z + 1 = 357).

TABLE 4B-continued

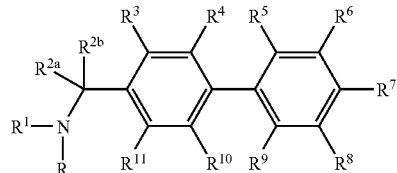

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-05[2] | H | (tetrahydropyran-4-yl-ethyl) | H H | H | H | CH₃ | H | —C(O)NH₂ | H | H | H | H |

¹H NMR (400 MHz, Methanol-d4) δ ppm 1.25 (s, 2 H), 1.57-1.67 (m, 5 H), 2.26 (s, 3 H), 3.08-3.13 (m, 2 H), 3.38 (td, J = 11.83, 2.07 Hz, 2 H), 3.90 (dd, J = 11.62, 4.56 Hz, 2 H), 4.23 (s, 2 H), 7.24 (d, J = 8.09 Hz, 1 H), 7.42 (d, J = 8.30 Hz, 2 H), 7.55 (d, J = 8.09 Hz, 2 H), 7.72 (dd, 7.88, 1.87 Hz, 1 H), 7.79 (d, J = 1.66 Hz, 1 H).
Mass Spec.: (m/z + 1 = 353).

| 4B-06[2] | H | (CH₃)₂CHO(CH₂)₂— | H H | H | H | CH₃ | H | —C(O)NH₂ | H | H | H | H |

¹H NMR (400 MHz, Methanol-d4) δ ppm 1.18 (d, J = 6.02 Hz, 6 H), 2.26 (s, 3 H), 3.20-3.23 (m, 2 H), 3.61-3.66 (m, 1 H), 3.69 (t, J = 5.39, 4.98 Hz, 2 H), 4.26 (s, 2 H), 7.25 (d, J = 7.88 Hz, 1 H), 7.42 (d, J = 8.30 Hz, 2 H), 7.55 (d, J = 8.30 Hz, 2 H), 7.72 (dd, J = 7.99, 1.97 Hz, 1 H), 7.78 (s, 1 H).
Mass Spec.: (m/z + 1 = 327).

| 4B-07[2] | H | (tetrahydrofuran-2-yl-methyl) | H H | H | H | CH₃ | H | —C(O)NH₂ | H | H | H | H |

¹H NMR (400 MHz, Methanol-d4) δ ppm 1.55-1.64 (m, 1 H), 1.89-1.98 (m, 2 H), 2.06-2.14 (m, 1 H), 2.27 (s, 3 H), 2.98 (dd, J = 12.76, 10.06 Hz, 1 H), 3.18 (dd, J = 12.86, 2.90 Hz, 1 H), 3.79 (dt, J = 8.45, 6.77 Hz, 1 H), 3.90 (dt, J = 8.30, 6.74 Hz, 1 H), 4.13-4.20 (m, 1 H), 4.23-4.31 (m, 2 H), 7.25 (d, J = 7.88 Hz, 1 H), 7.41 (d, J = 8.30 Hz, 2 H), 7.56 (d, J = 8.30 Hz, 2 H), 7.72 (dd, J = 7.88, 1.45 Hz, 1 H), 7.78 (s, 1 H).
Mass Spec.: (m/z + 1 = 341).

| 4B-08[2] | H | (3-phenylpropyl) | H H | H | H | CH₃ | H | —C(O)NH₂ | H | H | H | H |

¹H NMR (400 MHz, Methanol-d4) δ ppm 1.99-2.08 (m, 2 H), 2.27 (s, 3 H), 2.73 (t, J = 7.58 Hz, 2 H), 3.05-3.11 (m, 2 H), 4.24 (s, 2 H), 7.17-7.23 (m, 3 H), 7.25-7.30 (m, 3 H), 7.42 (d, J = 8.31 Hz, 2 H), 7.54 (d, J = 8.31 Hz, 2 H), 7.74 (dd, J = 7.99, 1.97 Hz, 1 H), 7.81 (d, J = 1.87 Hz, 1 H).
Mass Spec.: (m/z + 1 = 359).

| 4B-09[2] | H | (2-phenylethyl) | H H | H | H | CH₃ | H | —C(O)NH₂ | H | H | H | H |

¹H NMR (400 MHz, MethanoL-d4) δ ppm 2.29 (s, 3 H), 2.96-3.06 (m, 2 H), 3.30-3.34 (m, 2 H), 4.29 (s, 2 H), 7.25-7.31 (m, 4 H), 7.31-7.37 (m, 2 H), 7.44 (d, J = 8.31 Hz, 2 H), 7.59 (d, J = 8.31 Hz, 2 H), 7.74 (dd, J = 7.89, 1.87 Hz, 1 H), 7.81 (d, J = 1.45 Hz, 1 H).
Mass Spec.: (m/z + 1 = 345).

| 4B-10[2] | H | 3-chloro-benzyl | H H | H | H | CH₃ | H | —C(O)NH₂ | H | H | H | H |

¹H NMR (400 MHz, Methanol-d4) δ ppm 2.29 (s, 3 H), 4.30 (s, 2 H), 4.32 (s, 2 H), 7.27 (d, J = 7.89 Hz, 1 H), 7.42-7.49 (m, 5 H), 7.59 (td, J = 3.11, 1.87 Hz, 3 H), 7.74 (dd, J = 7.99, 1.97 Hz, 1 H), 7.81 (d, J = 1.87 Hz, 1 H).
Mass Spec.: (m/z + 1 = 365).

| 4B-11[2] | H | (2-cyclopropylethyl) | H H | H | H | CH₃ | H | —C(O)NH₂ | H | H | H | H |

TABLE 4B-continued

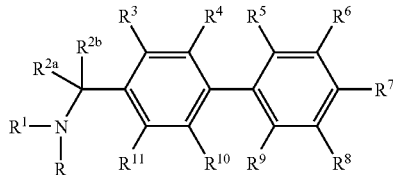

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|

¹H NMR (400 MHz, Methanol-d4) δ ppm 0.13-0.18 (m, 2 H), 0.54 (ddd, J = 7.99, 5.92, 4.36 Hz, 2 H), 0.72-0.81 (m, 1 H), 1.59-1.66 (m, 2 H), 2.28 (s, 3 H), 3.12-3.20 (m, 2 H), 4.27 (s, 2 H), 7.27 (d, J = 7.89 Hz, 1 H), 7.44 (d, J = 8.31 Hz, 2 H), 7.58 (d, J = 8.10 Hz, 2 H), 7.74 (dd, J = 7.99, 1.77 Hz, 1 H), 7.81 (d, J = 1.45 Hz, 1 H).
Mass Spec.: (m/z + 1 = 309).

4B-12²   H   (CH₃)₂CH(CH₂)₂—   H H   H   H   H   F   —C(O)NH₂   H   F   H   H

¹H NMR (400 MHz, Methanol-d4) δ ppm 0.94-0.98 (m, 6 H), 1.57-1.64 (m, 2 H), 1.66-1.71 (m, 1 H), 3.04-3.13 (m, 2 H), 4.26 (s, 2 H), 7.56-7.64 (m, 6 H).
Mass Spec.: (m/z + 1 = 333).

4B-13¹   H   [naphthylmethyl group]   H H   H   H   H   H   —C(O)NH₂   H   CH₃   H   H ¹H NMR (400 MHz, Chloroform-d) δ ppm 1.56 (s, 2 H), 2.33 (s, 3 H), 4.00 (s, 4 H), 7.20 (s, 4 H), 7.30 (dd, J = 7.89, 2.91 Hz, 3 H), 7.50 (s, 2 H), 7.64 (dd, J = 7.79, 1.77 Hz, 1 H), 7.75 (d, J = 1.45 Hz, 1 H).
Mass Spec.: (m/z + 1 = 343).

4B-14²   H   (CH₃)₂CH(CH₂)₂—   H H   H   H   CH₃   H   —C(O)NH₂   H   CH₃   H   H

¹H NMR (400 MHz, Methanol-d4) δ ppm 0.97 (d, J = 6.44 Hz, 6 H), 1.59-1.65 (m, 2 H), 1.66-1.76 1.76 (m, 1 H), 2.03 (s, 6 H), 3.08-3.14 (m, 2 H), 4.26 (s, 2 H), 7.25 (d, J = 8.10 Hz, 2 H), 7.60-7.64 (m, 4 H).
Mass Spec.: (m/z + 1 = 325).

4B-15²   H   (CH₃)₂CH(CH₂)₂—   H H   H   H   H   H   —C(O)NH₂   F   H   H   H

¹H NMR (400 MHz, Methanol-d4) δ ppm 0.97 (d, J = 6.44 Hz, 6 H), 1.57-1.63 (m, 2 H,) 1.69 (dt, J = 13.24, 6.57 Hz, 1 H), 3.06-3.12 (m, 2 H), 4.25 (s, 2 H), 7.53 (dd, J = 12.35, 1.77 Hz, 1 H), 7.60 (tt, J = 6.15, 1.95 Hz, 3 H), 7.80 (d, J = 8.51 Hz, 2 H), 7.91 (t, J = 7.99 Hz, 1 H).
Mass Spec.: (m/z + 1 = 325).

4B-16²   H   [phenoxypropyl group]   H H   H   H   H   H   —C(O)NH₂   H   CH₃   H   H ¹H NMR (400 MHz, Chloroform-d) δ ppm 2.31 (s, 3 H), 3.07 (t, J = 5.19 Hz, 2 H), 3.92 (s, 2 H), 4.11 (t, J = 5.09 Hz, 2 H), 5.66 (s, 1 H), 6.10 (s, 1 H), 6.89-6.98 (m, 3 H), 7.24-7.30 (m, 4 H), 7.41 (d, J = 8.10 Hz, 2 H), 7.63 (dd, J = 7.89, 1.66 Hz, 1 H), 7.74 (d, J = 1.45 Hz, 1 H).
Mass Spec.: (m/z + 1 = 361).

4B-17²   H   3-fluoro-benzyl   H H   H   H   H   H   —C(O)NH₂   H   CH₃   H   H

¹H NMR (400 MHz, Methanol-d4) δ ppm 2.26 (s, 3 H), 4.29 (s, 4 H), 7.19 (td, J = 8.56, 2.39 Hz, 1 H), 7.23-7.33 (m, 3 H), 7.42 (d, J = 7.88 Hz, 2 H), 7.44-7.50 (m, 1 H), 7.55 (d, J = 8.09 Hz, 2 H), 7.71 (d, J = 7.88 Hz, 1 H), 7.78 (s, 1 H).
Mass Spec.: (m/z + 1 = 349).

4B-18²   H   [2,2-dimethyl-benzofuranyl group]   H H   H   H   H   H   —C(O)NH₂   H   CH₃   H   H ¹H NMR (400 MHz, Methanol-d4) δ ppm 1.41 (s, 6 H), 2.26 (s, 3 H), 3.02 (s, 2 H), 4.15 (s, 2 H), 4.23 (s, 2 H), 6.70 (d, J = 8.09 Hz, 1 H), 7.19 (dd, J = 8.19, 1.97 Hz, 1 H), 7.25 (d, J = 7.88 Hz, 2 H), 7.41 (d, J = 8.30 Hz, 2 H), 7.53 (d, J = 8.30 Hz, 2 H), 7.71 (dd, J = 7.68, 1.66 Hz, 1 H), 7.78 (d, J = 1.87 Hz, 1 H).
Mass Spec.: (m/z + 1 = 401).

TABLE 4B-continued

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-19[2] | H | (1-methyl-1-phenylethyl group; C(CH₃)₂-Ph) | H H | H | H | H | H | —C(O)NH₂ | H | CH₃ | H | H |

¹H NMR (400 MHz, Methanol-d4) δ ppm 1.85 (s, 6 H), 2.24 (s, 3 H), 3.87 (s, 2 H), 7.21 (d, J = 7.88 Hz, 1 H), 7.34-7.41 (m, 5 H), 7.45-7.50 (m, 1 H), 7.54 (td, J = 6.59, 1.76 Hz, 2 H), 7.62-7.65 (m, 2 H), 7.70 (dd, J = 7.99, 1.97 Hz, 1 H), 7.77 (d, J = 1.87 Hz, 1 H.)
Mass Spec.: (m/z + 1 = 359).

| 4B-20[2] | H | (2,3-dihydrobenzofuran-5-ylmethyl) | H H | H | H | H | H | —C(O)NH₂ | H | CH₃ | H | H |

¹H NMR (400 MHz, Methanol-d4) δ ppm 2.26 (s, 3 H), 3.21 (t, J = 8.71 Hz, 2 H), 4.17 (s, 2 H), 4.23 (s, 2 H), 4.55 (t, J = 8.82 Hz, 2 H), 6.76 (d, J = 8.30 Hz, 1 H), 7.19 (dd, J = 8.19, 1.97 Hz, 1 H), 7.24 (d, J = 7.88 Hz, 1 H), 7.31 (s, 1 H), 7.41 (d, J = 8.30 Hz, 2 H), 7.53 (d, J = 8.30 Hz, 2 H), 7.71 (dd, J = 7.88, 1.87 Hz, 1 H).
Mass Spec.: (m/z + 1 = 373).

| 4B-21[2] | H | (indan-1-yl) | H H | H | H | H | H | —C(O)NH₂ | H | CH₃ | H | H |

¹H NMR (400 MHz, Methanol-d4) δ ppm 2.26 (s, 3 H), 2.29-2.39 (m, 1 H), 2.59-2.69 (m, 1 H), 3.01 (ddd, J = 16.39, 8.92, 4.56 Hz, 1 H), 3.18-3.23 (m, 1 H), 4.32 (s, 2 H) 4.90 (dd, J = 7.88, 4.15 Hz, 1 H), 7.24 (d, J = 7.88 Hz, 1 H), 7.30-7.34 (m, 1 H), 7.37-7.43 (m, 4 H), 7.56 (d, J = 8.30 Hz, 2 H), 7.60 (d, J = 7.47 Hz, 1 H), 7.71 (dd, J = 7.68, 1.66 Hz, 1 H), 7.78 (s, 1 H).
Mass Spec.: (m/z + 1 = 357).

| 4B-22[2] | H | (8-methylchroman-4-yl) | H H | H | H | H | H | —C(O)NH₂ | H | CH₃ | H | H |

¹H NMR (400 MHz, Methanol-d4) δ ppm 2.16 (s, 3 H), 2.26 (s, 3 H), 2.37-2.48 (m, 2 H), 4.33-4.42 4.42 (m, 4 H), 4.60 (t, J = 4.77 Hz, 1 H), 6.89 (t, J = 7.47 Hz, 1 H), 7.17-7.26 (m, 3 H), 7.42 (d, J = 8.09 Hz, 2 H), 7.58 (d, J = 7.88 Hz, 2 H), 7.71 (d, J = 8.09 Hz, 1 H), 7.78 (s, 1 H).
Mass Spec.: (m/z + 1 = 387).

| 4B-23[2] | H | (1-(3-chlorophenyl)cyclopropyl)methyl | H H | H | H | H | H | —C(O)NH₂ | H | CH₃ | H | H |

¹H NMR (400 MHz, Methanol-d4) δ ppm 1.33-1.37 (m, 2 H), 1.48-1.52 (m, 2 H), 2.23 (s, 3H), 4.18 (s, 2 H), 7.21 (d, J = 7.88 Hz, 1 H), 7.35-7.43 (m, 4 H), 7.48-7.51 (m, 2 H), 7.58 (td, TABLE 4B-continued

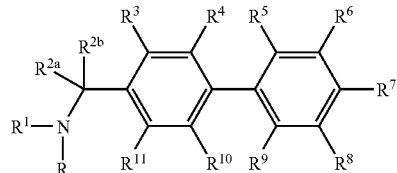

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|

J = 4.41, 1.76 Hz, 1 H), 7.68-7.72 (m, 2 H), 7.77 (s, 1 H).
Mass Spec.: (m/z + 1 = 391).

4B-24[2]  H  1-phenylcyclopropyl/methyl group  H H  H  H  H  H  —C(O)NH₂  H  CH₃  H  H $^1$H NMR (400 MHz, Methanol-d4) δ ppm 1.27-1.39 (m, 2 H), 1.45-1.49 (m, 2 H), 2.23 (s, 3 H), 4.15 (s, 2 H), 7.21 (d, J = 8.09 Hz, 1 H), 7.38 (ddd, J = 15.40, 6.28, 2.18 Hz, 5 H), 7.45-7.54 (m, 2 H), 7.62-7.66 (m, 2 H), 7.70 (dd, J = 7.68, 1.66 Hz, 1 H), 7.77 (d, J = 1.87 Hz, 1 H).
Mass Spec.: (m/z + 1 = 357).

4B-25[2]  H  2-(3-chlorophenyl)propan-2-yl  H H  H  H  H  H  —C(O)NH₂  H  CH₃  H  H $^1$H NMR (400 MHz, Methanol-d4) δ ppm 1.85 (s, 6 H) 2.24 (s, 3 H) 3.92 (s, 2 H) 7.21 (d, J = 7.88 Hz, 1 H) 7.38 (s, 4 H) 7.49-7.59 (m, 3 H) 7.67 (t, J = 1.56 Hz, 1 H) 7.70 (dd, J = 7.88, 1.45 Hz, 1 H) 7.77 (s, 1 H)
Mass Spec.: (m/z + 1 = 393).

4B-26[2]  H  2-fluoro-benzyl   H H  H  H  H  H  —C(O)NH₂  H  CH₃  H  H $^1$H NMR (400 MHz, Methanol-d4) δ ppm 2.28 (s, 3 H), 4.35 (s, 4 H), 7.24-7.31 (m, 3 H), 7.44 (d, J = 8.51 Hz, 2 H), 7.49-7.57 (m, 2 H), 7.59 (d, J = 8.31 Hz, 2 H), 7.74 (dd, J = 7.89, 1.87 Hz, 1 H), 7.81 (d, J = 1.45 Hz, 1 H).
Mass Spec.: (m/z + 1 = 349).

4B-27[2]  H  1-(naphthalen-2-yl)ethyl  CH₃ H  H  H  H  H  —C(O)NH₂  H  CH₃  H  H $^1$H NMR (400 MHz, Methanol-d4) δ ppm 1.82 (d, J = 7.06 Hz, 3 H), 2.26 (s, 3 H), 4.00 (d, J = 13.08 Hz, 1 H), 4.25 (d, J = 13.29 Hz, 1 H), 4.64-4.70 (m, 1 H), 7.23 (d, J = 8.10 Hz, 1 H), 7.39 (d, J = 8.31 Hz, 2 H), 7.47 (d, J = 8.31 Hz, 2 H), 7.55-7.63 (m, 3 H), 7.72 (dd, J = 7.89, 1.87 Hz, 1 H), 7.79 (d, J = 1.45 Hz, 1 H), 7.91-7.96 (m, 2 H), 8.01-8.05 (m, 2 H).
Mass Spec.: (m/z + 1 = 395).

4B-28[2]  H  1,2,3,4-tetrahydronaphthalen-1-yl  H H  H  H  H  H  —C(O)NH₂  H  CH₃  H  H $^1$H NMR (400 MHz, Methanol-d4) δ ppm 1.91-2.03 (m, 2 H), 2.15-2.24 (m, 1 H), 2.28 (s, 3 H), 2.29-2.37 (m, J = 11.21 Hz, 1 H), 2.81-2.90 (m, J = 5.81 Hz, 1 H), 2.97 (ddd, J = 11.52, 5.71, 5.61 Hz, 1 H), 4.31-4.39 (m, 2 H), 4.58 (t, J = 4.98 Hz, 1 H), 7.24-7.31 (m, 3 H), 7.35 (td, J = 7.42, 1.56 Hz, 1 H), 7.39-7.46 (m, 3 H), 7.59 (d, J = 8.31 Hz, 2 H), 7.73 (dd, J = 7.99, 1.97 Hz, 1 H), 7.81 (d, J = 1.25 Hz, 1 H).
Mass Spec.: (m/z + 1 = 371).

TABLE 4B-continued

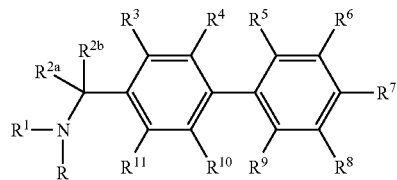

| Comp. No. | R | R[1] | R[2a] R[2b] | R[3] | R[4] | R[5] | R[6] | R[7] | R[8] | R[9] | R[10] | R[11] |
|---|---|---|---|---|---|---|---|---|---|---|---|---|
| 4B-29[2] | H | (CH$_3$)$_2$CH(CH$_2$)$_2$— | H H | H | H | H | H | —C(O)NH$_2$ | H | Cl | H | H |

$^1$H NMR (400 MHz, Methanol-d4) δ ppm 0.97 (d, J = 6.44 Hz, 6 H), 1.58-1.64 (m, 2 H), 1.66-1.71 (m, 1 H), 3.08-3.13 (m, 2 H), 4.26 (s, 2 H), 7.47 (d, J = 8.10 Hz, 1 H), 7.58 (ddd, J = 16.14, 6.28, 2.08 Hz, 4 H), 7.87 (dd, J = 8.10, 1.87 Hz, 1 H), 8.03 (d, J = 1.66 Hz, 1 H).
Mass Spec.: (m/z + 1 = 331).

| 4B-30[2] | H |  | H H | H | H | H | H | —C(O)NH$_2$ | H | Cl | H | H |

$^1$H NMR (400 MHz, Methanol-d4) δ ppm 3.20 (dd, J = 16.20, 6.64 Hz, 2 H), 3.48 (dd, J = 16.30, 7.99 Hz, 2 H), 4.15-4.22 (m, 1 H), 4.37 (s, 2 H), 7.21-7.25 (m, 2 H), 7.26-7.31 (m, 2 H), 7.47 (d, J = 7.89 Hz, 1 H), 7.57 (d, J = 8.31 Hz, 2 H), 7.64 (d, J = 8.31 Hz, 2 H), 7.86-7.90 (m, 1 H), 8.03 (d, J = 1.87 Hz, 1 H).
Mass Spec.: (m/z + 1 = 377).

| 4B-31[2] | H |  | H H | H | H | H | H | —C(O)NH$_2$ | H | CH$_3$ | H | H |

$^1$H NMR (400 MHz, Methanol-d4) δ ppm 2.29 (s, 3 H), 2.94-3.01 (m, 1 H), 3.30-3.36 (m, 2 H), 3.41-3.48 (m, 1 H), 4.36 (d, J = 4.57 Hz, 2 H), 5.07-5.15 (m, J = 9.63, 9.63, 6.59, 3.01 Hz, 1 H), 6.82-6.90 (m, 2 H), 7.10-7.15 (m, 1 H), 7.20-7.23 (m, 1 H), 7.27 (d, J = 7.89 Hz, 1 H), 7.45 (d, J = 8.10 Hz, 2 H), 7.60 (d, J = 8.10 Hz, 2 H), 7.74 (dd, J = 7.99, 1.97 Hz, 1 H), 7.81 (d, J = 1.45 Hz, 1 H).
Mass Spec.: (m/z + 1 = 373).

| 4B-32[2] | H |  | H H | H | H | CH$_3$ | H | —C(O)NH$_2$ | H | CH$_3$ | H | H |

$^1$H NMR (400 MHz, Methanol-d4) δ ppm 2.04 (s, 6 H), 3.21 (dd, J = 16.20, 6.64 Hz, 2 H), 3.48 dd, J = 16.20, 8.10 Hz, 2 H), 4.20 (t, J = 7.48 Hz, 1 H), 4.37 (s, 2 H), 7.20-7.24 (m, 2 H), 7.25-7.30 (m, 4 H), 7.63 (s, 2 H), 7.67 (d, J = 8.10 Hz, 2 H).
Mass Spec.: (m/z + 1 = 371).

| 4B-33[2] | H |  | H H | H | H | H | H | —C(O)NH$_2$ | H | CH$_3$ | H | H |

$^1$H NMR (500 MHz, Methanol-d4) δ ppm 2.31 (s, 3 H), 2.36-2.43 (m, J = 9.27, 9.27, 4.41, 4.28 Hz, 1 H), 2.66-2.73 (m, 1 H), 3.04-3.10 (m, 1 H), 3.27 (dd, J = 16.07, 7.78 Hz, 1 H), 4.37 (s, 2 H) 4.95 (dd, J = 7.91, 4.02 Hz, 1 H), 7.29 (d, J = 8.03 Hz, 1 H), 7.36-7.40 (m, 1 H), 7.43-7.48 (m, 4 H), 7.61 (d, J = 8.03 Hz, 2 H), 7.65 (d, J = 7.52 Hz, 1 H), 7.76 (d, J = 8.03 Hz, 1 H), 7.84 (s, 1 H).
Mass Spec.: (m/z + 1 = 357).

TABLE 4B-continued

| Comp. No. | R | R[1] | R[2a] R[2b] | R[3] | R[4] | R[5] | R[6] | R[7] | R[8] | R[9] | R[10] | R[11] |
|---|---|---|---|---|---|---|---|---|---|---|---|---|
| 4B-34[2] | H | (1-indanyl with methyl) | H H | H | H | H | H | —C(O)NH$_2$ | H | CH$_3$ | H | H |
| 4B-35[2] | H | (2-indanylmethyl) | H H | H | H | H | H | —C(O)NH$_2$ | H | CH$_3$ | H | H |
| 4B-36[2] | H | (chroman-2-ylmethyl) | H H | H | H | H | H | —C(O)NH$_2$ | H | CH$_3$ | H | H |
| 4B-37[2] | H | (tetrahydropyran-4-ylethyl) | H H | H | H | H | H | —C(O)NH$_2$ | H | Cl | H | H |
| 4B-38[2] | H | (1-indanyl) | H H | H | H | H | H | —C(O)NH$_2$ | H | Cl | H | H |

$^1$H NMR (400 MHz, Methanol-d4) δ ppm 2.28 (s, 3 H), 2.32-2.40 (m, 1 H), 2.63-2.69 (m, 1 H), 3.05 (s, 1 H), 3.20-3.27 (m, J = 7.89 Hz, 1 H), 4.34 (s, 2 H) 4.92 (dd, J = 7.89, 4.36 Hz, 1 H), 7.26 (d, J = 8.10 Hz, 1 H), 7.32-7.37 (m, 1 H), 7.40-7.45 (m, 4 H), 7.57 (d, J = 8.31 Hz, 2 H), 7.61 (d, J = 7.27 Hz, 1 H), 7.73 (dd, J = 7.99, 1.97 Hz, 1 H), 7.81 (d, J = 1.45 Hz, 1 H). Mass Spec.: (m/z + 1 = 357).

$^1$H NMR (400 MHz, Methanol-d4) δ ppm 2.29 (s, 4 H), 2.73-2.85 (m, 3 H), 3.14-3.20 (m, 2 H), 3.24 (d, J = 7.06 Hz, 2 H), 4.31 (s, 2 H), 7.11-7.15 (m, 2 H), 7.18-7.22 (m, 2 H), 7.27 (d, J = 8.10 Hz, 1 H), 7.45 (d, J = 8.10 Hz, 2 H), 7.61 (d, J = 8.31 Hz, 2 H), 7.74 (dd, J = 8.10, 1.66 Hz, 1 H), 7.81 (s, 1 H). Mass Spec.: (m/z + 1 = 371).

$^1$H NMR (500 MHz, Methanol-d4) δ ppm 2.31 (s, 3 H), 2.52 (s, 1 H), 2.70 (d, J = 16.33 Hz, 1 H), 3.07 (d, J = 5.70 Hz, 1 H), 3.13-3.18 (m, 1 H), 3.22-3.26 (m, 1 H), 4.04 (dd, J = 11.53, 6.87 Hz, 1 H), 4.30 (dd, J = 11.27, 1.94 Hz, 1 H), 4.34 (s, 2 H), 6.79 (d, J = 8.55 Hz, 1 H), 6.88 (t, J = 7.00 Hz, 1 H), 7.09 (d, J = 7.52 Hz, 2 H), 7.30 (d, J = 8.03 Hz, 1 H), 7.48 (d, J = 7.78 Hz, 2 H), 7.62 (d, J = 7.78 Hz, 2 H), 7.77 (d, J = 8.55 Hz, 1 H), 7.84 (s, 1 H). Mass Spec.: (m/z + 1 = 387).

$^1$H NMR (400 MHz, Methanol-d4) δ ppm 1.32 (s, 2 H), 1.66 (s, 4 H), 3.11-3.16 (m, 2 H), 3.37-3.46 (m, 3 H), 3.93 (s, 2 H), 4.27 (s, 2 H), 7.46 (d, J = 8.10 Hz, 1 H), 7.55-7.61 (m, 4 H), 7.87 (dd, J = 7.89, 1.87 Hz, 1 H), 8.03 (d, J = 1.66 Hz, 1 H). Mass Spec.: (m/z + 1 = 373).

$^1$H NMR (400 MHz, Methanol-d4) δ ppm 2.32-2.40 (m, 1 H), 2.61-2.71 (m, 1 H), 3.05 (dd, J = 12.98, 7.99 Hz, 1 H), 3.20-3.27 (m, 1 H), 4.35 (s, 2 H), 4.92 (dd, J = 7.99, 4.05 Hz, 2 H), 7.32-7.37 (m, 1 H), 7.40-7.42 (m, 2 H), 7.46 (d, J = 8.10 Hz, 1 H), 7.54-7.63 (m, 5 H), 7.87 (dd, J = 7.99, 1.76 Hz, 1 H), 8.03 (d, J = 1.87 Hz, 1 H). Mass Spec.: (m/z + 1 = 377).

TABLE 4B-continued

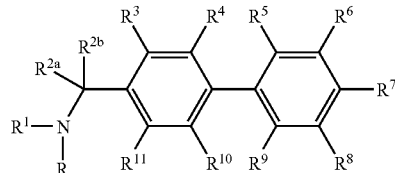

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-39[2] | H | cyclopentyl-CH₂CH₂- | H H | H | H | H | H | —C(O)NH₂ | H | Cl | H | H |

¹H NMR (400 MHz, Methanol-d4) δ ppm 1.17 (s, 2 H), 1.54-1.62 (m, 2 H), 1.64-1.76 (m, 3 H), 1.80-1.88 (m, 4 H), 3.06-3.12 (m, 2 H), 4.26 (s, 2 H), 7.47 (d, J = 7.89 Hz, 1 H), 7.58 (ddd, J = 15.52, 6.18, 2.18 Hz, 4 H), 7.87 (dd, J = 8.10, 1.87 Hz, 1 H), 8.03 (d, J = 1.66 Hz, 1 H). Mass Spec.: (m/z + 1 = 357).

| 4B-40[2] | H | tetrahydropyran-4-yl-CH₂- | H H | H | H | H | H | —C(O)NH₂ | H | CH₃ | H | H |

¹H NMR (400 MHz, Methanol-d4) δ ppm 1.31-1.41 (m, 2 H), 1.67-1.73 (m, 2 H), 1.97-2.06 (m, 1 H), 3.00 (d, J = 7.06 Hz, 2 H), 3.42 (td, J = 11.94, 2.08 Hz, 2 H), 3.93-3.98 (m, 2 H) 4.28 (s, 2 H), 7.27 (d, J = 7.89 Hz, 1 H), 7.45 (d, J = 8.31 Hz, 2 H), 7.59 (d, J = 8.10 Hz, 2 H), 7.74 (dd, J = 7.89, 1.87 Hz, 1 H), 7.81 (s, 1 H). Mass Spec.: (m/z + 1 = 339).

| 4B-41[2] | H | 1-phenylethyl (CH₃) | H H | H | H | H | H | —C(O)NH₂ | H | CH₃ | H | H |

¹H NMR (500 MHz, Methanol-d4) δ ppm 1.76 (d, J = 7.00 Hz, 3 H), 2.30 (s, 3 H), 4.00 (d, J = 12.96 Hz, 1 H), 4.22 (d, J = 12.96 Hz, 1 H), 4.51 (q, J = 6.74 Hz, 1 H), 7.28 (d, J = 8.03 Hz, 1 H), 7.44 (d, J = 8.03 Hz, 2 H), 7.49-7.56 (m, 7 H), 7.76 (dd, J = 7.91, 1.43 Hz, 1 H), 7.83 (s, 1 H). Mass Spec.: (m/z + 1 = 345).

| 4B-42[2] | H | 1-phenylethyl (CH₃) | H H | H | H | H | H | —C(O)NH₂ | H | CH₃ | H | H |

¹H NMR (500 MHz, Methanol-d4) δ ppm 1.76 (d, J = 7.00 Hz, 3 H), 2.30 (s, 3 H), 4.00 (d, J = 13.22 Hz, 1 H), 4.22 (d, J = 12.96 Hz, 1 H), 4.51 (q, J = 7.08 Hz, 1 H), 7.28 (d, J = 8.03 Hz, 1 H), 7.44 (d, J = 8.29 Hz, 2 H), 7.49-7.56 (m, 7 H), 7.71-7.79 (m, 1 H), 7.83 (s, 1 H). Mass Spec.: (m/z + 1 = 345).

| 4B-43[2] | H | pyridin-3-yl-CH₂- | H H | H | H | H | H | —C(O)NH₂ | H | CH₃ | H | H |

¹H NMR (500 MHz, Methanol-d4) δ ppm 2.31 (s, 3 H), 4.48 (s, 2 H), 4.64 (s, 2 H), 7.30 (d, J = 8.03 Hz, 1 H), 7.49 (d, J = 8.03 Hz, 2 H), 7.70 (d, J = 8.29 Hz, 2 H), 7.77 (dd, J = 8.03, 1.81 Hz, 1 H), 7.84 (s, 1 H), 8.16 (dd, J = 8.29, 5.70 Hz, 1 H), 8.78 (d, J = 8.03 Hz, 1 H), 8.97 (d, J = 5.70 Hz, 1 H), 9.13 (d, J = 1.30 Hz, 1 H). Mass Spec.: (m/z + 1 = 332).

| 4B-44[2] | H | pyridin-2-yl-CH₂- | H H | H | H | H | H | —C(O)NH₂ | H | CH₃ | H | H |

TABLE 4B-continued

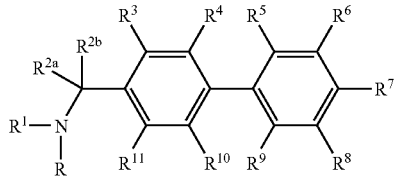

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|

¹NMR (500 MHz, Methanol-d4) δ ppm 2.32 (s, 3 H), 4.41 (s, 2 H), 4.47 (s, 2 H), 7.32 (t, J = 8.68 Hz, 2 H), 7.45-7.50 (m, 2 H), 7.53 (d, J = 8.03 Hz, 1 H), 7.64 (d, J = 8.03 Hz, 2 H), 7.78 (d, J = 1.56 Hz, 1 H), 7.84 (s, 1 H), 7.92-7.96 (m, 1 H), 8.71 (s, 1 H).
Mass Spec.: (m/z + 1 = 332).

| 4B-45[2] | H | (CH₃)₂CH(CH₂)₂— | H H | H | H | H | H | —C(O)NH₂ | H | OBn | H | H |

¹H NMR (500 MHz, Methanol-d4) δ ppm 0.99 (d, J = 6.74 Hz, 6 H), 1.56-1.64 (m, 2 H), 1.66-1.74 (m, 1 H), 3.07-3.11 (m, 2 H), 4.24 (s, 2 H), 5.18 (s, 2 H), 7.28-7.35 (m, 3 H), 7.35-7.39 (m, 2 H), 7.44 (d, J = 7.78 Hz, 1 H), 7.53 (d, J = 8.29 Hz, 2 H), 7.60 (dd, J = 7.91, 1.17 Hz, 1 H), 7.69 (d, J = 8.03 Hz, 2 H), 7.73 (d, J = 1.30 Hz, 1 H).
Mass Spec.: (m/z + 1 = 403).

| 4B-46[2] | H | (CH₃)₂CH(CH₂)₂— | H H | H | H | H | H | —C(O)NH₂ | H | OCH₃ | H | H |

¹H NMR (500 MHz, MethanoL-d4) δ ppm 1.00 (d, J = 6.48 Hz, 6 H), 1.61-1.66 (m, 2 H), 1.68-1.75 (m, 1 H), 3.10-3.14 (m, 2 H), 3.88 (s, 3 H), 4.26 (s, 2 H), 7.41 (d, J = 7.78 Hz, 1 H), 7.54-7.58 (m, 3 H), 7.62 (d, J = 1.56 Hz, 1 H), 7.65 (d, J = 8.29 Hz, 2 H).
Mass Spec.: (m/z + 1 = 327).

| 4B-47[2] | H | (CH₃)₂CH(CH₂)₂— | H H | H | H | H | H | —C(O)NH₂ | H | OH | H | H |

¹H NMR (500 MHz, Methanol-d4) δ ppm 1.00 (d, J = 6.48 Hz, 6 H), 1.61-1.66 (m, 2 H), 1.68-1.76 (m, 1 H), 3.09-3.13 (m, 2 H), 4.26 (s, 2 H), 7.37-7.43 (m, 3 H), 7.55 (d, J = 8.03 Hz, 2 H), 7.73 (d, J = 8.03 Hz, 2 H).
Mass Spec.: (m/z + 1 = 313).

| 4B-48[2] | H | (CH₃)₂CH(CH₂)₂— | H H | H | H | H | H | —C(O)NH₂ | H | Et | H | H |

¹H NMR (400 MHz, Methanol-d4) δ ppm 0.98 (d, J = 6.64 Hz, 6 H), 1.08 (t, J = 7.57 Hz, 3 H), 1.59-1.66 (m, 2 H), 1.67-1.75 (m, 1 H), 2.64 (q, J = 7.60 Hz, 2 H), 3.07-3.15 (m, 2 H), 4.27 (s, 2 H), 7.24 (d, J = 8.09 Hz, 1 H), 7.43 (ddd, J = 8.19, 1.97, 1.87 Hz, 2 H), 7.56-7.61 (m, 2 H), 7.74 (dd, J = 7.88, 1.87 Hz, 1 H), 7.86 (d, J = 1.87 Hz, 1 H).
Mass Spec.: (m/z + 1 = 325).

| 4B-49[2] | H | (CH₃)₂CH(CH₂)₂— | H H | H | H | Cl | H | —C(O)NH₂ | H | CH₃ | H | H |

¹H NMR (400 MHz, Methanol-d4) δ ppm 0.97 (d, J = 6.64 Hz, 6 H), 1.58-1.65 (m, 2 H), 1.66-1.71 (m, 1 H), 2.11 (s, 3 H), 3.07-3.15 (m, 2 H), 4.27 (s, 2 H), 7.31 (dt, J = 8.31, 1.87 Hz, 2 H), 7.60-7.64 (m, 2 H), 7.76 (d, J = 1.04 Hz, 1 H), 7.85 (d, J = 2.28 Hz, 1 H).
Mass Spec.: (m/z + 1 = 345).

| 4B-50[1] | H | tetrahydropyran-4-ylethyl | H H | H | F | H | CH₃ | H | —C(O)NH₂ | H | H | H | F |

¹H NMR (400 MHz, Chloroform-d) δ ppm 1.23-1.34 (m, 2 H), 1.43-1.50 (m, 2 H), 1.53-1.63 (m, 3 H), 2.30 (s, 3 H), 2.64-2.69 (m, 2 H), 3.36 (td, J = 11.78, 1.76 Hz, 2 H), 3.87-3.98 (m, 4 H) 5.83 (s, 1 H), 6.14 (s, 1 H), 6.81-6.87 (m, 2 H), 7.25 (t, J = 3.95 Hz, 1 H), 7.64 (dd, J = 7.89, 1.87 Hz, 1 H), 7.74 (d, J = 1.87 Hz, 1 H).
Mass Spec.: (m/z + 1 = 389)

| 4B-51[2] | H | tetrahydropyran-4-ylethyl | H H | H | F | H | CH₃ | H | —C(O)NH₂ | H | H | H | F |

¹H NMR (400 MHz, Methanol-d4) δ ppm 1.26-1.38 (m, 2 H), 1.62-1.72 (m, 5 H), 2.31 (s, 3 H), 3.16-3.22 (m, 2 H), 3.41 (td, J = 11.89, 1.97 Hz, 2 H), 3.93 (dd, J = 11.11, 4.05 Hz, 2 H), 4.39 (s, 2 H), 7.18 (d, J = 8.31 Hz, 2 H), 7.31 (d, J = 8.10 Hz, 1 H), 7.76 (dd, J = 7.99, 1.35 Hz, 1 H), 7.83 (d, J = 1.25 Hz, 1 H).
Mass Spec.: (m/z + 1 = 389)

TABLE 4B-continued

| Comp. No. | R | R¹ | R²ᵃ / R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-52[1] | H | 2-pyridyl-CH(CH₂CH₃)- (with gem-methyl) | H / H | H | F | H | CH₃ | H | —C(O)NH₂ | H | H | H | F |
| 4B-53[1] | H | 2-pyridyl-CH(CH₃)- (with gem-methyl) | H / H | H | F | H | CH₃ | H | —C(O)NH₂ | H | H | H | F |
| 4B-54[1] | H | cyclopentyl | H / H | H | F | H | CH₃ | H | —C(O)NH₂ | H | H | H | F |
| 4B-55[1] | H | (tetrahydrofuran-2-yl)-C(CH₃)- | H / H | H | F | H | CH₃ | H | —C(O)NH₂ | H | H | H | F |
| 4B-56[2] | H | (tetrahydropyran-4-yl)-CH₂-C(CH₃)- | H / H | H | H | H | CH₃ | H | —C(O)NH₂ | H | H | H | F |

4B-52[1]: ¹H NMR (400 MHz, Chloroform-d) δ ppm 0.82 (t, J = 7.48 Hz, 3 H), 1.77 (td, J = 7.06, 3.11 Hz, 2 H) 2.28 (s, 3 H), 3.70 (t, J = 6.64 Hz, 1 H), 3.73-3.81 (m, 2 H), 6.76 (d, J = 7.89 Hz, 2 H), 7.13 (ddd, J = 7.48. 4.78, 1.04 Hz, 1 H), 7.21 (d, J = 7.89 Hz, 1 H), 7.34 (d, J = 7.68 Hz, 1 H), 7.61-7.66 (m, 2 H), 7.73 (d, J = 1.25 Hz, 1 H), 8.54 8.57 (m, 1 H).
Mass Spec.: (m/z + 1 = 396)

4B-53[1]: ¹H NMR (400 MHz, Chloroform-d) δ ppm 1.41 (d, J = 6.64 Hz, 3 H), 2.03 (s, 2 H), 2.29 (s, 3 H), 3.76-3.85 (m, 2 H), 3.95 (q, J = 6.51 Hz, 1 H), 5.71 (s, 1 H), 6.09 (s, 1 H) 6.75 6.81 (m, 2 H), 7.14 (ddd, J = 7.48, 4.88, 1.14 Hz, 1 H), 7.22 (d, J = 7.89 Hz, 1 H), 7.38 (d, J = 7.89 Hz, 1 H), 7.60-7.68 (m, 2 H), 7.73 (d, J = 1.45 Hz, 1 H), 8.55 (dd, J = 4.05, 0.93 Hz, 1 H).
Mass Spec.: (m/z + 1 = 382)

4B-54[1]: ¹H NMR (400 MHz, Chloroform-d) δ ppm 1.38-1.90 (m, 8 H), 2.32 (s, 3 H), 3.10-3.20 (m, 1 H) 3.92 (s, 2 H), 5.70 (bs, 1 H), 6.11 (bs, 1 H), 6.84 (d, J = 7.9 Hz, 2 H), 7.25 (d, J = 7.8 Hz, 1 H), 7.64 (dd, J = 8.3, 2.0 Hz, 1 H), 7.74 (s, 1 H).
Mass Spec.: (m/z + 1 = 345)

4B-55[1]: ¹H NMR (400 MHz, Chloroform-d) δ ppm 1.49-1.61 (m, 1 H), 1.81-1.91 (m, 2 H), 1.92-2.01 (m, 1 H), 2.26-2.32 (m, 3 H), 2.65-2.75 (m, 2 H), 3.69-3.78 (m, 1 H), 3.83 (dt, J = 8.25, 6.67 Hz, 1 H), 3.95 (s, 2 H), 3.97-4.05 (m, J = 7.22, 7.09, 7.09, 4.15 Hz, 1 H), 5.65 (s, 1 H), 6.08 (s, 1 H) 6.80-6.89 (m, 2 H), 7.25 (d, J = 7.89 Hz, 1 H), 7.63 (dd, J = 7.89, 1.87 Hz, 1 H), 7.74 (d, J = 1.45 Hz, 1 H).
Mass Spec.: (m/z + 1 = 361)

4B-56[2]: ¹H NMR (400 MHz, Methanol-d4) δ ppm 1.37 (dd, J = 13.29, 4.57 Hz, 2 H), 1.72 (dd, J = 12.98, 1.76 Hz, 2 H), 2.00-2.10 (m, 1 H), 2.30 (s, 3 H), 3.04 (d, J = 7.06 Hz, 2 H), 3.43 (td, J = 11.89, 1.97 Hz, 2 H), 3.96 (dd, J = 11.01, 3.32 Hz, 2 H), 4.36 (s, 2 H), 7.25-7.30 (m, 3 H), 7.65 (t, J = 7.99 Hz, 1 H), 7.75 (dd, J = 7.99, 1.56 Hz, 1 H), 7.82 (d, J = 1.04 Hz, 1 H).
Mass Spec.: (m/z + 1 = 357)

TABLE 4B-continued

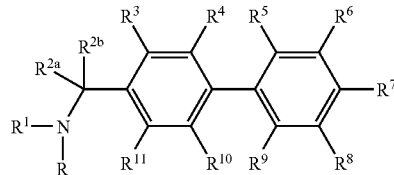

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-57[2] | H | (tetrahydropyran-4-yl-ethyl) | H H | H | F | H | H | —C(O)NH$_2$ | H | Cl | H | F |

$^1$H NMR (400 MHz, Methanol-d4) δ ppm 1.26-1.37 (m, 4 H), 1.61-1.71 (m, 3 H), 3.20 (d, J = 15.57 Hz, 2 H), 3.36-3.45 (m, 2 H), 3.92 (dd, J = 11.32, 4.05 Hz, 2 H), 4.40 (s, 2 H), 7.27-7.34 (m, 2 H), 7.49-7.55 (m, 1 H), 7.87-7.96 (m, 1 H), 8.02-8.12 (m, 1 H).
Mass Spec.: (m/z + 1 = 409)

| 4B-58[2] | H | (tetrahydropyran-4-yl-ethyl) | H H | H | F | H | H | —C(O)NH$_2$ | H | Cl | H | H |

$^1$H NMR (400 MHz, Methanol-d4) δ ppm 1.27 (s, 1 H), 1.33 (d, J = 4.57 Hz, 3 H), 1.61-1.71 (m, 4 H), 3.17 (d, J = 15.57 Hz, 2 H), 3.40 (td, J = 11.84, 1.66 Hz, 2 H), 3.91 (s, 2 H), 4.35 (s, 2 H), 7.39 (d, J = 9.34 Hz, 2 H), 7.49 (d, J = 8.10 Hz, 1 H), 7.65 (t, J = 7.58 Hz, 1 H), 7.89 (dd, J = 7.99, 1.77 Hz, 1 H), 8.04 (d, J = 1.66 Hz, 1 H).
Mass Spec.: (m/z + 1 = 391)

| 4B-59[2] | H | (tetrahydropyran-4-yl-methyl) | H H | H | F | H | CH$_3$ | H | —C(O)NH$_2$ | H | H | H | F |

$^1$H NMR (400 MHz, Methanol-d4) δ ppm 1.29-1.41 (m, 5 H), 2.32 (s, 3 H), 3.08 (d, J = 7.48 Hz, 2 H), 3.43 (td, J = 11.73, 1.87 Hz, 2 H), 3.97 (dd, J = 11.01, 3.53 Hz, 2 H), 4.41 (s, 2 H), 7.18 (d, J = 8.31 Hz, 2 H), 7.31 (d, J = 8.31 Hz, 1 H), 7.76 (d, J = 7.89 Hz, 1 H), 7.83 (s, 1 H).
Mass Spec.: (m/z + 1 = 375)

| 4B-60[2] | H | (tetrahydropyran-4-yl-ethyl) | H H | H | F | H | CH$_3$ | H | —C(O)NH$_2$ | H | H | H | H |

$^1$H NMR (400 MHz, Methanol-d4) δ ppm 1.26-1.37 (m, 2 H), 1.62-1.72 (m, 5 H), 2.30 (s, 3 H), 3.13-3.21 (m, 2 H), 3.41 (td, J = 11.84, 1.66 Hz, 2 H), 3.92 (dd, J = 11.21, 4.15 Hz, 2 H), 4.34 (s, 2 H), 7.24-7.31 (m, 3 H), 7.64 (t, J = 7.99 Hz, 1 H), 7.75 (dd, J = 7.99, 1.35 Hz, 1 H), 7.82 (s, 1 H).
Mass Spec.: (m/z + 1 = 371)

| 4B-61[2] | H | (CH$_3$)$_2$CH(CH$_2$)$_2$— | H H | H | H | F | H | H | —C(O)NH$_2$ | H | Cl | H | H |

$^1$H NMR (400 MHz, Methanol-d4) δ ppm 0.99 (d, J = 6.64 Hz, 7 H), 1.60-1.66 (m, 2 H), 1.68-1.73 (m, 1 H), 3.10-3.16 (m, 2 H), 4.29 (s, 2 H), 7.42-7.50 (m, 4 H), 7.90 (dd, J = 7.99, 1.76 Hz, 1 H), 8.05 (d, J = 1.66 Hz, 1 H).
Mass Spec.: (m/z + 1 = 349)

| 4B-62[2] | H | (CH$_3$)$_2$CH(CH$_2$)$_2$— | H H | H | H | CH$_3$ | H | H | —C(O)NH$_2$ | H | Cl | H | H |

$^1$H NMR (400 MHz, Methanol-d4) δ ppm 0.98 (d, J = 6.44 Hz, 6 H), 1.59-1.65 (m, 2 H), 1.67-1.72 (m, 1 H), 2.15 (s, 3 H), 3.07-3.14 (m, 2 H), 4.23 (s, 2 H), 7.23 (d, J = 7.89 Hz, 1 H), 7.34 (d, J = 7.89 Hz, 1 H), 7.41 (dd, J = 7.89, 1.45 Hz, 1 H), 7.46 (s, 1 H), 7.89 (dd, J = 7.89, 1.66 Hz, 1 H), 8.04 (d, J = 1.66 Hz, 1 H).
Mass Spec.: (m/z + 1 = 345)

| 4B-63[2] | H | (indan-2-yl) | H H | H | H | H | H | —C(O)NH$_2$ | H | Cl | H | F |

TABLE 4B-continued

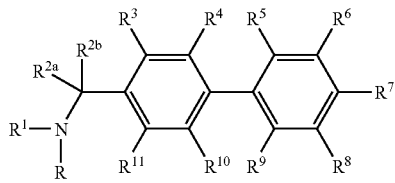

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|

¹H NMR (400 MHz, Methanol-d4) δ ppm 3.22 (dd, J = 16.30, 6.33 Hz, 2 H), 3.52 (dd, J = 16.30, 7.99 Hz, 2 H), 4.20-4.27 (m, 1 H), 4.45 (s, 2 H), 7.22-7.26 (m, 2 H), 7.28-7.32 (m, 2 H), 7.40-7.43 (m, 2 H), 7.51 (d, J = 8.10 Hz, 1 H), 7.70 (t, J = 7.79 Hz, 1 H), 7.90 (dd, J = 7.99, 1.77 Hz, 1 H), 8.05 (d, J = 1.66 Hz, 1 H).
Mass Spec.: (m/z + 1 = 395)

| 4B-64² | H | (CH₃)₂CH(CH₂)₂— | H | H | H | H | H | H | —C(O)NH₂ | H | Cl | H | F |

¹H NMR (400 MHz, Methanol-d4) δ ppm 0.99 (d, J = 6.44 Hz, 6 H), 1.61-1.72 (m, 3 H), 3.13-3.17 (m, 2 H), 4.36 (s, 2 H), 7.40 (d, J = 9.14 Hz, 2 H), 7.50 (d, J = 8.10 Hz, 1 H), 7.66 (t, J = 7.68 Hz, 1 H), 7.90 (dd, J = 8.10, 1.87 Hz, 1 H), 8.05 (d, J = 1.87 Hz, 1 H).
Mass Spec.: (m/z + 1 = 349)

| 4B-65² | H | (CH₃)₂CH(CH₂)₂— | H | H | H | H | H | H | —C(O)NH₂ | H | Cl | H | Cl |

¹H NMR (400 MHz, Methanol-d4) δ ppm 1.03 (d, J = 6.23 Hz, 6 H), 1.68-1.78 (m, 3 H), 3.19-3.26 (m, 2 H), 4.48 (s, 2 H), 7.53 (d, J = 7.89 Hz, 1 H), 7.57 (d, J = 7.89 Hz, 1 H), 7.71 (s, 1 H), 7.77 (d, J = 7.89 Hz, 1 H), 7.94 (d, J = 8.10 Hz, 1 H), 8.09 (s, 1 H).
Mass Spec.: (m/z + 1 = 365)

| 4B-65² | H | (CH₃)₂CH(CH₂)₂— | H | H | H | H | H | H | —C(O)NH₂ | H | Cl | Cl | H |

¹¹H NMR (400 MHz, Methanol-d4) δ ppm 0.98 (d, J = 6.64 Hz, 6 H), 1.58-1.65 (m, 2 H), 1.66-1.70 (m, 1 H), 3.09-3.14 (m, 2 H), 4.27 (s, 2 H), 7.38 (d, J = 8.10 Hz, 1 H), 7.42 (d, J = 7.89 Hz, 1 H), 7.55 (dd, J = 7.79, 1.77 Hz, 1 H), 7.73 (d, J = 1.87 Hz, 1 H), 7.88 (dd, J = 7.99, 1.77 Hz, 1 H), 8.03 (d, J = 1.66 Hz, 1 H).
Mass Spec.: (m/z + 1 = 365)

| 4B-67² | H | tetrahydropyran-4-ylethyl | H | H | H | H | H | H | —C(O)NH₂ | H | Cl | Cl | H |

¹H NMR (400 MHz, Methanol-d4) δ ppm 1.25-1.37 (m, 2 H), 1.60-1.70 (m, 5 H), 3.11-3.17 (m, 2 H), 3.41 (td, J = 11.84, 1.87 Hz, 2 H), 3.92 (dd, J = 11.21, 4.15 Hz, 2 H), 4.27 (s, 2 H), 7.38 (d, J = 7.89 Hz, 1 H), 7.42 (d, J = 7.89 Hz, 1 H), 7.55 (dd, J = 7.89, 1.66 Hz, 1 H), 7.73 (d, J = 1.66 Hz, 1 H), 7.88 (dd, J = 7.99, 1.77 Hz, 1 H), 8.03 (d, J = 1.45 Hz, 1 H).
Mass Spec.: (m/z + 1 = 407)

| 4B-68² | H | indan-2-yl | H | H | H | H | H | H | —C(O)NH₂ | H | Cl | Cl | H |

¹H NMR (400 MHz, Methanol-d4) δ ppm 3.20 (dd, J = 16.40, 6.64 Hz, 2 H), 3.49 (dd, J = 16.51, 7.99 Hz, 2 H), 4.16-4.23 (m, 1 H), 4.38 (s, 2 H), 7.21-7.25 (m, 2 H), 7.27-7.30 (m, 2 H), 7.38 (d, J = 7.89 Hz, 1 H), 7.43 (d, J = 7.89 Hz, 1 H), 7.59 (dd, J = 7.89, 1.66 Hz, 1 H), 7.77 (d, J = 1.66 Hz, 1 H), 7.88 (dd, J = 7.99, 1.77 Hz, 1 H), 8.03 (d, J = 1.66 Hz, 1 H).
Mass Spec.: (m/z + 1 = 411)

| 4B-69² | H | tetrahydropyran-2-ylethyl | H | H | H | H | H | H | —C(O)NH₂ | H | Cl | Cl | H |

¹H NMR (400 MHz, Methanol-d4) δ ppm 1.32 (s, 2 H), 1.55 (s, 4 H), 1.84 (s, 2 H), 3.19 (s, 2 H), 3.44 (s, 2 H), 3.97 (dd, J = 10.90, 2.39 Hz, 1 H), 4.21-4.31 (m, 2 H), 7.38 (d, J = 7.89 Hz, 1 H), 7.41 (d, J = 7.89 Hz, 1 H), 7.53 (dd, J = 7.89, 1.45 Hz, 1 H), 7.71 (d, J = 1.66 Hz, 1 H), 7.88 (dd, J = 7.89, 1.66 Hz, 1 H), 8.03 (d, J = 1.66 Hz, 1 H).
Mass Spec.: (m/z + 1 = 407)

TABLE 4B-continued

| Comp. No. | R | R¹ | $R^{2a}$ $R^{2b}$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|
| 4B-70[2] | H | (tetrahydropyran-4-yl)ethyl– | H H | H | H | $CH_3$ | H | —C(O)$NH_2$ | H | H | $CH_3$ | H |

$^1$H NMR (500 MHz, METHANOL-d4) δ ppm 1.30-1.38 (m, 3 H) 1.65-1.71 (m, 4 H) 2.09 (s, 3 H) 2.11 (s, 3 H) 3.14-3.18 (m, 2 H) 3.41-3.46 (m, 2 H) 3.94-3.97 (m, 2 H) 4.25 (s, 2 H) 7.16 (d, J = 7.78 Hz, 1 H) 7.21 (d, J = 7.52 Hz, 1 H) 7.41 (d, J = 7.78 Hz, 1 H) 7.47 (s, 1 H) 7.77 (dd, J = 8.03, 1.55 Hz, 1 H) 7.85 (s, 1 H)
Mass Spec.: (m/z + 1 = 367)

| 4B-71[2] | H | (tetrahydropyran-4-yl)methyl– | H H | H | H | $CH_3$ | H | —C(O)$NH_2$ | H | H | $CH_3$ | H |

$^1$H NMR (500 MHz, Methanol-d4) δ ppm 1.35-1.44 (m, 2 H), 1.72 (s, 2 H), 2.03-2.08 (m, 1 H), 2.10 (s, 3 H), 2.11 (s, 3 H), 3.03 (d, J = 7.26 Hz, 2 H), 3.46 (t, J = 11.79 Hz, 2 H), 3.99 (dd, J = 11.66, 3.89 Hz, 2 H), 4.27 (s, 2 H), 7.16 (d, J = 7.78 Hz, 1 H), 7.21 (d, J = 7.78 Hz, 1 H), 7.43 (d, J = 7.78 Hz, 1 H), 7.49 (s, 1 H), 7.77 (d, J = 7.78 Hz, 1 H), 7.85 (s, 1 H).
Mass Spec.: (m/z + 1 = 353)

| 4B-72[2] | H | (tetrahydrofuran-2-yl)methyl– | H H | H | H | $CH_3$ | H | —C(O)$NH_2$ | H | H | $CH_3$ | H |

$^1$H NMR (500 MHz, Methanol-d4) δ ppm 1.65 (ddd, J = 15.23, 12.64, 7.13 Hz, 1 H), 1.96-2.03 (m, 2 H), 2.10 (s, 3 H), 2.11 (s, 3 H), 2.12-2.19 (m, 1 H), 3.03 (dd, J = 13.22, 9.59 Hz, 1 H), 3.22 (dd, J = 12.83, 2.98 Hz, 1 H), 3.83-3.87 (m, 1 H), 3.93-3.98 (m, 1 H), 4.19-4.24 (m, J = 10.14, 6.92, 6.92, 2.98 Hz, 1 H), 4.25-4.32 (m, 2 H), 7.16 (d, J = 7.78 Hz, 1 H), 7.20 (d, J = 7.78 Hz, 1 H), 7.41 (d, J = 7.52 Hz, 1 H), 7.47 (s, 1 H), 7.77 (d, J = 7.78 Hz, 1 H), 7.85 (s, 1 H).
Mass Spec.: (m/z + 1 = 339)

| 4B-73[2] | H | indan-2-yl– | H H | H | H | $CH_3$ | H | —C(O)$NH_2$ | H | H | $CH_3$ | H |

$^1$H NMR (500 MHz, Methanol-d4) δ ppm 2.10 (s, 3 H), 2.11 (s, 3 H), 3.22 (dd, J = 16.07, 6.74 Hz, 2 H), 3.51 (dd, J = 16.33, 8.03 Hz, 3 H), 4.16-4.24 (m, 1 H), 4.35 (s, 2 H), 7.17 (d, J = 8.03 Hz, 1 H), 7.22 (d, J = 7.78 Hz, 1 H), 7.24-7.28 (m, 2 H), 7.30-7.35 (m, 2 H), 7.45 (d, J = 7.78 Hz, 1 H), 7.51 (s, 1 H), 7.77 (d, J = 7.52 Hz, 1 H), 7.85 (s, 1 H).
Mass Spec.: (m/z + 1 = 371)

| 4B-74[2] | H | $(CH_3)_2CH(CH_2)_2$— | H H | H | F | H | H | —C(O)$NH_2$ | H | $CH_3$ | F | H |

$^1$H NMR (400 MHz, Methanol-d4) δ ppm 0.99 (d, J = 6.43 Hz, 6 H), 1.68 (s, 3 H), 2.24 (s, 3 H), 3.13-3.19 (m, 2 H), 4.35 (s, 2 H), 7.26 (dd, J = 9.54, 5.81 Hz, 1 H), 7.30 (d, J = 8.09 Hz, 1 H), 7.50 (dd, J = 9.12, 6.01 Hz, 1 H), 7.78 (ddd, J = 7.98, 1.97, 0.41 Hz, 1 H), 7.84 (d, J = 1.24 Hz, 1 H).
Mass Spec.: (m/z + 1 = 371)

| 4B-75[2] | H | indan-2-yl– | H H | H | F | H | H | —C(O)$NH_2$ | H | $CH_3$ | F | H |

$^1$H NMR (400 MHz, Methanol-d4) δ ppm 2.25 (s, 3 H), 3.19-3.27 (m, 2 H), 3.53 (dd, J = 16.38, 7.88 Hz, 2 H), 4.25 (tt, J = 7.88, 6.43 Hz, 1 H), 4.44 (s, 2 H), 7.23-7.32 (m, 6 H), 7.51 (dd, J = 9.12, 6.01 Hz, 1 H), 7.78 (dd, J = 7.88, 1.87 Hz, 1 H), 7.84 (d, J = 1.45 Hz, 1 H.)
Mass Spec.: (m/z + 1 = 393)

TABLE 4B-continued

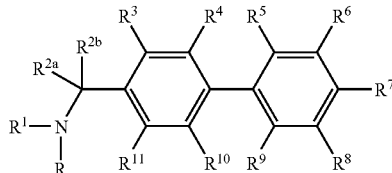

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-76[2] | H | (tetrahydropyran-4-yl-ethyl) | H H | H | H | CH₃ | H | H | —C(O)NH₂ | H | Et | CH₃ | H |

$^1$H NMR (400 MHz, Methanol-d4) δ ppm 1.05 (t, J = 7.58 Hz, 3 H), 1.28 (dd, J = 7.48, 2.70 Hz, 2 H), 1.58-1.69 (m, 5 H), 1.98 (s, 6 H), 2.31 (q, J = 7.68 Hz, 2 H), 3.07-3.16 (m, 2 H), 3.41 (td, J = 1.78, 1.76 Hz, 2 H), 3.92 (dd, J = 1.32, 4.05 Hz, 2 H), 4.17 (s, 2 H), 7.03 (d, J = 7.89 Hz, 1 H), 7.27 (s, 2 H), 7.78 (dd, J = 7.89, 1.87 Hz, 1 H), 7.91 (d, J = 1.45 Hz, 1 H).
Mass Spec.: (m/z + 1 = 395)

| 4B-77[2] | H | (indan-2-yl-methyl) | H H | H | H | Et | H | —C(O)NH₂ | H | H | CH₃ | H |

$^1$H NMR (400 MHz, Methanol-d4) δ ppm 1.02 (t, J = 7.58 Hz, 3 H), 2.08 (s, 3 H), 2.29-2.39 (m, 1 H), 2.43-2.53 (m, 1 H), 3.20 (dd, J = 16.20, 6.85 Hz, 2 H), 3.48 (dd, J = 16.20, 8.10 Hz, 2 H), 4.14-4.22 (m, 1 H), 4.32 (s, 2 H), 7.12 (d, J = 7.89 Hz, 1 H), 7.20-7.24 (m, 3 H) 7.26-7.31 (m, 2 H), 7.43 (dd, J = 7.68, 1.66 Hz, 1 H), 7.49 (s, 1 H), 7.74 (dd, J = 7.89, 1.87 Hz, 1 H), 7.87 (d, J = 1.66 Hz, 1 H).
Mass Spec.: (m/z + 1 = 385)

| 4B-78[2] | H | (tetrahydrofuran-2-yl-methyl) | H H | H | H | H | H | —C(O)NH₂ | H | Cl | Cl | H |

$^1$H NMR (400 MHz, Methanol-d4) δ ppm 1.58-1.67 (m, 1 H), 1.92-2.00 (m, 2 H), 2.09-2.17 (m, 1 H), 2.99-3.06 (m, 1 H), 3.23 (dd, J = 12.77, 2.60 Hz, 1 H), 3.79-3.85 (m, 1 H), 3.89-3.96 (m, 1 H), 4.17-4.24 (m, 1 H), 4.28-4.35 (m, 2 H), 7.39 (dd, J = 11.63, 7.89 Hz, 2 H), 7.56 (dd, J = 7.89, 1.66 Hz, 1 H), 7.74 (d, J = 1.66 Hz, 1 H), 7.86-7.92 (m, 1 H), 8.03 (d, J = 1.66 Hz, 1 H).
Mass Spec.: (m/z + 1 = 379)

| 4B-79[2] | H | (2,2-dimethyl-1,3-dioxolan-4-yl-methyl) | H H | H | H | H | H | —C(O)NH₂ | H | Cl | Cl | H |

$^1$H NMR (400 MHz, Methanol-d4) δ ppm 3.07 (dd, J = 12.67, 9.34 Hz, 1 H), 3.24 (dd, J = 12.56, 3.22 Hz, 1 H), 3.51-3.56 (m, 1 H), 3.58-3.63 (m, 1 H), 3.64 (s, 6 H), 3.92-3.98 (m, 1 H), 4.32 (s, 2 H), 7.40 (dd, J = 12.67, 7.89 Hz, 2 H), 7.56 (dd, J = 7.89, 1.66 Hz, 1 H), 7.74 (d, J = 1.25 Hz, 1 H), 7.88 (dd, J = 7.89, 1.66 Hz, 1 H), 8.03 (d, J = 1.87 Hz, 1 H).
Mass Spec.: (m/z + 1 = 409)

| 4B-80[2] | H | (CH₃)₂CH(CH₂)₂— | H H | F | H | H | H | —C(O)NH₂ | H | Cl | F | H |

$^1$H NMR (400 MHz, Methanol-d4) δ ppm 0.98 (d, J = 6.23 Hz, 6 H), 1.59-1.66 (m, 2 H), 1.67-1.73 (m, 1 H), 3.11-3.18 (m, 2 H), 4.34 (s, 2 H), 7.34 (dd, J = 9.14, 5.81 Hz, 1 H), 7.45-7.51 (m, 2 H), 7.88-7.93 (m, 1 H), 8.05 (d, J = 1.66 Hz, 1 H).
Mass Spec.: (m/z + 1 = 367)

| 4B-81[2] | H | (CH₃)₂CH(CH₂)₂— | H H | F | H | H | H | —C(O)NH₂ | H | Et | H | F |

$^1$H NMR (400 MHz, Methanol-d4) δ ppm 0.98 (d, J = 6.44 Hz, 6 H), 1.11 (t, J = 7.58 Hz, 3 H), 1.61-1.73 (m, 3 H), 2.65 (q, J = 7.48 Hz, 2 H), 3.11-3.19 (m, 2 H), 4.39 (s, 2 H), 7.12-7.17 (m, 2 H), 7.27 (d, J = 7.89 Hz, 1 H), 7.76 (dd, J = 7.89, 1.87 Hz, 1 H), 7.87 (d, J = 1.87 Hz, 1 H).
Mass Spec.: (m/z + 1 = 361)

TABLE 4B-continued

| Comp. No. | R | R¹ | $R^{2a}$ $R^{2b}$ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-82[2] | H | 2-indanyl | H H | H | H | Cl | H | H | —C(O)NH₂ | H | Cl | CH₃ | H |

$^1$H NMR (400 MHz, Methanol-d4) δ ppm 2.09 (s, 3 H), 3.19 (dd, J = 16.30, 6.54 Hz, 2 H), 3.44-3.52 (m, 2 H), 4.14-4.22 (m, 1 H), 4.32 (s, 2 H), 7.21-7.25 (m, 2 H), 7.25-7.34 (m, 3 H), 7.46 (s, 1 H), 7.59 (d, J = 1.04 Hz, 1 H), 7.91 (dd, J = 7.89, 1.87 Hz, 1 H), 8.06 (d, J = 1.45 Hz, 1 H).
Mass Spec.: (m/z + 1 = 425)

| 4B-83[2] | H | (CH₃)₂CH(CH₂)₂— | H H | H | H | Cl | H | H | —C(O)NH₂ | H | CH₃ | CH₃ | H |

$^1$H NMR (400 MHz, Methanol-d4) δ ppm 6.98 (d, J = 6.44 Hz, 6 H), 1.58-1.65 (m, 2 H), 1.70 (ddd, J = 13.39, 6.64, 6.54 Hz, 1 H), 1.99-2.04 (m, 6 H), 3.08-3.13 (m, 2 H), 4.21 (s, 2 H), 7.09 (d, J = 7.89 Hz, 1 H), 7.42 (d, J = 1.04 Hz, 1 H), 7.55 (d, J = 1.25 Hz, 1 H), 7.78 (dd, J = 7.89, 1.45 Hz, 1 H), 7.85 (s, 1 H).
Mass Spec.: (m/z + 1 = 359)

| 4B-84[2] | H | 2-indanyl | H H | H | H | Cl | H | H | —C(O)NH₂ | H | CH₃ | CH₃ | H |

$^1$H NMR (400 MHz, Methanol-d4) δ ppm 2.04 (s, 6 H), 3.20 (dd, J = 16.20, 6.64 Hz, 2 H), 3.48 (dd, J = 16.20, 7.89 Hz, 2 H), 4.18 (t, J = 7.37 Hz, 1 H), 4.32 (s, 2 H), 7.09 (d, J = 7.89 Hz, 1 H), 7.20-7.25 (m, 2 H), 7.26-7.31 (m, 2 H), 7.46 (s, 1 H), 7.59 (d, J = 1.25 Hz, 1 H), 7.78 (dd, J = 7.89, 1.45 Hz, 1 H), 7.85 (s, 1 H).
Mass Spec.: (m/z + 1 = 405)

| 4B-85[2] | H | (CH₃)₂CH(CH₂)₂— | H H | H | H | H | CH₃ | H | —C(O)NH₂ | H | H | H | OBn |

$^1$H NMR (400 MHz, Methanol-d4) δ ppm 0.90 (d, J = 6.44 Hz, 6 H), 1.50-1.62 (m, 3 H), 2.20 (s, 3 H), 3.01-3.06 (m, 2 H), 4.28 (s, 2 H), 5.24 (s, 2 H), 7.00 (d, J = 7.68, 1.45 Hz, 1 H), 7.11 (d, J = 1.45 Hz, 1 H), 7.26 (d, J = 8.10 Hz, 1 H), 7.32-7.42 (m, 3 H), 7.47-7.51 (m, 3 H), 7.73 (dd, J = 7.89, 1.45 Hz, 1 H), 7.78 (d, J = 1.87 Hz, 1 H).
Mass Spec.: (m/z + 1 = 417)

| 4B-86[2] | H | 2-indanyl | H H | H | H | H | CH₃ | H | —C(O)NH₂ | H | H | H | OBn |

$^1$H NMR (400 MHz, Methanol-d4) δ ppm 2.23 (s, 3 H), 3.05 (dd, J = 16.51, 6.13 Hz, 2 H), 3.35 (dd, J = 16.40, 8.10 Hz, 2 H), 4.07-4.14 (m, 1 H), 4.31 (s, 2 H), 5.22 (s, 2 H), 7.01 (dd, J = 7.68, 1.45 Hz, 1 H), 7.13-7.20 (m, 5 H), 7.27 (d, J = 8.10 Hz, 1 H), 7.36-7.44 (m, 3 H), 7.49-7.53 (m, 3 H), 7.73 (dd, J = 7.68, 1.66 Hz, 1 H), 7.79 (d, J = 1.87 Hz, 1 H).
Mass Spec.: (m/z + 1 = 463)

| 4B-87[2] | H | (CH₃)₂CH(CH₂)₂— | H H | H | H | H | H | —C(O)NH₂ | H | CH₃ | H | OH |

$^{11}$H NMR (400 MHz, Methanol-d4) δ ppm 0.96 (d, 6 H), 1.59-1.70 (m, 3 H), 2.29 (s, 3 H), 3.05-3.11 (m, 2 H), 4.24 (s, 2 H), 6.85-6.88 (m, 2 H), 7.25 (d, J = 7.89 Hz, 1 H), 7.36-7.41 (m, 1 H), 7.72 (dd, J = 7.89, 1.45 Hz, 1 H), 7.79 (d, J = 1.45 Hz, 1 H).
Mass Spec.: (m/z + 1 = 337)

| 4B-88[2] | H | 2-indanyl | H H | H | H | H | H | —C(O)NH₂ | H | CH₃ | H | OH |

$^1$H NMR (400 MHz, Methanol-d4) δ ppm 2.29 (s, 3 H), 3.21 (dd, J = 16.20, 6.64 Hz, 2 H), 3.47 (dd, J = 16.20, 7.89 Hz, 2 H), 4.12-4.20 (m, 1 H), 4.31 (s, 2 H), 6.85-6.89 (m, 2 H), 7.22 (td, J = 6.28, 3.01 Hz, 2 H), 7.25-7.30 (m, 3 H), 7.41-7.44 (m, 1 H), 7.72 (d, J = 7.89, 1.45 Hz, 1 H), 7.79 (s, 1 H).
Mass Spec.: (m/z + 1 = 337)

TABLE 4B-continued

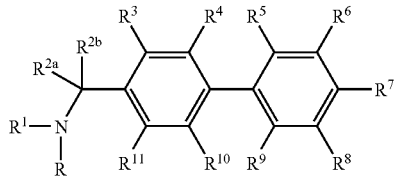

| Comp. No. | R | R¹ | $R^{2a}$ $R^{2b}$ | R³ | R⁴ | R⁵ | R⁶ | R⁷ | R⁸ | R⁹ | R¹⁰ | R¹¹ |
|---|---|---|---|---|---|---|---|---|---|---|---|---|
| 4B-89[2] | H | 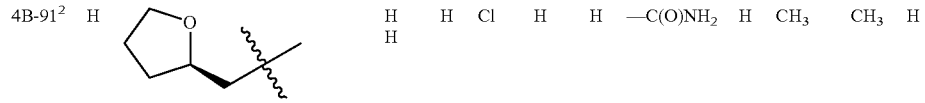 | H H | H | H | H | H | —C(O)NH₂ | H | CH₃ | H | OCH₃ |

$^1$H NMR (400 MHz, Methanol-d4) δd ppm 2.30 (s, 3 H), 3.20 (dd, J = 16.30, 6.33 Hz, 2 H), 3.48 (dd, J = 16.30, 7.99 Hz, 2 H), 3.95 (s, 3 H), 4.13-4.21 (m, 1 H), 4.33 (s, 2 H), 6.99 (dd, J = 7.68, 1.45 Hz, 1 H), 7.05 (d, J = 1.25 Hz, 1 H), 7.20-7.24 (m, 2 H), 7.26-7.32 (m, 3 H), 7.50 (d, J = 7.68 Hz, 1 H), 7.74 (dd, J = 7.89, 1.45 Hz, 1 H), 7.81 (d, J = 1.45 Hz, 1 H).
Mass Spec.: (m/z + 1 = 387)

| 4B-90[2] | H | (CH₃)₂CH(CH₂)₂— | H H | H | H | H | H | —C(O)NH₂ | H | CH₃ | H | CH₃ |

$^1$H NMR (400 MHz, Methanol-d4) δ ppm 0.99 (d, J = 6.43 Hz, 6 H), 1.58-1.65 (m, 2 H), 1.70 (ddd, J = 13.22, 6.84, 6.69 Hz, 1 H), 2.07 (s, 3 H), 2.09 (s, 3 H), 3.07-3.16 (m, 2 H), 4.22 (s, 2 H), 7.14 (d, J = 7.88 Hz, 1 H), 7.19 (d, J = 7.88 Hz, 1 H), 7.38 (dd, J = 7.78, 1.56 Hz, 1 H), 7.44 (s, 1 H), 7.75 (dd, J = 7.88, 1.87 Hz, 1 H), 7.83 (s, 1 H).
Mass Spec.: (m/z + 1 = 325)

| 4B-91[2] | H | 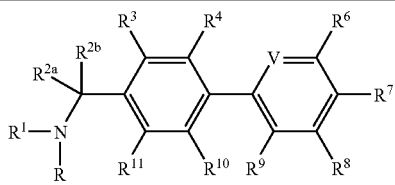 | H H | H | H | Cl | H | H | —C(O)NH₂ | H | CH₃ | CH₃ | H |

$^1$H NMR (400 MHz, Methanol-d4) δ ppm 1.58-1.67 (m, 1 H), 1.91-2.00 (m, 2 H), 2.03 (d, J = 5.61 Hz, 6 H), 2.08-2.20 (m, 1 H), 3.01 (dd, J = 12.77, 10.07 Hz, 1 H), 3.21 (dd, J = 12.77, 2.80 Hz, 1 H), 3.82 (dt, J = 8.31, 6.85 Hz, 1 H), 3.93 (ddd, J = 8.41, 6.85, 6.75 Hz, 1 H), 4.16-4.26 (m, 3 H), 7.09 (d, J = 7.89 Hz, 1 H), 7.42 (d, J = 1.04 Hz, 1 H), 7.55 (d, J = 1.25 Hz, 1 H), 7.78 (dd, J = 7.89, 1.25 Hz, 1 H), 7.85 (s, 1 H).
Mass Spec.: (m/z + 1 = 373)

[1]Isolated and characterized as the free base.
[2]Isolated and characterized as the hydrochloride salt.
[3]Isolated and characterized as the trifluoroacetic acid salt.
"OBn" refers to benzyloxy and "Et" refers to ethyl

TABLE 4C

| Comp. No. | R | R¹ | $R^{2a}$ $R^{2b}$ | R³ | R⁴ | V | R⁶ | R⁷ | R⁸ | R⁹ | R¹⁰ | R¹¹ |
|---|---|---|---|---|---|---|---|---|---|---|---|---|
| 4C-01[2] | H | (CH₃)₂CH(CH₂)₂— | H H | H | H | N | H | —C(O)NH₂ | H | Cl | H | H |

$^1$H NMR (400 MHz, Methanol-d4) δ ppm 0.97 (d, J = 6.44 Hz, 6 H), 1.58-1.63 (m, 2 H), 1.63-1.73 (m, 1 H), 3.08-3.14 (m, 2 H), 4.29 (s, 2 H), 7.65 (d, J = 8.51 Hz, 2 H), 7.83 (d, J = 8.31 Hz, 2 H), 8.48 (d, J = 1.87 Hz, 1 H), 9.04 (d, J = 2.08 Hz, 1 H).
Mass Spec.: (m/z + 1 = 332).

| 4C-02[2] | H | 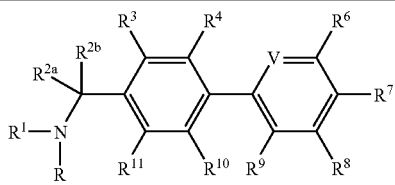 | H H | H | H | N | H | —C(O)NH₂ | H | Cl | H | H |

$^1$H NMR (400 MHz, Methanol-d4) δ ppm 3.20 (dd, J = 16.20, 6.64 Hz, 2 H), 3.49 (dd, J = 16.20, 7.89 Hz, 3 H), 4.15-4.23 (m, 1 H), 4.39 (s, 2 H), 7.21-7.25 (m, 2 H), 7.29 (dd, J = 5.40, 3.32 Hz, TABLE 4C-continued

| Comp. No. | R | R¹ | R$^{2a}$ R$^{2b}$ | R³ | R⁴ | V | R⁶ | R⁷ | R⁸ | R⁹ | R¹⁰ | R¹¹ |
|---|---|---|---|---|---|---|---|---|---|---|---|---|

2 H), 7.68 (d, J = 8.51 Hz, 2 H), 7.84 (d, J = 8.51 Hz, 2 H), 8.45 (d, J = 1.87 Hz, 1 H), 9.03 (d, J = 1.87 Hz, 1 H).
Mass Spec.: (m/z + 1 = 378).

| 4C-03[2] | H | 2,3-dihydro-1H-inden-2-yl | H H | H | H | N | H | —C(O)NH$_2$ | H | CH$_3$ | H | H |

$^1$H NMR (500 MHz, Methanol-d4) δ ppm 2.54 (s, 3 H), 3.26 (dd, J = 16.07, 6.74 Hz, 2 H), 3.53 dd, J = 16.59, 7.78 Hz, 2 H), 4.21-4.27 (m, J = 7.39, 7.39, 7.26, 7.00 Hz, 1 H), 4.49 (s, 2 H), 7.24-7.28 (m, 2 H), 7.30-7.34 (m, 2 H), 7.81 (d, J = 8.03 Hz, 2 H), 7.86 (d, J = 8.03 Hz, 2 H), 8.85 (s, 1 H), 9.10 (s, 1 H).
Mass Spec.: (m/z + 1 = 358).

| 4C-04[2] | H | (CH$_3$)$_2$CH(CH$_2$)$_2$— | H H | H | H | N | H | —C(O)NH$_2$ | H | CH$_3$ | H | H |

$^1$H NMR (500 MHz, Methanol-d4) δ ppm 1.01 (d, J = 6.48 Hz, 6 H), 1.64-1.69 (m, 2 H), 1.73 (d, J = 6.22 Hz, 1 H), 2.54 (s, 3 H), 3.13-3.19 (m, 2 H), 4.38 (s, 2 H), 7.78-7.84 (m, 4 H), 8.87 (s, 1 H), 9.10 (d, J = 1.81 Hz, 1 H).
Mass Spec.: (m/z + 1 = 312).

[1]Isolated and characterized as the free base.
[2]Isolated and characterized as the hydrochloride salt.
[3]Isolated and characterized as the trifluoroacetic acid salt.

Example 5

Preparation of (3'-Carbamoyl-2-fluoro-biphenyl-4-ylmethyl)-(3-methyl-butyl)-ammonium chloride (E5-01)

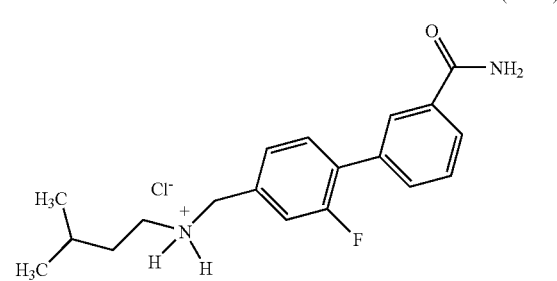

(E5-01)

[(3'-Carbamoyl-2-fluoro-biphenyl-4-ylmethyl)-(3-methyl-butyl)-carbamic acid tert-butyl ester (I-5d): 0.180 g, 0.434 mmol) was dissolved in dichloromethane (10 ml) and treated with 1 ml of a 4M hydrogen chloride solution in dioxane. After 1 hour, the reaction mixture was concentrated under reduced pressure to provide a solid that was titrated with hexanes to afford the title product (E5-01) after filtration.

$^1$H NMR (400 MHz, Methanol-d$_4$) δ ppm 0.97 (d, J=6.64 Hz, 6H), 1.58-1.65 (m, 2H), 1.70 (dt, J=13.34, 6.72 Hz, 1H), 3.07-3.13 (m, 2H), 4.26 (s, 2H), 7.39 (dd, J=6.13, 1.56 Hz, 1H), 7.41-7.43 (m, 1H), 7.56 (t, J=7.79 Hz, 1H), 7.65 (t, J=8.10 Hz, 1H) 7.72-7.75 (m, 1H), 7.90 (dt, J=7.89, 1.45 Hz, 1H), 8.06 (d, J=1.45 Hz, 1H). Mass Spec.: (m/z+1=315)

Example 6

The compounds listed in Table 6A below were prepared using the following general procedures with the appropriate starting materials which are available commercially, prepared using preparations well-known to those skilled in the art, or prepared in a manner analogous to routes described above for other intermediates.

The corresponding amine monomer (0.2 mmol) was weighed into an 8 mL round-bottomed vial followed by the addition of 2'-chloro-4'-formyl-biphenyl-3-carboxylic acid amide (0.4 mL of a 0.15 M solution in 1:1 THF/DMSO containing 2% acetic acid). After shaking the vials for 5 minutes, sodium triacetoxyborohydride (0.4 mL of a 1M suspension in 1:1 THF/DMSO) was added. The vials were then capped and shaken for 24 hours at ambient temperature before an aqueous solution of sodium carbonate (0.5 mL of a 2M solution) was added. After 45 minutes, the aqueous phase was extracted twice with 2 mL of ethyl acetate. The combined organic phases were concentrated under vacuum to afford a residue. The residue was dissolved in 1 mL of DMSO and purified by HPLC (Waters XTerra PrepMS C18 OBD, 5 μm, 19×100 mm steel column, eluting at 20 mL/min, with a 95:5 water/acetonitrile solution containing 0.1% trifluoroacetic acid for 1 minute followed by a gradient ending with a 5:95 water/acetonitrile solution containing 0.1% trifluoroacetic acid at 7 minutes. The compounds below eluted at the indicated retention times, given in minutes.

TABLE 6A

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 6A-01[3] | H | CH₃CH₂O(CH₂)₂— | H H | H | Cl | H | H | H | —C(O)NH₂ | H | H | H |
| | Mass Spec. (m/z + 1 = 333). Retention Time = 2.46 | | | | | | | | | | | |
| 6A-02[3] | H | 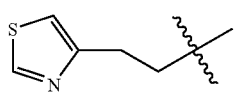 | H H | H | Cl | H | H | H | —C(O)NH₂ | H | H | H |
| | Mass Spec. (m/z + 1 = 372). Retention Time = 2.45 | | | | | | | | | | | |
| 6A-03[3] | H | 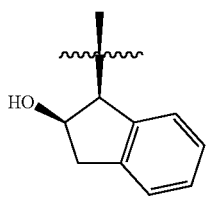 | H H | H | Cl | H | H | H | —C(O)NH₂ | H | H | H |
| | Mass Spec. (m/z + 1 = 393). Retention Time = 2.63 | | | | | | | | | | | |
| 6A-04[3] | H | 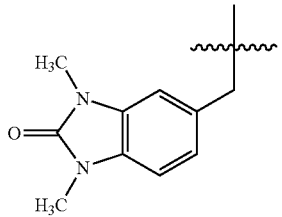 | H H | H | Cl | H | H | H | —C(O)NH₂ | H | H | H |
| | Mass Spec. (m/z + 1 = 435). Retention Time = 2.52 | | | | | | | | | | | |
| 6A-05[3] | H | 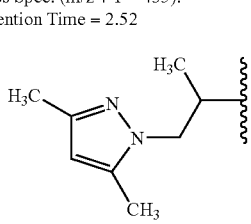 | H H | H | Cl | H | H | H | —C(O)NH₂ | H | H | H |
| | Mass Spec. (m/z + 1 = 397). Retention Time = 2.68 | | | | | | | | | | | |
| 6A-06[3] | H | 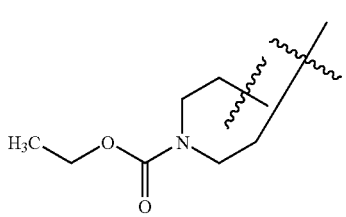 | H H | H | Cl | H | H | H | —C(O)NH₂ | H | H | H |
| | Mass Spec. (m/z + 1 = 402). Retention Time = 2.49 | | | | | | | | | | | |

TABLE 6A-continued

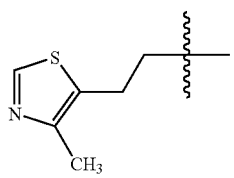

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 6A-07[3] | H | CH₃O(CH₂)₂— | H H | H | Cl | H | H | H | —C(O)NH₂ | H | H | H |
| | Mass Spec. (m/z + 1 = 319). Retention Time = 2.33 | | | | | | | | | | | |
| 6A-08[3] | H | 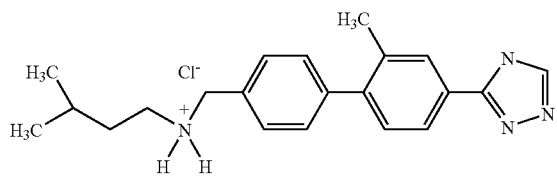 | H H | H | Cl | H | H | H | —C(O)NH₂ | H | H | H |
| | Mass Spec. (m/z + 1 = 386). Retention Time = 2.32 | | | | | | | | | | | |

[3]Isolated and characterized as the trifluoroacetic acid salt.

Example 7

Preparation of [2'-methyl-4'-(4H-[1,2,4]-triazol-3-yl)-biphenyl-4-ylmethyl]-(3-methyl-butyl)-amine hydrochloride (E7-01)

(E7-01)

(4'-{[1-Dimethylamino-methylidene]-carbamoyl}-2'-methyl-biphenyl-4-ylmethyl)-(3-methyl-butyl)-carbamic acid tert-butyl ester (I-7a-1: 222 mg, 0.477 mmol) was dissolved in acetic acid (5 ml) and treated with hydrazine monohydrate (0.035 ml, 0.715 mmol). After the reaction mixture was heated at 90° C. for 2 hours, the volatiles were removed and the residue was taken up in ethyl acetate and washed with a saturated aqueous sodium bicarbonate solution. The organic phase was dried over sodium sulfate, filtered and concentrated under reduced pressure. The residue was purified using preparative thin layer chromatography eluting with 50% ethyl acetate in hexanes. The product-containing band was isolated and extracted, and the extracts were concentrated under reduced pressure to afford a residue. The residue was dissolved in methanol and treated with 4M HCl in dioxane. After 2 hours, the volatiles were removed under reduced pressure and the resulting solid triturated with hexanes to provide a suspension. The solid was isolated by filtration to afford the title compound (E7-01) as a colorless solid.

¹H NMR (400 MHz, Methanol-4) δ ppm 0.95 (d, J=6.43 Hz, 6H), 1.56-1.63 (m, 2H), 1.64-1.69 (m, 1H), 2.33 (s, 3H), 3.06-3.11 (m, 2H), 4.25 (s, 2H), 7.40 (d, J=7.88 Hz, 1H), 7.46 (d, J=8.09 Hz, 2H), 7.59 (d, J=8.09 Hz, 2H), 7.87 (dd, J=7.99, 1.97 Hz, 1H), 7.94 (s, 1H), 9.19 (s, 1H). Mass Spec.: (m/z+1=335).

Preparation of [2-Fluoro-3'-(4H-[1,2,4]-triazol-3-yl)-biphenyl-4-ylmethyl]-(3-methyl-butyl)-amine hydrochloride salt (E7-02)

(E7-02)

[3'-(Dimethylaminomethylene-carbamoyl)-2-fluoro-biphenyl-4-ylmethyl]-(3-methyl-butyl)-carbamic acid tert-butyl ester (I-7a-2: 0.90 g, 1.9 mmol) and hydrazine monohydrate (0.102 mL, 2.11 mmol) were combined in 6 mL of acetic acid and heated to 90° C. After 2 hours, the reaction mixture was cooled to room temperature and the volatiles were removed under reduced pressure. The resulting residue was taken up in ethyl acetate and washed sequentially with a saturated aqueous sodium bicarbonate solution and brine, dried over sodium sulfate, filtered and concentrated. The residue was purified by chromatography using silica gel and eluting with 40% ethyl acetate in hexanes to afford the corresponding BOC-protected material. The BOC-protected material was dissolved in dichloromethane (100 mL) and treated with 4.0M HCl in dioxane (10 mL). After 2 hours, the volatiles were removed under reduced pressure and the resulting solid triturated with hexanes to provide a suspension. The solid was isolated by filtration to afford the title compound (E7-02) as a colorless solid (0.60 g, 83%)

¹H NMR (400 MHz, Methanol-d₄) δ ppm 0.98 (d, J=6.44 Hz, 6H), 1.58-1.66 (m, 2H), 1.69 (dd, J=13.29, 6.64 Hz, 1H), 3.08-3.14 (m, 2H), 4.28 (s, 2H), 7.42-7.48 (m, 2H), 7.70 (td, J=7.89, 2.70 Hz, 2H), 7.80 (dd, J=7.89, 1.25 Hz, 1H), 8.06 (dt, J=7.68, 1.45 Hz, 1H), 8.24 (d, J=1.45 Hz, 1H), 9.19 (s, 1H). Mass Spec.: (m/z+1=339)

The compounds listed in Tables 7A and 7B below were prepared using procedures analogous to those described above for the synthesis of (3-Methyl-butyl)-[2'-methyl-4'-(4H-[1,2,4]trizol-3-yl)-biphenyl-4-ylmethyl]-ammonium chloride (E7-01) and [2-Fluoro-3'-(4H-[1,2,4]triazol-3-yl)-biphenyl-4-ylmethyl]-(3-methyl-butyl)-amine (E7-02) using the appropriate starting materials which are available commercially, prepared using preparations well-known to those skilled in the art, or prepared in a manner analogous to routes described above for other intermediates.

TABLE 7A

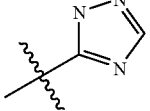

| Comp. No. | R | R¹ | R²ᵃ R²ᵇ | R³ | R⁴ | R⁵ | R⁶ | R⁷ | R⁸ | | R⁹ | R¹⁰ | R¹¹ |
|---|---|---|---|---|---|---|---|---|---|---|---|---|---|
| 7A-01² | H | (CH₃)₂CH(CH₂)₂— | H H | H | H | H | H | H | | 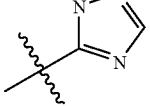 | H | H | H |

¹H NMR (400 MHz, Methanol-d4) δ ppm 0.97 (d, J = 6.44 Hz, 6 H), 1.58-1.65 (m, 2 H), 1.66-1.71 (m, J = 13.19, 6.54 Hz, 1 H), 3.07-3.12 (m, 2 H), 4.27 (s, 2 H), 7.64 (d, J = 8.31 Hz, 2 H), 7.70 (t, J = 7.79 Hz, 1 H), 7.84 (d, J = 8.51 Hz, 2 H), 7.90-7.93 (m, 1 H), 8.03 (dt, J = 7.84, 1.38 Hz, 1 H), 8.34 (1, J = 1.56 Hz, 1 H), 9.26 (s, 1 H).
Mass Spec. (m/z + 1 = 321).

| 7A-02² | H | (CH₃)₂CH(CH₂)₂— | H H | H | H | F | H | H | | 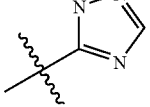 | H | H | H |

¹H NMR (400 MHz, Methanol-d4) δ ppm 0.98 (d, J = 6.44 Hz, 6 H), 1.59-1.65 (m, 2 H), 1.66-1.72 (m, J = 13.08, 6.64 Hz, 1 H), 2.25 (s, 3 H), 3.06-3.13 (m, 2 H), 4.24 (s, 2 H), 7.37 (d, J = 7.89 Hz, 1 H), 7.43-7.47 (m, 2 H), 7.49 (d, J = 3.74 Hz, 1 H), 7.97 (dd, J = 6.75, 2.39 Hz, 1 H), 8.11 (ddd, J = 8.62, 4.67, 2.28 Hz, 1 H), 9.35 (s, 1 H),
Mass Spec. (m/z + 1 = 354).

| 7A-03² | H | (CH₃)₂CH(CH₂)₂— | H H | H | H | F | H | H | | 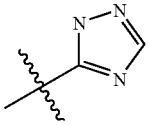 | H | F | H |

¹H NMR (400 MHz, Methanol-d4) δ ppm 0.98 (d, J = 6.44 Hz, 6 H), 1.59-1.65 (m, 2 H), 1.67-1.72 (m, 1 H), 3.09-3.15 (m, 2 H), 4.29 (s, 2 H), 7.44-7.50 (m, 3 H), 7.62 (t, J = 7.68 Hz, 1 H), 8.11-8.15 (m, 2 H), 9.16 (s, 1 H).
Mass Spec. (m/z + 1 = 357).

| 7A-04² | H | (CH₃)₂CH(CH₂)₂— | H H | H | H | H | H | H | | | H | Cl | H |

¹H NMR (400 MHz, METHANOL-d4) δ ppm 0.98 (d, J = 6.64 Hz, 6 H) 1.59-1.65 (m, 2 H) 1.67-1.74 (m, 1 H) 3.08-3.14 (m, 2 H) 4.27 (s, 2 H) 7.54-7.57 (m, 2 H) 7.63-7.71 (m, 2 H) 7.74 (s, 1 H) 8.07 (ddd, J = 7.16, 1.87, 1.77 Hz, 1 H) 8.10-8.11 (m, 1 H) 9.15 (s, 1 H).
Mass Spec. (m/z + 1 = 355).

TABLE 7A-continued

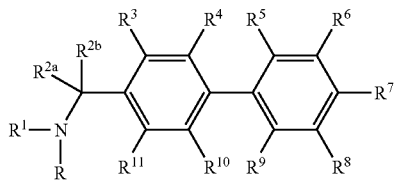

| Comp. No. | R | R¹ | R²ᵃ R²ᵇ | R³ | R⁴ | R⁵ | R⁶ | R⁷ | R⁸ | | R⁹ | R¹⁰ | R¹¹ |
|---|---|---|---|---|---|---|---|---|---|---|---|---|---|
| 7A-05[2] | H | $(CH_3)_2CH(CH_2)_2$— | H H | H | H | $H_3$ | H | H | H | 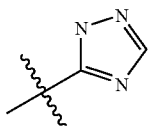 | H | H | H |

$^1$H NMR (400 MHz, METHANOL-d4) δ ppm 0.98 (d, J = 6.44 Hz, 6 H) 1.58-1.64 (m, 2 H) 1.66-1.73 (m, 1 H) 2.33 (s, 3 H) 3.07-3.12 (m, 2 H) 4.22 (s, 2 H) 7.35-7.38 (m, 1 H) 7.39-7.42 (m, 1 H) 7.45 (s, 1 H) 7.54 (dt, J = 7.68, 1.45 Hz, 1 H) 7.66 (t, J = 7.68 Hz, 1 H) 7.98 (t, J = 1.45 Hz, 1 H) 8.03 (dt, J = 7.89, 1.45 Hz, 1 H) 9.08 (s, 1 H)
Mass Spec. (m/z + 1 = 335).

| 7A-06[2] | H | $(CH_3)_2CH(CH_2)_2$— | H H | H | H | F | H | H | H | 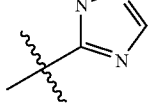 | H | F | H |

$^1$H NMR (400 MHz, METHANOL-d4) δ ppm 0.98 (d, J = 6.44 Hz, 6 H) 1.61-1.66 (m, 2 H) 1.68-1.75 (m, 1 H) 3.10-3.15 (m, 2 H) 4.29 (s, 2 H) 7.32-7.37 (m, 2 H) 7.69-7.76 (m, 2 H) 8.10 (dt, J = 7.32, 1.74 Hz, 1 H) 8.14 (s, 1 H) 9.32 (s, 1 H)
Mass Spec. (m/z + 1 = 357).

[1] Isolated and characterized as the free base.
[2] Isolated and characterized as the hydrochloride salt.
[3] Isolated and characterized as the trifluoroacetic acid salt.

TABLE 7B

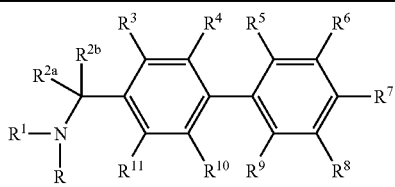

| Comp. No. | R | R¹ | R²ᵃ R²ᵇ | R³ | R⁴ | R⁵ | R⁶ | R⁷ | | R⁸ | R⁹ | R¹⁰ | R¹¹ |
|---|---|---|---|---|---|---|---|---|---|---|---|---|---|
| 7B-01[2] | H | $(CH_3)_2CH(CH_2)_2$— | H H | H | H | H | H | H | 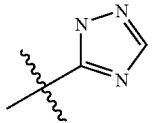 | H | H | H | H |

$^1$H NMR (400 MHz, Methanol-d4) δ ppm 0.97 (d, J = 6.44 Hz, 6 H), 1.58-1.64 (m, 2 H), 1.68 d, J = 6.23 Hz, 1 H), 3.07-3.12 (m, 2 H), 4.26 (s, 2 H), 7.63 (d, J = 8.31 Hz, 2 H), 7.84 (d, J = 8.31 Hz, 2 H), 7.91 (d, J = 8.72 Hz, 2 H), 8.12 (d, J = 8.72 Hz, 2 H), 9.28 (s, 1 H).
Mass Spec. (m/z + 1 = 321).

| 7B-02[2] | H | $(CH_3)_2CH(CH_2)_2$— | H H | H | $CH_3$ | H | H | | 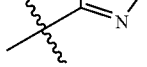 | H | H | H | H |

TABLE 7B-continued

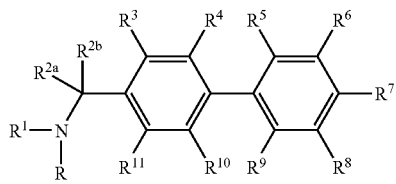

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|

¹H NMR (400 MHz, Methanol-d4) δ ppm 0.97 (d, J = 6.44 Hz, 6 H), 1.60-1.71 (m, 3 H), 2.33 (s, 3 H), 3.06-3.12 (m, 2 H), 4.23 (s, 2 H), 7.35 (d, J = 7.89 Hz, 1 H), 7.44 (d, J = 8.10 Hz, 1 H), 7.49 (s, 1 H), 7.60 (d, J = 8.31 Hz, 2 H), 8.11 (d, J = 8.31 Hz, 2 H), 9.54 (s, 1 H). Mass Spec. (m/z + 1 = 335).

| 7B-03[2] | H | (CH₃)₂CH(CH₂)₂— | H H | H | F | CH₃ | H | [triazole] | H | H | H | H |

¹H NMR (400 MHz, Methanol-d4) δ ppm 0.96 (d, J = 6.43 Hz, 6 H), 1.58-1.70 (m, 3 H), 2.26 (s, 3 H), 3.07-3.13 (m, 2 H), 4.27 (s, 2 H), 7.39-7.46 (m, 4 H), 7.90 (dd, J = 7.88, 1.87 Hz, 1 H), 7.96 (d, J = 1.87 Hz, 1 H), 9.36 (s, 1 H). Mass Spec. (m/z + 1 = 353).

| 7B-04[2] | H | (CH₃)₂CH(CH₂)₂— | H H | H | F | H | H | [triazole] | H | H | H | H |

¹H NMR (400 MHz, Methanol-d4) δ ppm 0.95 (d, J = 6.43 Hz, 6 H), 1.56-1.63 (m, 2 H), 1.67 (dd, J = 13.07, 6.64 Hz, 1 H), 3.06-3.11 (m, 2 H), 4.25 (s, 2 H), 7.40-7.44 (m, 2 H), 7.66 (t, J = 8.09 Hz, 1 H), 7.77 (dd, J = 8.61, 1.56 Hz, 2 H), 8.10 (d, J = 8.51 Hz, 2 H), 9.19 (s, 1 H). Mass Spec. (m/z + 1 = 339).

| 7B-05[2] | H | (CH₃)₂CH(CH₂)₂— | H H | H | H | CF₃ | H | [triazole] | H | H | H | H |

¹H NMR (400 MHz, Methanol-d4) δ ppm 0.95 (d, J = 6.43 Hz, 6 H), 1.56-1.63 (m, 2 H), 1.67 (dd, J = 13.07, 6.43 Hz, 1 H), 3.05-3.11 (m, 2 H), 4.26 (s, 2 H), 7.45 (d, J = 7.88 Hz, 2 H), 7.54-7.60 (m, 3 H), 8.30 (dd, J = 7.99, 1.56 Hz, 1 H), 8.46 (d, J = 1.87 Hz, 1 H), 9.17 (s, 1 H). Mass Spec. (m/z + 1 = 389).

[1] Isolated and characterized as the free base.
[2] Isolated and characterized as the hydrochloride salt.
[3] Isolated and characterized as the trifluoroacetic acid salt.

Example 8

Preparation of (4'-Methenesulfonylamino-2-methyl-biphenyl-4-ylmethyl)-(3-methyl-butyl)-ammonium chloride (E8-01)

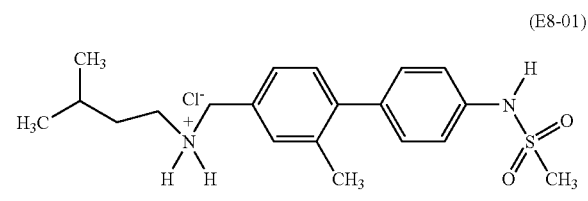

(E8-01)

(4'-Methanesulfonylamino-2-methyl-biphenyl-4-ylmethyl)-(3-methyl-butyl)-carbamic acid tert-butyl ester (I-8c: 0.140 g, 0.304 mmol) was dissolved in methanol (5 ml) and treated with 4M hydrogen chloride in dioxane (1 mL). After stirring for 12 hours, the volatiles were removed under reduced pressure and the resulting solid was titrated with hexanes and isolated by filtration to provide the title compound (E8-01: 86 mg) as a colorless solid.

¹H NMR (400 MHz, Methanol-d4) δ ppm 0.97 (d, J=6.44 Hz, 6H), 1.57-1.63 (m, 2H), 1.64-1.72 (m, J=6.64 Hz, 1H), 2.30 (s, 3H), 2.99 (s, 3H), 3.04-3.10 (m, 2H), 4.19 (s, 2H), 7.26-7.35 (m, 6H), 7.39 (s, 1H). Mass Spec.: (m/z+1=361)

The compounds listed in Tables 8A and 8B below were prepared using procedures analogous to those described above for the synthesis of (4'-Methanesulfonylamino-2-methyl-biphenyl-4-ylmethyl)-(3-methyl-butyl)-ammonium chloride (E8-01) using the appropriate starting materials which are available commercially, prepared using preparations well-known to those skilled in the art, or prepared in a manner analogous to routes described above for other intermediates.

TABLE 8A

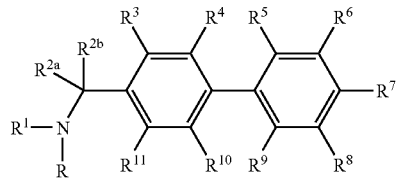

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 8A-01[2] | H | $(CH_3)_2CH(CH_2)_2$— | H H | H | H | H | H | H | —$NHSO_2CH_3$ | H | H | H |
| 8A-02[2] | H | $(CH_3)_2CH(CH_2)_2$— | H H | H | H | H | H | H | —$NHSO_2CH_3$ | H | $CH_3$ | H |
| 8A-03[1] | H | $(CH_3)_2CH(CH_2)_2$— | H H | H | H | H | H | H | —$NHSO_2CH_3$ | H | CN | H |

8A-01: ¹H NMR (400 MHz, DMSO-d6) δ ppm 0.85 (d, J = 6.44 Hz, 6 H), 1.49-1.55 (m, 2 H), 1.57-1.62 (m, 1 H), 2.90 (s, 2 H), 3.01 (s, 3 H), 4.15 (s, 2 H), 7.20 (dt, J = 7.27, 1.97 Hz, 1 H), 7.37-7.46 (m, 3 H), 7.59-7.67 (m, 4 H), 9.04 (s, 2 H), 9.86 (s, 1 H). Mass Spec. (m/z + 1 = 347).

8A-02: ¹H NMR (400 MHz, Methanol-d4) δ ppm 0.97 (d, J = 6.44 Hz, 6 H), 1.56-1.63 (m, 2 H), 1.69 (dt, J = 13.29, 6.64 Hz, 1 H), 2.29 (s, 3 H), 2.96 (s, 3 H), 3.05-3.11 (m, 2 H), 4.19 (s, 2 H), 7.07 (ddd, J = 7.84, 1.30, 1.04 Hz, 1 H), 7.20-7.23 (m, 2 H), 7.28-7.31 (m, 1 H), 7.33-7.37 (m, 1 H), 7.38-7.43 (m, 2 H). Mass Spec. (m/z + 1 = 360).

8A-03: ¹H NMR (400 MHz, Methanol-d4) δd ppm 0.91 (d, J = 6.64 Hz, 6 H), 1.40-1.48 (m, 2 H), 1.56-1.68 (m, J = 13.44, 6.67, 6.67 Hz, 1 H), 2.58-2.67 (m, 2 H), 3.01 (s, 3 H), 3.85 (s, 2H), 7.28-7.33 (m, 2 H), 7.45 (d, J = 7.68 Hz, 1 H), 7.47-7.50 (m, 1 H), 7.55 (d, J = 7.89 Hz, 1 H), 7.71 (dd, J = 7.99, 1.76 Hz, 1 H), 7.83 (d, J = 1.45 Hz, 1 H). Mass Spec. (m/z + 1 = 372).

[1] Isolated and characterized as the free base.
[2] Isolated and characterized as the hydrochloride salt.

TABLE 8B

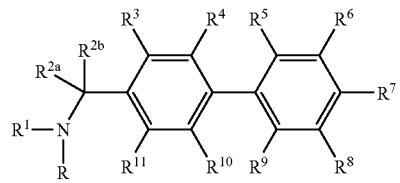

| Comp. No. | R | R¹ | R²ᵃ R²ᵇ | R³ | R⁴ | R⁵ | R⁶ | R⁷ | R⁸ | R⁹ | R¹⁰ | R¹¹ |
|---|---|---|---|---|---|---|---|---|---|---|---|---|
| 8B-01[2] | H | $(CH_3)_2CH(CH_2)_2$— | H H | H | H | $CH_3$ | H | —$NHSO_2CH_3$ | H | H | H | H |
| 8B-02[2] | H | (indanyl) | H H | H | F | H | H | —$NHSO_2CH_3$ | H | H | H | H |

8B-01: ¹H NMR (400 MHz, Methanol-d4) δ ppm 0.97 (d, J = 6.64 Hz, 6 H), 1.55-1.64 (m, 2 H), 1.64-1.74 (m, J = 6.64 Hz, 1 H), 2.22 (s, 3 H), 2.97 (s, 3 H), 3.02-3.15 (m, 2 H), 4.24 (s, 2 H), 7.14-7.15 (m, 2 H), 7.16 (s, 1 H), 7.34-7.46 (m, 2 H), 7.54 (d, J = 8.31 Hz, 2 H). Mass Spec. (m/z + 1 = 361).

8B-02: ¹H NMR (400 MHz, Methanol-d4) δ ppm 2.99 (s, 3 H), 3.19 (dd, J = 16.40, 6.44 Hz, 2 H), 3.50 dd, J = 16.30, 7.79 Hz, 2 H), 4.16-4.23 (m, 1 H), 4.39 (s, 2 H), 7.20-7.25 (m, 2 H), 7.29 (dd, J = 5.40, 3.32 Hz, 2 H), 7.35 (d, J = 8.93 Hz, 2 H), 7.52-7.58 (m, 2 H), 7.61 (d, J = 7.89 Hz, 1 H), 7.66 (d, J = 8.93 Hz, 2 H). Mass Spec. (m/z + 1 = 441).

[2] Isolated and characterized as the hydrochloride salt.

Pharmacological Testing

The practice of the instant invention for treating obesity or related eating disorders (including promoting weight loss or reducing weight gain) can be evidenced by activity in at least one of the protocols described hereinbelow.

In Vitro Biological Assays

Binding Assay

The test compounds where diluted in 100% DMSO ($10^{-10}$ M to $10^{-5}$ M) and then 2 µl were added to a 96 well polypropylene plate. 2 µl 10 µM of Naltrexone were added onto the plate for non-specific activity. [$^3$H] Diprenorphine (DPN) was diluted in binding buffer (50 mM Tris-HCL (pH7.5), 5 mM $MgCl_2$, 1 mM EDTA followed by protease inhibitors: 100 µg/ml bacitracin, 100 µg/ml benzamidine, 5 µg/ml aprotinin, 5 µg/ml leupeptin) and 20 µl were added to the plate. Membranes prepared from cells expressing recombinant delta, kappa and mu opioid receptors were diluted with binding buffer and 178 µl were added to the plate. The plates were covered and placed on an orbital shaker at room temperature for 60 minutes. At the end of incubation, the plates were then harvested onto GF/C filter plates (Perkin Elmer, presoaked with 1% PEI) using ice-cold binding buffer. Each filter was washed three times. The filters were dried overnight. In the morning, 30 µl of scintillation cocktail were added onto the well and sealed. The plates were counted on a Wallac Trilux™ counter. Ki were determined by using Cheng and Prusoff equation within PRISM software. Kd values were obtained from Scatchard plot analysis.

The following bioassay system for determining the mu, kappa and delta binding properties and pharmacological activity of opioid ligands is described by Bass, R., et al., in "Identification and characterization of novel somatostatin antagonists" *Molecular Pharmacology*, 50, 709-715 (1996), which is incorporated herein by reference.

GTPγ[$^{35}$] Binding Assays at Opioid Receptors

Membranes were prepared from cells as described (Bass et al, 1996). GTPγ[5S] binding assays were performed in a 96 well FlashPlate™ format in duplicate using 100 µM GTPγ [$^{35}$S] and 5 µg membrane per well in assay buffer composed of 50 mM Tris HCl, pH 7.4, 5 mM $MgCl_2$, 1 mM EDTA, 100 mM NaCl, 30 µM GDP, 0.1% bovine serum albumin and the following protease inhibitors: 100 µg/ml bacitracin, 100 µg/ml benzamidine, 5 µg/ml aprotinin, 5 µg/ml leupeptin. The assay mix was then incubated at 30° C. with increasing concentrations of antagonist ($10^{-10}$ M to $10^{-5}$ M) for 10 minutes and challenged with the agonists BW-373U86 (1 nM), dynorphin-A (10 nM), 1-endorphin (1 µM) for opioid receptors delta, kappa, and mu, respectively. The assays were performed at 30° C. for one hour. The FlashPlates were then centrifuged at 2000×g for 10 minutes. Stimulation of GTPγ [$^{35}$S] binding was then quantified using a Wallac Microbeta and Ki calculations were done using Prism™ by Graphpad. The average Ki values observed for the compounds listed in the Example section above are summarized in the Table below for each of the receptors; mu, kappa and delta.

| | | GTPγ[$^{35}$S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| E1-01 | 3',5'-difluoro-2-methyl-4'-{[(3-methylbutyl)amino]-methyl}biphenyl-4-carboxamide, hydrochloride salt | 2.1 | 7 | 2.64 | 7 | 1.7 | 7 |
| 1A-01 | 2'-methyl-4'-{[(3-methylbutyl)amino]-methyl}biphenyl-3-carboxamide, hydrochloride salt | 1.49 | 5 | 11.5 | 5 | ND | — |
| 1A-02 | 2',6'-dimethyl-4'-{[(3-methylbutyl)-amino]-methyl}-biphenyl-3-carboxamide, hydrochloride salt | 1.25 | 2 | 6.72 | 2 | 2.59 | 2 |
| 1A-03 | 2',6'-dichloro-4'-{[(3-methylbutyl)-amino]-methyl}-biphenyl-3-carboxamide, hydrochloride salt | 1.2 | 2 | 3.76 | 3 | 4.87 | 1 |
| 1A-04 | 2'-cyano-4'-{[(3-methylbutyl)amino]-methyl}biphenyl-3-carboxamide, hydrochloride salt | 4.64 | 2 | 28.8 | 2 | 13.8 | 1 |
| 1A-05 | 3'-methoxy-4'-{[(3-methylbutyl)amino]-methyl}biphenyl-3-carboxamide, hydrochloride salt | 14 | 1 | 16.6 | 1 | 10.7 | 1 |
| 1A-06 | 3'-hydroxy-4'-{[(3-methylbutyl)amino]-methyl}biphenyl-3-carboxamide | 52.3 | 1 | 101 | 1 | 0.0351 | 1 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 1A-07 | 2',6-difluoro-4'-{[(3-methylbutyl)amino]-methyl}biphenyl-3-carboxamide, hydrochloride salt | 14.5 | 4 | 14.3 | 6 | 9.49 | 4 |
| 1A-08 | 3',5'-difluoro-4'-{[(3-methylbutyl)amino]-methyl}biphenyl-3-carboxamide, hydrochloride salt | 70.9 | 2 | 87.3 | 4 | 3160 | 2 |
| 1A-09 | 3',5',6-trifluoro-4'-{[(3-methylbutyl)-amino]-methyl}-biphenyl-3-carboxamide, hydrochloride salt | 64.8 | 2 | 51.1 | 4 | 16.7 | 2 |
| 1A-10 | 4'-[(2,3-dihydro-1H-inden-2-ylamino)-methyl]-3',5'-difluorobiphenyl-3-carboxamide, hydrochloride salt | 0.966 | 2 | 14.4 | 2 | 5.5 | 2 |
| 1A-11 | 4'-[(2,3-dihydro-1H-inden-2-ylamino)-methyl]-3',5',6-trifluorobiphenyl-3-carboxamide, hydrochloride salt | 0.843 | 2 | 12.4 | 2 | 6.62 | 2 |
| 1A-12 | 3',6-difluoro-4'-{[(3-methylbutyl)amino]-methyl}biphenyl-3-carboxamide, hydrochloride salt | 41.1 | 2 | 34.9 | 2 | 17.2 | 2 |
| 1A-13 | 3'-chloro-4'-{[(3-methylbutyl)amino]-methyl}biphenyl-3-carboxamide, hydrochloride salt | 25 | 3 | 23.4 | 3 | 33.6 | 3 |
| 1B-01 | 2'-methyl-4'-{[(3-methylbutyl)amino]-methyl}biphenyl-4-carboxamide, hydrochloride salt | 17.8 | 2 | 24.8 | 2 | 13.6 | 2 |
| 1B-02 | 2'-fluoro-4'-{[(3-methylbutyl)amino]-methyl}biphenyl-4-carboxamide, hydrochloride salt | 144 | 2 | 54.2 | 2 | 504 | 2 |
| 1B-03 | 2'-fluoro-2-methyl-4'-{[(3-methylbutyl)-amino]-methyl}-biphenyl-4-carboxamide, hydrochloride salt | 8.96 | 3 | 3.32 | 3 | 5.09 | 3 |
| 1B-04 | 2',6'-difluoro-4'-(indan-2-ylaminomethyl)-2-methyl-biphenyl-4-carboxylic acid amide, hydrochloride salt | 2.66 | 2 | 20.1 | 2 | 5.28 | 2 |
| 1B-05 | 3',5'-difluoro-4'-{[(3-methylbutyl)amino]-methyl}biphenyl-4-carboxamide, hydrochloride salt | 107 | 1 | 162 | 1 | 3000 | 1 |
| 1B-06 | 4'-[(2,3-dihydro-1H-inden-2-ylamino)-methyl]-2'-fluoro-2-methylbiphenyl-4-carboxamide, hydrochloride salt | 0.108 | 2 | 0.372 | 2 | 0.164 | 2 |
| 1B-07 | 4'-[(2,3-dihydro-1H-inden-2-ylamino)-methyl]-3',5'-difluoro-2-methyl-biphenyl-4-carboxamide, hydrochloride salt | 0.0494 | 2 | 0.241 | 2 | 0.0993 | 2 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 1B-08 | 3'-fluoro-2-methyl-4'-{[(3-methylbutyl)-amino]-methyl}-biphenyl-4-carboxamide, hydrochloride salt | 3.24 | 2 | 1.89 | 2 | 1.97 | 2 |
| 1B-09 | 3',5'-difluoro-4'-{[(2-methoxyethyl)-amino]-methyl}-2-methylbiphenyl-4-carboxamide | 70.5 | 3 | 17.9 | 3 | 11 | 3 |
| 1B-10 | 4'-[(2,3-dihydro-1H-inden-2-ylamino)-methyl]-3'-fluoro-2-methylbiphenyl-4-carboxamide, hydrochloride salt | 0.0717 | 3 | 0.256 | 3 | 0.0326 | 3 |
| 1C-01 | 3-(6-{[(3-methyl-butyl)amino]-methyl}pyridin-3-yl)benzamide, hydrochloride salt | 154 | 2 | 114 | 2 | 22 | 2 |
| 1D-01 | 3-methyl-4-(6-{[(3-methylbutyl)amino]-methyl}pyridin-3-yl)benzamide, hydrochloride salt | 20.5 | 2 | 17.1 | 2 | 11.7 | 2 |
| 1D-02 | 3-methyl-4-(5-{[(3-methylbutyl)amino]-methyl}pyridin-2-yl)benzamide, hydrochloride salt | 43.1 | 3 | 14.7 | 3 | 4.33 | 3 |
| 1D-03 | 4-{5-[(2,3-dihydro-1H-inden-2-yl-amino)-methyl]-pyridin-2-yl}-3-methylbenzamide, hydrochloride salt | 0.541 | 4 | 2.93 | 4 | 1.24 | 4 |
| 1D-04 | 4-{6-[(2,3-dihydro-1H-inden-2-yl-amino)-methyl]-pyridin-3-yl}-3-methylbenzamide, hydrochloride salt | 0.715 | 4 | 1.88 | 4 | 0.868 | 4 |
| 1D-05 | 3-chloro-4-{6-[(2,3-dihydro-1H-inden-2-yl-amino)-methyl]pyridin-3-yl}-benzamide, hydrochloride salt | 1.85 | 2 | 4.96 | 2 | 4.85 | 2 |
| 1D-06 | 3-chloro-4-{5-[(2,3-dihydro-1H-inden-2-ylamino)-methyl]pyridin-2-yl}-benzamide, hydrochloride salt | 1.1 | 2 | 4.13 | 2 | 3.45 | 2 |
| 1D-07 | 5-methyl-6-(2-methyl-4-{[(3-methylbutyl)-amino]-methyl}phenyl)-nicotinamide, hydrochloride salt | 1.43 | 2 | 8.99 | 2 | 9.3 | 2 |
| E2-01 | 2,2'-dimethyl-4'-{[(3-methylbutyl)-amino]-methyl}biphenyl-4-carboxamide, hydrochloride salt | 0.886 | 6 | 2.06 | 6 | 1.38 | 6 |
| E3-01 | 3'-chloro-2-methyl-4'-{[(3-methylbutyl)-amino]methyl}biphenyl-4-carboxamide, hydrochloride salt | 2.82 | 7 | 1.73 | 7 | 1.53 | 7 |
| E4-01 | 2-Methyl-4'-[(3-methyl-butylamino)-methyl]-biphenyl-4-carboxylic acid amide | 6.5 | 5 | 2.4 | 5 | 20 | 5 |
| E4-02 | 2-methyl-4'-{[(3-methylbutyl)amino]-methyl}biphenyl-4-carboxamide, hydrochloride salt | 6.2 | 5 | 2.16 | 5 | 7.91 | 4 |
| 4A-01 | 4'-{[(3-methylbutyl)-amino]-methyl}-biphenyl-3-carboxamide, hydrochloride salt | 32.8 | 4 | 26.9 | 3 | 15.7 | 1 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 4A-02 | 4-fluoro-4'-{[(3-methylbutyl)amino]-methyl}biphenyl-3-carboxamide, hydrochloride salt | 44800 | 2 | 724 | 4 | 1.55 | 2 |
| 4A-03 | 4'-[(2,3-dihydro-1H-inden-2-ylamino)-methyl]-4-fluorobiphenyl-3-carboxamide, hydrochloride salt | 25.2 | 2 | 60.2 | 4 | 51.9 | 2 |
| 4A-04 | 5-fluoro-4'-{[(3-methylbutyl)amino]-methyl}biphenyl-3-carboxamide, hydrochloride salt | 92.1 | 2 | 60.1 | 4 | 21.4 | 2 |
| 4A-05 | 2'-chloro-4'-{[(3-methylbutyl)amino]-methyl}biphenyl-3-carboxamide, hydrochloride salt | 0.95 | 4 | 9.84 | 4 | ND | — |
| 4A-06 | 2'-chloro-4'-{[(tetrahydro-2H-pyran-3-ylmethyl)-amino]-methyl}-biphenyl-3-carboxamide | 12.5 | 2 | 14.7 | 2 | 23.6 | 2 |
| 4A-07 | 2'-chloro-4'-({[(2S)-tetrahydrofuran-2-yl-methyl]amino}-methyl)biphenyl-3-carboxamide, hydrochloride salt | 9.03 | 2 | 14.7 | 2 | 24.3 | 2 |
| 4A-08 | 2'-chloro-4'-({[2-(tetrahydro-2H-pyran-4-yl)ethyl]-amino}methyl)-biphenyl-3-carboxamide, hydrochloride salt | 3.44 | 2 | 12.9 | 2 | 2.79 | 2 |
| 4A-09 | 2'-chloro-4'-{[(2-isopropoxyethyl)-amino]methyl}-biphenyl-3-carboxamide, hydrochloride salt | 11.1 | 2 | 41.2 | 2 | 5.23 | 2 |
| 4A-10 | 2'-chloro-4'-({[(2,2-dimethyl-13-dioxolan-4-yl)-methyl]amino}-methyl)biphenyl-3-carboxamide | 8.49 | 2 | 31.3 | 2 | 353 | 2 |
| 4A-11 | 2'-chloro-4'-[(2,3-dihydro-1H-inden-1-ylamino)methyl]-biphenyl-3-carboxamide | 6.27 | 1 | 7.69 | 1 | 21.3 | 1 |
| 4A-12 | 2'-chloro-4'-{[(tetrahydro-2H-pyran-2-ylmethyl)amino]-methyl}biphenyl-3-carboxamide | 15 | 2 | 18.2 | 2 | 22.7 | 2 |
| 4A-13 | 2'-chloro-4'-({[2-(tetrahydro-2H-pyran-2-yl)ethyl]-amino}methyl)-biphenyl-3-carboxamide | 1.16 | 2 | 11 | 2 | 3.27 | 2 |
| 4B-01 | 4'-{[(3-methylbutyl)-amino]-methyl}-biphenyl-4-carboxamide, hydrochloride salt | 175 | 2 | 88.6 | 2 | 14 | 1 |
| 4B-02 | 4'-{[(3-methylbutyl)-amino]-methyl}-2-(trifluoromethyl)-biphenyl-4-carboxamide, hydrochloride salt | 57.2 | 2 | 29.7 | 2 | 15.4 | 2 |
| 4B-03 | 4'-[(benzylamino)-methyl]-2-methylbiphenyl-4-carboxamide, hydrochloride salt | 3.13 | 3 | 1.84 | 3 | 4 | 3 |
| 4B-04 | 4'-[(2,3-dihydro-1H-inden-2-yl-amino)methyl]-2-methylbiphenyl-4- | 0.0925 | 5 | 0.406 | 5 | 0.185 | 5 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 4B-05 | carboxamide, hydrochloride salt<br>2-methyl-4'-({[2-(tetrahydro-2H-pyran-4-yl)-ethyl]amino}methyl)-biphenyl-4-carboxamide, hydrochloride salt | 4.07 | 2 | 3.39 | 2 | 0.893 | 2 |
| 4B-06 | 4'-{[(2-isopropoxyethyl)-amino]methyl}-2-methylbiphenyl-4-carboxamide, hydrochloride salt | 10.3 | 3 | 8.53 | 3 | 6.42 | 3 |
| 4B-07 | 4'-({[(2R)-2-ethoxybutyl]amino-methyl)-2-methylbiphenyl-4-carboxamide, hydrochloride salt | 33.8 | 2 | 15.5 | 2 | 35.9 | 2 |
| 4B-08 | 2-methyl-4'-{[(3-phenylpropyl)-amino]-methyl}-biphenyl-4-carboxamide, hydrochloride salt | 2.84 | 2 | 2.19 | 2 | 0.838 | 2 |
| 4B-09 | 2-methyl-4'-{[(2-phenylethyl)amino]-methyl}biphenyl-4-carboxamide, hydrochloride salt | 2.73 | 2 | 6.19 | 2 | 1.82 | 2 |
| 4B-10 | 4'-{[(3-chlorobenzyl)-amino]-methyl}-2-methylbiphenyl-4-carboxamide | 0.94 | 2 | 1.58 | 2 | 0.602 | 2 |
| 4B-11 | 4'-{[(2-cyclopropylethyl)-amino]methyl}-2-methylbiphenyl-4-carboxamide, hydrochloride salt | 8.38 | 1 | 5.7 | 1 | 7.05 | 1 |
| 4B-12 | 2,6-difluoro-4'-{[(3-methylbutyl)amino]-methyl}biphenyl-4-carboxamide, hydrochloride salt | 48.4 | 2 | 26.8 | 2 | 16.9 | 2 |
| 4B-13 | 4'-(1,3-dihydro-2H-isoindol-2-yl-methyl)-2-methyl-biphenyl-4-carboxamide | 207 | 3 | 33 | 5 | 159 | 3 |
| 4B-14 | 2,6-dimethyl-4'-{[(3-methylbutyl)amino]-methyl}biphenyl-4-carboxamide, hydrochloride salt | 86.5 | 4 | 29.6 | 4 | 6.27 | 4 |
| 4B-15 | 3-fluoro-4'-{[(3-methylbutyl)amino]-methyl}biphenyl-4-carboxamide, hydrochloride salt | 295 | 2 | 278 | 4 | 355 | 2 |
| 4B-16 | 2-methyl-4'-{[(2-phenoxyethyl)-amino]-methyl}-biphenyl-4-carboxamide, hydrochloride salt | 2.82 | 2 | 7.65 | 2 | 0.751 | 2 |
| 4B-17 | 4'-{[(3-fluorobenzyl)-amino]-methyl}-2-methylbiphenyl-4-carboxamide, hydrochloride salt | 2.56 | 2 | 1.21 | 2 | 1.13 | 2 |
| 4B-18 | 4'-({[(2,2-dimethyl-2,3-dihydro-1-benzofuran-5-yl)-methyl]amino}-methyl)-2-methyl-biphenyl-4-carboxamide, hydrochloride salt | 5.72 | 2 | 18.7 | 2 | 2.46 | 2 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 4B-19 | 2-methyl-4'-{[(1-methyl-1-phenylethyl)amino]-methyl}biphenyl-4-carboxamide, hydrochloride salt | 126 | 2 | 23.4 | 2 | 19.5 | 2 |
| 4B-20 | 4'-{[(2,3-dihydro-1-benzofuran-5-ylmethyl)amino]-methyl}-2-methylbiphenyl-4-carboxamide, hydrochloride salt | 7.1 | 2 | 34.5 | 2 | 4.21 | 2 |
| 4B-21 | 4'-[(2,3-dihydro-1H-inden-1-yl-amino)methyl]-2-methylbiphenyl-4-carboxamide, hydrochloride salt | 1.5 | 2 | 0.872 | 2 | 1.25 | 2 |
| 4B-22 | 2-methyl-4'-{[(8-methyl-3,4-dihydro-2H-chromen-4-yl)-amino]-methyl}-biphenyl-4-carboxamide, hydrochloride salt | 7.56 | 2 | 4.92 | 2 | 5.1 | 2 |
| 4B-23 | 4'-({[1-(3-chlorophenyl)-cyclopropyl]amino}-methyl)-2-methylbiphenyl-4-carboxamide, hydrochloride salt | 266 | 2 | 14.2 | 2 | 46.3 | 2 |
| 4B-24 | 2-methyl-4'-{[(1-phenylcyclopropyl)-amino]methyl}-biphenyl-4-carboxamide, hydrochloride salt | 1290 | 2 | 400 | 2 | 22.7 | 2 |
| 4B-25 | 4'-({[1-(3-chlorophenyl)-1-methylethyl]-amino}methyl)-2-methylbiphenyl-4-carboxamide, hydrochloride salt | 37.6 | 2 | 6.11 | 2 | 22.6 | 2 |
| 4B-26 | 4'-{[(2-fluorobenzyl)-amino]methyl}-2-methylbiphenyl-4-carboxamide, hydrochloride salt | 4.55 | 2 | 3.32 | 2 | 5.72 | 2 |
| 4B-27 | 2-methyl-4'-({[1-(2-naphthyl)ethyl]-amino}-methyl)-biphenyl-4-carboxamide, hydrochloride salt | 14.3 | 2 | 2.86 | 2 | 2.98 | 2 |
| 4B-28 | 2-methyl-4'-{[(1R)-1,2,3,4-tetrahydronaphthalen-1-ylamino]-methyl}biphenyl-4-carboxamide, hydrochloride salt | 26.1 | 2 | 4.12 | 2 | 26.3 | 2 |
| 4B-29 | 2-chloro-4'-{[(3-methylbutyl)amino]-methyl}biphenyl-4-carboxamide, hydrochloride salt | 16.2 | 2 | 6.1 | 2 | 6.12 | 2 |
| 4B-30 | 2-chloro-4'-[(2,3-dihydro-1H-inden-2-ylamino)-methyl]biphenyl-4-carboxamide, hydrochloride salt | 0.41 | 2 | 0.842 | 2 | 0.378 | 2 |
| 4B-31 | 4'-{[(2,3-dihydro-1-benzofuran-2-yl-methyl)amino]-methyl}-2-methylbiphenyl-4-carboxamide, hydrochloride salt | 4.05 | 2 | 3.71 | 2 | 1.09 | 2 |
| 4B-32 | 4'-[(2,3-dihydro-1H-inden-2-ylamino)-methyl]-2,6-dimethylbiphenyl-4-carboxamide, hydrochloride salt | 0.0492 | 3 | 0.14 | 3 | 0.0696 | 3 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 4B-33 | 4'-{[(1R)-2,3-dihydro-1H-inden-1-ylamino]-methyl}-2-methylbiphenyl-4-carboxamide, hydrochloride salt | 4.95 | 3 | 0.911 | 3 | 2.49 | 3 |
| 4B-34 | 4'-{[(1S)-2,3-dihydro-1H-inden-1-ylamino]methyl}-2-methylbiphenyl-4-carboxamide, hydrochloride salt | 1.08 | 4 | 0.512 | 4 | 1.09 | 4 |
| 4B-35 | 4'-{[(2,3-dihydro-1H-inden-2-yl-methyl)-amino]methyl}-2-methylbiphenyl-4-carboxamide, hydrochloride salt | 1.32 | 3 | 7.13 | 3 | 0.687 | 3 |
| 4B-36 | 4'-{[(3,4-dihydro-2H-chromen-2-ylmethyl)amino]-methyl}-2-methylbiphenyl-4-carboxamide, hydrochloride salt | 1.45 | 3 | 6.5 | 3 | 0.453 | 3 |
| 4B-37 | 2-chloro-4'-({[2-(tetrahydro-2H-pyran-4-yl)-ethyl]amino}methyl)biphenyl-4-carboxamide, hydrochloride salt | 13.7 | 3 | 4.61 | 3 | 60.3 | 3 |
| 4B-38 | 2-chloro-4'-{[(1S)-2,3-dihydro-1H-inden-1-yl-amino]methyl}-biphenyl-4-carboxamide, hydrochloride salt | 3.33 | 2 | 1.14 | 2 | 5.59 | 2 |
| 4B-39 | 2-chloro-4'-{[(2-cyclopentylethyl)-amino]methyl}biphenyl-4-carboxamide, hydrochloride salt | 1.87 | 2 | 1.28 | 2 | 0.612 | 2 |
| 4B-40 | 2-methyl-4'-{[(tetrahydro-2H-pyran-4-yl-methyl)amino]-methyl}biphenyl-4-carboxamide, hydrochloride salt | 48.3 | 3 | 9.05 | 3 | 20.4 | 3 |
| 4B-41 | 2-methyl-4'-({[(1R)-1-phenylethyl]-amino}-methyl)-biphenyl-4-carboxamide, hydrochloride salt | 61.4 | 2 | 13.5 | 2 | 14.1 | 2 |
| 4B-42 | 2-methyl-4'-({[(1S)-1-phenylethyl]-amino}-methyl)-biphenyl-4-carboxamide, hydrochloride salt | 65.4 | 2 | 6.19 | 2 | 22.2 | 2 |
| 4B-43 | 2-methyl-4'-{[(pyridin-3-yl-methyl)amino]-methyl}biphenyl-4-carboxamide, hydrochloride salt | 70.2 | 2 | 8.95 | 2 | 10.6 | 2 |
| 4B-44 | 2-methyl-4'-{[(pyridin-2-yl-methyl)amino]-methyl}biphenyl-4-carboxamide, hydrochloride salt | 61.7 | 2 | 25.7 | 2 | 26.1 | 2 |
| 4B-45 | 2-(benzyloxy)-4'-{[(3-methylbutyl)-amino]-methyl}-biphenyl-4-carboxamide, hydrochloride salt | 40.2 | 2 | 9.84 | 2 | 44.6 | 2 |
| 4B-46 | 2-methoxy-4'-{[(3-methylbutyl)amino]-methyl}biphenyl-4-carboxamide, hydrochloride salt | 121 | 1 | 14.7 | 1 | 10000 | 1 |

-continued

| Ex. No. | Name | Mu functional (nM) | Mu N* | Kappa functional (nM) | Kappa N* | Delta functional (nM) | Delta N* |
|---|---|---|---|---|---|---|---|
| 4B-47 | 2-hydroxy-4'-{[(3-methylbutyl)amino]-methyl}biphenyl-4-carboxamide, hydrochloride salt | 549 | 1 | 80.6 | 1 | 543 | 1 |
| 4B-48 | 2-ethyl-4'-{[(3-methylbutyl)amino]-methyl}biphenyl-4-carboxamide, hydrochloride salt | 12 | 2 | 13.9 | 2 | 16.1 | 2 |
| 4B-49 | 2-chloro-6-methyl-4'-{[(3-methylbutyl)-amino]-methyl}-biphenyl-4-carboxamide, hydrochloride salt | 2.72 | 2 | 2.31 | 2 | 6.66 | 2 |
| 4B-50 | 3',5'-difluoro-2-methyl-4'-({[2-(tetrahydro-2H-pyran-4-yl)ethyl]-amino-}methyl)-biphenyl-4-carboxamide | 1.45 | 3 | 0.948 | 3 | 0.135 | 3 |
| 4B-51 | 3',5'-difluoro-2-methyl-4'-({[2-(tetrahydro-2H-pyran-4-yl)-ethyl]amino}-methyl)biphenyl-4-carboxamide, hydrochloride salt | 2.16 | 3 | 1.95 | 3 | 0.707 | 3 |
| 4B-52 | 3',5'-difluoro-2-methyl-4'-({[(1R)-1-pyridin-2-ylpropyl]-amino}methyl)-biphenyl-4-carboxamide | 138 | 3 | 7.01 | 3 | 15.4 | 3 |
| 4B-53 | 3',5'-difluoro-2-methyl-4'-({[(1R)-1-pyridin-2-ylethyl]-amino}methyl)-biphenyl-4-carboxamide | 92.7 | 3 | 43.1 | 3 | 3.74 | 3 |
| 4B-54 | 4'-[(cyclopentyl-amino)-methyl]-3',5'-difluoro-2-methylbiphenyl-4-carboxamide | 37 | 1 | 15.4 | 1 | 14.5 | 1 |
| 4B-55 | 3',5'-difluoro-2-methyl-4'-({[(2S)-tetrahydrofuran-2-ylmethyl]-amino}-methyl)-biphenyl-4-carboxamide | 30.7 | 3 | 8.55 | 3 | 19 | 3 |
| 4B-56 | 3'-fluoro-2-methyl-4'-{[(tetrahydro-2H-pyran-4-ylmethyl)-amino]-methyl}-biphenyl-4-carboxamide, hydrochloride salt | 36.8 | 2 | 9.04 | 2 | 8.44 | 2 |
| 4B-57 | 2-chloro-3',5'-difluoro-4'-({[2-(tetrahydro-2H-pyran-4-yl)ethyl]-amino}-methyl)-biphenyl-4-carboxamide, hydrochloride salt | 12.7 | 2 | 4.58 | 2 | 168 | 2 |
| 4B-58 | 2-chloro-3'-fluoro-4'-({[2-(tetrahydro-2H-pyran-4-yl)ethyl]-amino}methyl)-biphenyl-4-carboxamide, hydrochloride salt | 7.3 | 2 | 1.77 | 2 | 4.02 | 2 |
| 4B-59 | 3',5'-difluoro-2-methyl-4'-{[(tetrahydro-2H-pyran-4-ylmethyl)-amino]-methyl}-biphenyl-4-carboxamide, hydrochloride salt | 33.3 | 2 | 9.47 | 2 | 19.1 | 2 |
| 4B-60 | 3'-fluoro-2-methyl-4'-({[2-(tetrahydro-2H-pyran-4-yl)-ethyl]-amino}-methyl)-biphenyl-4-carboxamide, hydrochloride salt | 3.9 | 2 | 1.49 | 2 | 1.43 | 2 |
| 4B-61 | 2-chloro-2'-fluoro-4'-{[(3-methylbutyl)-amino]-methyl}-biphenyl-4-carboxamide, hydrochloride salt | 25.6 | 2 | 4.92 | 2 | 12.6 | 2 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 4B-62 | 2-chloro-2'-methyl-4'-{[(3-methylbutyl)-amino]-methyl}-biphenyl-4-carboxamide, hydrochloride salt | 6.4 | 2 | 2.56 | 2 | 3.58 | 2 |
| 4B-63 | 2-chloro-4'-[(2,3-dihydro-1H-inden-2-ylamino)methyl]-3'-fluorobiphenyl-4-carboxamide, hydrochloride salt | 0.226 | 2 | 0.633 | 2 | 0.629 | 2 |
| 4B-64 | 2-chloro-3'-fluoro-4'-{[(3-methylbutyl)-amino]-methyl}-biphenyl-4-carboxamide, hydrochloride salt | 12.1 | 2 | 3.97 | 2 | 5.64 | 2 |
| 4B-65 | 2,3'-dichloro-4'-{[(3-methylbutyl)amino]-methyl}biphenyl-4-carboxamide, hydrochloride salt | 10.8 | 2 | 2.15 | 2 | 4.79 | 2 |
| 4B-66 | 2,2'-dichloro-4'-{[(3-methylbutyl)amino]-methyl}biphenyl-4-carboxamide, hydrochloride salt | 7.83 | 2 | 2.52 | 2 | 7.52 | 2 |
| 4B-67 | 2,2'-dichloro-4'-({[2-(tetrahydro-2H-pyran-4-yl)ethyl]-amino}-methyl)-biphenyl-4-carboxamide, hydrochloride salt | 7.22 | 2 | 3.62 | 2 | 2.95 | 2 |
| 4B-68 | 2,2'-dichloro-4'-[(23-dihydro-1H-inden-2-ylamino)-methyl]biphenyl-4-carboxamide, hydrochloride salt | 0.24 | 2 | 0.759 | 2 | 0.724 | 2 |
| 4B-69 | 2,2'-dichloro-4'-({[2-(tetrahydro-2H-pyran-2-yl)ethyl]-amino}methyl)-biphenyl-4-carboxamide, hydrochloride salt | 2.78 | 2 | 4.54 | 2 | 4.09 | 2 |
| 4B-70 | 2,2'-dimethyl-4'-({[2-(tetrahydro-2H-pyran-4-yl)ethyl]-amino}methyl)-biphenyl-4-carboxamide, hydrochloride salt | 2 | 2 | 2.48 | 2 | 1.04 | 2 |
| 4B-71 | 2,2'-dimethyl-4'-{[(tetrahydro-2H-pyran-4-ylmethyl)-amino]methyl}-biphenyl-4-carboxamide, hydrochloride salt | 8.37 | 2 | 6.91 | 2 | 6.2 | 2 |
| 4B-72 | 2,2'-dimethyl-4'-{[(tetrahydrofuran-2-ylmethyl)-amino]methyl}-biphenyl-4-carboxamide, hydrochloride salt | 9.83 | 2 | 5.44 | 2 | 13 | 2 |
| 4B-73 | 4'-[(2,3-dihydro-1H-inden-2-ylamino)-methyl]-2,2'-dimethylbiphenyl-4-carboxamide, hydrochloride salt | 0.0298 | 2 | 0.318 | 2 | 0.135 | 2 |
| 4B-74 | 2',5'-difluoro-2-methyl-4'-{[(3-methylbutyl)-amino]methyl} biphenyl-4-carboxamide, hydrochloride salt | 4.37 | 2 | 4.45 | 2 | 4.8 | 2 |
| 4B-75 | 4'-[(2,3-dihydro-1H-inden-2-ylamino) methyl]-2'5'-difluoro-2-methyl biphenyl-4-carboxamide, hydrochloride salt | 0.069 | 2 | 1.27 | 2 | 0.309 | 2 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 4B-76 | 2-ethyl-2',6'-dimethyl-4'-({[2-(tetrahydro-2H-pyran-4-yl)ethyl]amino}methyl)-biphenyl-4-carboxamide, hydrochloride salt | 1.02 | 2 | 8.11 | 2 | 0.501 | 2 |
| 4B-77 | 4'-[(2,3-dihydro-1H-inden-2-ylamino)methyl]-2-ethyl-2'-methylbiphenyl-4-carboxamide, hydrochloride salt | 0.114 | 2 | 0.949 | 2 | 0.271 | 2 |
| 4B-78 | 2,2'-dichloro-4'-({[(2R)-tetrahydrofuran-2-ylmethyl]amino}methyl)biphenyl-4-carboxamide, hydrochloride salt | 35.1 | 2 | 8.48 | 2 | 18.8 | 2 |
| 4B-79 | 2,2'-dichloro-4'-({[(2,2-dimethyl-13-dioxolan-4-yl)methyl]amino}methyl)biphenyl-4-carboxamide, hydrochloride salt | 228 | 1 | 128 | 1 | 1.42 | 1 |
| 4B-80 | 2-chloro-2',5'-difluoro-4'-{[(3-methylbutyl)-amino]methyl}biphenyl-4-carboxamide, hydrochloride salt | 13.7 | 2 | 9.5 | 2 | 11.8 | 2 |
| 4B-81 | 2-ethyl-3',5'-difluoro-4'-{[(3-methylbutyl)-amino]methyl}biphenyl-4-carboxamide, hydrochloride salt | 13.4 | 2 | 16.8 | 2 | 15.2 | 2 |
| 4B-82 | 2,2'-dichloro-4'-[(2,3-dihydro-1H-inden-2-yl amino)methyl]-6'-methylbiphenyl-4-carboxamide, hydrochloride salt | 0.0287 | 2 | 1.77 | 2 | 0.15 | 2 |
| 4B-83 | 2'-chloro-2,6'-dimethyl-4'-{[(3-methylbutyl)-amino]methyl}biphenyl-4-carboxamide, hydrochloride salt | 0.429 | 2 | 3.71 | 2 | 1.66 | 2 |
| 4B-84 | 2'-chloro-4'-[(2,3-dihydro-1H-inden-2-ylamino)methyl]-2,6'-dimethyl biphenyl-4-carboxamide, hydrochloride salt | 0.0145 | 2 | 0.593 | 2 | 0.0778 | 2 |
| 4B-85 | 3'-(benzyloxy)-2-methyl-4'-{[(3-methylbutyl)-amino]methyl}biphenyl-4-carboxamide, hydrochloride salt | 2.48 | 2 | 5.48 | 2 | 0.588 | 2 |
| 4B-86 | 3'-(benzyloxy)-4'-[(2,3-dihydro-1H-inden-2-yl-amino)methyl]-2-methylbiphenyl-4-carboxamide, hydrochloride salt | 0.0895 | 2 | 1.74 | 2 | 0.0438 | 2 |
| 4B-87 | 3'-hydroxy-2-methyl-4'-{[(3-methylbutyl-amino]methyl}biphenyl-4-carboxamide, hydrochloride salt | 13.5 | 2 | 7.91 | 2 | 8.53 | 2 |
| 4B-88 | 4'-[(2,3-dihydro-1H-inden-2-yl-amino)methyl]-3'-hydroxy-2-methylbiphenyl-4-carboxamide, hydrochloride salt | 0.134 | 2 | 0.78 | 2 | 0.591 | 2 |

-continued

| Ex. No. | Name | Mu functional (nM) | Mu N* | Kappa functional (nM) | Kappa N* | Delta functional (nM) | Delta N* |
|---|---|---|---|---|---|---|---|
| 4B-89 | 4'-[(2,3-dihydro-1H-inden-2-yl-amino)methyl]-3'-methoxy-2-methylbiphenyl-4-carboxamide, hydrochloride salt | 0.0272 | 2 | 0.366 | 2 | 0.0895 | 2 |
| 4B-90 | 2,3'-dimethyl-4'-{[(3-methylbutyl)amino]-methyl}biphenyl-4-carboxamide, hydrochloride salt | 1.17 | 1 | 1.66 | 1 | 1.66 | 1 |
| 4B-91 | 2'-chloro-2,6'-dimethyl-4'-({[(2R)-tetrahydrofuran-2-ylmethyl]amino-}-methyl)biphenyl-4-carboxamide, hydrochloride salt | 2.22 | 1 | 9.01 | 1 | 24.5 | 1 |
| 4C-01 | 5-chloro-6-(4-{[(3-methylbutyl)amino]-methyl}phenyl)-nicotinamide, hydrochloride salt | 28 | 3 | 15.6 | 3 | 33.8 | 3 |
| 4C-02 | 5-chloro-6-{4-[(2,3-dihydro-1H-inden-2-yl-amino)-methyl]phenyl}-nicotinamide, hydrochloride salt | 0.489 | 3 | 1.95 | 3 | 1.95 | 3 |
| 4C-03 | 6-{4-[(2,3-dihydro-1H-inden-2-yl-amino)-methyl]-phenyl}-5-methyl-nicotinamide, hydrochloride salt | 0.201 | 2 | 0.982 | 2 | 0.822 | 2 |
| 4C-04 | 5-methyl-6-(4-{[(3-methylbutyl)amino]-methyl}phenyl)-nicotinamide, hydrochloride salt | 10.5 | 3 | 7.23 | 3 | 21.9 | 3 |
| E5-01 | 2'-fluoro-4'-[(3-methyl-butylamino)-methyl]-biphenyl-3-carboxylic acid amide, hydrochloride salt | 14 | 1 | 23 | 1 | 10000 | 1 |
| 6A-01 | 2'-chloro-4'-{[(2-ethoxyethyl)amino]-methyl}biphenyl-3-carboxamide, trifluoroacetic acid salt | 12.8 | 1 | 41.6 | 1 | 25.5 | 1 |
| 6A-02 | 2'-chloro-4'-({[2-(1,3-thiazol-4-yl)-ethyl]-amino}-methyl)-biphenyl-3-carboxamide, trifluoroacetic acid salt | 12.4 | 1 | 473 | 1 | 23.5 | 1 |
| 6A-03 | 2'-chloro-4'-({[(1S,2R)-2-hydroxy-2,3-dihydro-1H-inden-1-yl]amino}-methyl)-biphenyl-3-carboxamide, trifluoroacetic acid salt | 2.94 | 1 | 9.35 | 1 | 35.9 | 1 |
| 6A-04 | 2'-chloro-4'-({[(1,3-dimethyl-2-oxo-2,3-dihydro-1H-benzimidazol-5-yl)-methyl]amino}-methyl)-biphenyl-3-carboxamide, trifluoroacetic acid salt | 15 | 1 | 805 | 1 | 32.3 | 1 |
| 6A-05 | 2'-chloro-4'-({[2-(3,5-dimethyl-1H-pyrazol-1-yl)-1-methylethyl]-amino}methyl)-biphenyl-3-carboxamide, trifluoroacetic acid salt | 5.25 | 1 | 27.2 | 1 | 17.6 | 1 |
| 6A-06 | ethyl 4-{[3'-(aminocarbonyl)-2-chlorobiphenyl-4-yl]methyl}-piperazine-1-carboxylate, trifluoroacetic acid salt | 67.6 | 1 | 85.4 | 1 | 0.627 | 1 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 6A-07 | 2'-chloro-4'-{[(2-methoxyethyl)-amino]-methyl}-biphenyl-3-carboxamide, trifluoroacetic acid salt | 78.4 | 1 | 58.1 | 1 | 0.0652 | 1 |
| 6A-08 | 2'-chloro-4'-({[2-(4-methyl-13-thiazol-5-yl)ethyl]amino}-methyl)-biphenyl-3-carboxamide, trifluoroacetic acid salt | 8.62 | 1 | 32.1 | 1 | 4.92 | 1 |
| E7-01 | [2'-methyl-4'-(4H-[1,2,4]triazol-3-yl)-biphenyl-4-ylmethyl]-(3-methyl-butyl)-amine, hydrochloride salt | 3.9 | 2 | 13 | 2 | 11 | 2 |
| E7-02 | [2-Fluoro-3'-(4H-[1,2,4]triazol-3-yl)-biphenyl-4-ylmethyl]-(3-methyl-butyl)-amine, hydrochloride salt | 3.3 | 3 | 5.9 | 3 | 1400 | 3 |
| 7A-01 | 3-methyl-N-{[3'-(1H-1,2,4-triazol-5-yl)-biphenyl-4-yl]-methyl}-butan-1-amine, hydrochloride salt | 8.31 | 4 | 8.43 | 3 | 26.1 | 1 |
| 7A-02 | N-{[2'-fluoro-2-methyl-5'-(4H-1,2,4-triazol-3-yl)-biphenyl-4-yl]-methyl}-3-methylbutan-1-amine, hydrochloride salt | 1.59 | 2 | 1.77 | 3 | 5.26 | 1 |
| 7A-03 | N-{[2,2'-difluoro-5'-(4H-1,2,4-triazol-3-yl)-biphenyl-4-yl]-methyl}-3-methylbutan-1-amine, hydrochloride salt | 4.07 | 1 | 2.71 | 1 | 12.5 | 1 |
| 7A-04 | [2-Chloro-3'-(4H-[1,2,4]triazol-3-yl)-biphenyl-4-ylmethyl]-(3-methyl-butyl)-amine, hydrochloride salt | 0.162 | 2 | 0.794 | 2 | ND | — |
| 7A-05 | (3-Methyl-butyl)-[2-methyl-3'-(4H-[1,2,4]triazol-3-yl)-biphenyl-4-ylmethyl]-amine, hydrochloride salt | 0.505 | 1 | 2.12 | 1 | ND | — |
| 7A-06 | [2,6-Difluoro-3'-(4H-[1,2,4]triazol-3-yl)-biphenyl-4-ylmethyl]-(3-methyl-butyl)-amine, hydrochloride salt | 2.06 | 3 | 4.61 | 3 | ND | — |
| 7B-01 | 3-methyl-N-{[4'-(1H-1,2,4-triazol-5-yl)-biphenyl-4-yl]methyl}-butan-1-amine, hydrochloride salt | 10.3 | 4 | 35 | 3 | 311 | 1 |
| 7B-02 | 3-methyl-N-{[2-methyl-4'-(4H-1,2,4-triazol-3-yl)-biphenyl-4-yl]methyl}-butan-1-amine, hydrochloride salt | 0.72 | 2 | 4.4 | 2 | 3.71 | 2 |
| 7B-03 | N-{[2-fluoro-2'-methyl-4'-(4H-1,2,4-triazol-3-yl)-biphenyl-4-yl]-methyl}-3-methylbutan-1-amine, hydrochloride salt | 1.7 | 2 | 9.25 | 2 | 28.2 | 2 |
| 7B-04 | N-{[2-fluoro-4'-(4H-1,2,4-triazol-3-yl)-biphenyl-4-yl]-methyl}-3-methylbutan-1-amine, hydrochloride salt | 2.53 | 2 | 13.6 | 2 | 8.08 | 2 |
| 7B-05 | 3-methyl-N-{[4'-(4H-1,2,4-triazol-3-yl)-2'-(trifluoromethyl)-biphenyl-4-yl]-methyl}-butan-1-amine, hydrochloride salt | 14.2 | 2 | 47.4 | 2 | 29.7 | 2 |
| E8-01 | N-(2'-methyl-4'-{[(3-methylbutyl)amino]-methyl}-biphenyl-4-yl)-methane-sulfonamide, hydrochloride salt | 42.1 | 1 | 281 | 1 | 32.6 | 1 |

-continued

| | | GTPγ[35S] binding Ki Values | | | | | |
|---|---|---|---|---|---|---|---|
| Ex. No. | Name | Mu functional (nM) | Mu N* | Kappa functional (nM) | Kappa N* | Delta functional (nM) | Delta N* |
| 8A-01 | N-(4'-{[(3-methylbutyl)amino]-methyl}-biphenyl-3-yl)methane-sulfonamide, hydrochloride salt | 14.6 | 2 | 45.9 | 2 | ND | — |
| 8A-02 | N-(2'-methyl-4'-{[(3-methylbutyl)amino]-methyl}biphenyl-3-yl)methane-sulfonamide, hydrochloride salt | 1.15 | 4 | 15.3 | 4 | 10.4 | 2 |
| 8A-03 | N-(2'-cyano-4'-{[(3-methylbutyl)amino]-methyl}biphenyl-3-yl)methane-sulfonamide | 1.16 | 2 | 13.7 | 3 | 18.4 | 1 |
| 8B-01 | N-(2-methyl-4'-{[(3-methylbutyl)amino]-methyl}biphenyl-4-yl)methane-sulfonamide, hydrochloride salt | 715 | 1 | 1450 | 1 | 10000 | 1 |
| 8B-02 | N-{4'-[(2,3-dihydro-1H-inden-2-yl-amino)-methyl]-3'-fluorobiphenyl-4-yl}-methane-sulfonamide, hydrochloride salt | 9.29 | 2 | 582 | 2 | 39.8 | 2 |

*N = the number of samples tested
ND = not determined

Obesity and Related Disorders

The practice of the instant invention for treating obesity or related eating disorders (including promoting weight loss or reducing weight gain) can be evidenced by activity in one or both of the protocols described hereinbelow. Selected compounds were tested in vivo using one or more of the models described below.

In Vivo Biological Assays

Fasted Induced Refeeding Model

The following screen is used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats are individually housed and fed powdered chow. They are maintained on a 12 hour light/dark cycle and received food and water ad libitum. The animals are acclimated to the vivarium for a period of one week before testing is conducted. Testing is completed during the light portion of the cycle.

To conduct the food intake efficacy screen, rats are transferred to individual test cages without food the afternoon prior to testing, and the rats are fasted overnight. After the overnight fast, rats are dosed the following morning with vehicle or test compounds. A known antagonist is dosed (3 mg/kg) as a positive control, and a control group receives vehicle alone (no compound). The test compounds are dosed at ranges between 0.1 and 100 mg/kg depending upon the compound. The standard vehicle is 0.5% (w/v) methylcellulose in water and the standard route of administration is oral. However, different vehicles and routes of administration are used to accommodate various compounds when required. Food is provided to the rats 30 minutes after dosing and the Oxymax automated food intake system (Columbus Instruments, Columbus, Ohio) is started. Individual rat food intake is recorded continuously at 10-minute intervals for a period of two hours. When required, food intake is recorded manually using an electronic scale; food is weighed every 30 minutes after food is provided up to four hours after food is provided. Compound efficacy is determined by comparing the food intake pattern of compound-treated rats to vehicle and the standard positive control.

The following compounds were tested in the fasted induced refeeding model above: 7A-01, 7B 01, E7-02, 7A-04, 7A-05, and 7A-06. A significant reduction in food intake was observed for each of the compounds.

Alternatively, food intake may be determined using the following spontaneous food intake model.

Spontaneous Food Intake Model

Male Sprague-Dawley rats may be obtained from Charles River Laboratories, Inc. (Wilmington, Mass.). The rats were individually housed and fed powdered chow. They were maintained on a 12 hour light/dark cycle and received food and water ad libitum. The animals were acclimated to the vivarium for a period of one week before testing is conducted. Rats were transferred to individual test cages 30 hours before the study. The rats were administered test compound or vehicle alone (no compound) 15-30 minutes prior to the onset of the dark cycle. The test compounds were dosed at ranges between 0.1 and 100 mg/kg depending upon the compound. The standard vehicle was 0.5% (w/v) methylcellulose or 30% β-cyclodextrin in water and the standard route of administration was oral. However, different vehicles and routes of administration are used to accommodate various compounds when required. Food intake was monitored using an automated Columbus Instruments system (Columbus, Ohio). Individual rat food intake was recorded continuously at 10-minute intervals, starting at the time of dosing, for a period of at least 12 hours. Compound efficacy was determined by comparing the food intake pattern of compound-treated rats to vehicle.

The following compounds were tested in the spontaneous food intake model above: E1-01, 1A-07, 1B-03, E2-01, E3-01, 4B-04, 4B08, E4-01, E7-02. A significant reduction in food intake was observed for each of the compounds.

Oxygen Consumption

Whole body oxygen consumption is measured using an indirect calorimeter (Oxymax from Columbus Instruments, Columbus, Ohio) in male Sprague Dawley rats (if another rat strain or female rats is used, it will be specified). Rats (300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e. s.c., i.p., i.v.). Drugs are prepared in methylcellulose, water or other specified vehicle (examples include PEG400, 30% beta-cyclo dextran and propylene glycol). Oxygen consumption and ambulatory activity are measured every 10 minutes for an additional 1-6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min $O_2$ consumption values, excluding periods of high ambulatory activity (ambulatory activity count>100) and excluding the first 5 values of the pre-dose period and the first value from the post-dose period. Change in oxygen consumption is reported as percent and is calculated by dividing the post-dosing resting oxygen consumption by the pre-dose oxygen consumption*100. Experiments will typically be done with n=46 rats and results reported are mean +/−SEM. An increase in oxygen consumption of >10% is considered a positive result. Historically, vehicle-treated rats have no change in oxygen consumption from pre-dose basal.

The invention claimed is:

1. A compound of Formula (I)

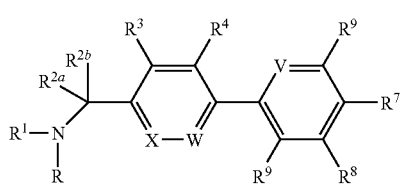

(I)

wherein

R is hydrogen;

$R^1$ is (a) a non-linear $(C_4$-$C_6)$ alkyl, (b) fully saturated $(C_5$-$C_6)$carbocycle fused to a benzene ring, (c) fully saturated 5- to 6-membered heterocycle containing 1 to 2 heteroatoms independently selected from O, S or N fused to a benzene ring, or (d) $(C_1$-$C_3)$alkyl substituted with a chemical moiety selected from the group consisting of
  (i) fully saturated $(C_3$-$C_6)$carbocycle optionally fused to a benzene ring,
  (ii) $(C_1$-$C_4)$alkoxy,
  (iii) fully saturated 5- to 6-membered heterocycle containing 1 to 2 heteroatoms independently selected from O, S or N optionally fused to a benzene ring,
  (iv) 5- to 6-membered heteroaryl containing 1 to 3 heteroatoms independently selected from O, S or N optionally fused to a benzene ring,
  (v) phenyl optionally fused to a 5- to 6-membered heterocycle containing 1 to 2 heteroatoms independently selected from O, S or N,
  (vi) naphthyl, and
  (vii) phenoxy, where said substituents (a) through (d) and said moieties (i) through (vii) are each optionally substituted with one to three substituents independently selected from —OH, chloro, fluoro, or methyl;

$R^{2a}$ and $R^{2b}$ are each hydrogen;

$R^3$ is hydrogen, chloro, fluoro, hydroxyl, or methoxy;

$R^4$ is hydrogen, chloro, fluoro, methyl, or fluoro-substituted methyl;

V is nitrogen or C—$R^5$, where $R^5$ is hydrogen, methyl, ethyl, fluoro-substituted methyl, chloro, fluoro, or methoxy;

$R^6$ is hydrogen or fluoro, $R^7$ is —C(O)NH$_2$;

$R^8$ is hydrogen, fluoro, or —OH;

$R^9$ is hydrogen, $(C_1$-$C_3)$alkyl, fluoro-substituted methyl, chloro, or fluoro; and W is C—$R^{10}$ and X is C—$R^{11}$, where $R^{10}$ is hydrogen, methyl, fluoro-substituted methyl, cyano, chloro, or fluoro, and $R^{11}$ is hydrogen, methyl, methoxy, chloro, or fluoro;

or a pharmaceutically acceptable salt thereof.

2. The compound of claim 1 wherein $R^1$ is a non-linear $(C_4$-$C_6)$ alkyl, a fully saturated $(C_5$-$C_6)$ carbocycle fused to a benzene ring, or a $(C_1$-$C_3)$alkyl substituted with a chemical moiety selected from the group consisting of
  (i) fully saturated $(C_3$-$C_6)$carbocycle optionally fused to a benzene ring,
  (ii) $(C_1$-$C_4)$alkoxy,
  (iii) fully saturated 5- to 6-membered heterocycle containing an oxygen atom optionally fused to a benzene ring,
  (iv) phenyl optionally substituted with chloro or fluoro, and
  (v) phenoxy;

V is C—$R^5$; W is C—$R^{10}$; and X is C—$R^{11}$;

where $R^5$, $R^{10}$ and $R^{11}$ are as defined in claim 1 above;

or a pharmaceutically acceptable salt thereof.

3. The compound of claim 1 selected from the group consisting of 2-chloro-3',5'-difluoro-4'-({[2-(tetrahydro-2H-pyran-4-yl)ethyl]-amino}-methyl)-biphenyl-4-carboxamide;

3',5'-difluoro-2-methyl-4'-({[(2S)-tetrahydrofuran-2-ylmethyl]-amino}-methyl)-biphenyl-4-carboxamide;

3'-fluoro-2-methyl-4'-{[(tetrahydro-2H-pyran-4-ylmethyl)-amino]-methyl}-biphenyl-4-carboxamide;

3',5'-difluoro-2-methyl-4'-{[(tetrahydro-2H-pyran-4-ylmethyl)-amino]-methyl}-biphenyl-4-carboxamide;

2'-chloro-2,6'-dimethyl-4'-({[(2R)-tetrahydrofuran-2-yl-methyl]amino-}-methyl)biphenyl-4-carboxamide;
3',5'-difluoro-2-methyl-4'-({[2-(tetrahydro-2H-pyran-4-yl)-ethyl]amino}-methyl)biphenyl-4-carboxamide;
3'-fluoro-2-methyl-4'-({[2-(tetrahydro-2H-pyran-4-yl)-ethyl]-amino}-methyl)-biphenyl-4-carboxamide;
2,2'-dimethyl-4'-{[(tetrahydrofuran-2-ylmethyl)-amino]methyl}-biphenyl-4-carboxamide;
2,2'-dimethyl-4'-{[(tetrahydro-2H-pyran-4-ylmethyl)-amino]methyl}-biphenyl-4-carboxamide;
2,2'-dimethyl-4'-({[2-(tetrahydro-2H-pyran-4-yl)ethyl]amino}methyl)-biphenyl-4-carboxamide;
2-chloro-3'-fluoro-4'-({[2-(tetrahydro-2H-pyran-4-yl)ethyl]-amino}methyl)-biphenyl-4-carboxamide;
2,2'-dichloro-4'-({[2-(tetrahydro-2H-pyran-4-yl)ethyl]-amino}-methyl)-biphenyl-4-carboxamide;
4'-{[(2-cyclopropylethyl)-amino]methyl}-2-methyl biphenyl-4-carboxamide;
4'-{[(2-fluorobenzyl)-amino]methyl}-2-methylbiphenyl-4-carboxamide;
2-methyl-4'-{[(3-phenylpropyl)-amino]-methyl}-biphenyl-4-carboxamide;
2-methyl-4'-{[(2-phenylethyl)amino]-methyl}biphenyl-4-carboxamide;
4'-{[(3-fluorobenzyl)-amino]-methyl}-2-methylbiphenyl-4-carboxamide;
4'-{[(2,3-dihydro-1-benzofuran-2-yl-methyl)amino]-methyl}-2-methylbiphenyl-4-carboxamide;
2-chloro-4'-{[(2-cyclopentylethyl)-amino]methyl}biphenyl-4-carboxamide;
2-chloro-4'-({[2-(tetrahydro-2H-pyran-4-yl)-ethyl]amino}methyl)biphenyl-4-carboxamide;
4'-{[(2,3-dihydro-1H-inden-2-yl-methyl)-amino]methyl}-2-methylbiphenyl-4-carboxamide;
2-methyl-4'-{[(2-phenoxyethyl)-amino]-methyl}-biphenyl-4-carboxamide;
4'-{[(2-isopropoxyethyl)-amino]methyl}-2-methyl biphenyl-4-carboxamide;
4'-[(benzylamino)-methyl]-2-methylbiphenyl-4-carboxamide;
4'-{[(3-chlorobenzyl)-amino]-methyl}-2-methylbiphenyl-4-carboxamide; and
2-methyl-4'-({[2-(tetrahydro-2H-pyran-4-yl)-ethyl]amino}methyl)-biphenyl-4-carboxamide;
or a pharmaceutically acceptable salt thereof.

4. The compound of claim 2 wherein $R^1$ is a non-linear ($C_4$-$C_6$) alkyl;
or a pharmaceutically acceptable salt thereof.

5. The compound of claim 4 wherein $R^1$ is 3-methylbutyl;
or a pharmaceutically acceptable salt thereof.

6. The compound of claim 5 selected from the group consisting of
2',5'-difluoro-2-methyl-4'-{[(3-methylbutyl)-amino]methyl}biphenyl-4-carboxamide;
3'-hydroxy-2-methyl-4'-{[(3-methylbutyl-amino]methyl}biphenyl-4-carboxamide;
2-chloro-2'-methyl-4'-{[(3-methylbutyl)-amino]-methyl}-biphenyl-4-carboxamide;
2'-chloro-2,6'-dimethyl-4'-{[(3-methylbutyl)-amino]methyl}biphenyl-4-carboxamide;
2-chloro-3'-fluoro-4'-{[(3-methylbutyl)-amino]-methyl}-biphenyl-4-carboxamide;
2,3'-dimethyl-4'-{[(3-methylbutyl)amino]-methyl}biphenyl-4-carboxamide;
3'-fluoro-2-methyl-4'-{[(3-methyl butyl)-amino]-methyl}-biphenyl-4-carboxamide;
2-chloro-4'-{[(3-methylbutyl)amino]-methyl}biphenyl-4-carboxamide;
2-ethyl-4'-{[(3-methylbutyl)amino]-methyl}biphenyl-4-carboxamide; and
2-chloro-6-methyl-4'-{[(3-methylbutyl)-amino]-methyl}-biphenyl-4-carboxamide;
or a pharmaceutically acceptable salt thereof.

7. The compound of claim 2 selected from the group consisting of
3',5'-difluoro-2-methyl-4'-[(3-methyl-butylamino)-methyl]-biphenyl-4-carboxylic acid amide;
2,2'-dimethyl-4'-[(3-methyl-butylamino)-methyl]-biphenyl-4-carboxylic acid amide; and
3'-chloro-2-methyl-4'-[(3-methyl-butylamino)-methyl]-biphenyl-4-carboxylic acid amide hydrochloride;
or a pharmaceutically acceptable salt thereof.

8. The compound of claim 7 which is 3',5'-difluoro-2-methyl-4'-[(3-methyl-butylamino)-methyl]-biphenyl-4-carboxylic acid amide;
or a hydrochloride salt thereof.

9. A compound which is 3',5'-difluoro-2-methyl-4'-[(3-methyl-butylamino)-methyl]-biphenyl-4-carboxylic acid amide hydrochloride monohydrate.

10. The compound of claim 2 wherein $R^1$ is a fully saturated ($C_5$-$C_6$)carbocycle fused to a benzene ring;
or a pharmaceutically acceptable salt thereof.

11. The compound of claim 10 selected from the group consisting of
2'-chloro-4'-[(2,3-dihydro-1H-inden-2-ylamino)methyl]-2,6'-dimethyl-biphenyl-4-carboxamide;
4'-[(2,3-dihydro-1H-inden-2-ylamino)methyl]-2-ethyl-2'-methylbiphenyl-4-carboxamide;
2,2'-dichloro-4'-[(2,3-dihydro-1H-inden-2-ylamino)-methyl]biphenyl-4-carboxamide;
4'-[(2,3-dihydro-1H-inden-2-ylamino)-methyl]-3',5'-difluoro-2-methyl-biphenyl-4-carboxamide;
4'-[(2,3-dihydro-1H-inden-2-ylamino)-methyl]-3'-fluoro-2-methylbiphenyl-4-carboxamide;
4'-[(2,3-dihydro-1H-inden-2-yl-amino)methyl]-3'-methoxy-2-methylbiphenyl-4-carboxamide;
4'-[(2,3-dihydro-1H-inden-2-yl-amino)methyl]-3'-hydroxy-2-methylbiphenyl-4-carboxamide;
4'-[(2,3-dihydro-1H-inden-2-ylamino)-methyl]-2'-fluoro-2-methylbiphenyl-4-carboxamide;
4'-[(2,3-dihydro-1H-inden-2-ylamino)-methyl]-2,2'-dimethylbiphenyl-4-carboxamide;
2-chloro-4'-[(2,3-dihydro-1H-inden-2-ylamino)methyl]-3'-fluorobiphenyl-4-carboxamide;
4'-[(2,3-dihydro-1H-inden-2-ylamino)methyl]-2'5'-difluoro-2-methyl-biphenyl-4-carboxamide;
2-chloro-4'-[(2,3-dihydro-1H-inden-2-ylamino)-methyl]biphenyl-4-carboxamide;
4'-{[(1R)-2,3-dihydro-1H-inden-1-ylamino]-methyl}-2-methylbiphenyl-4-carboxamide;
2-chloro-4'-{[(1S)-2,3-dihydro-1H-inden-1-yl-amino]methyl}-biphenyl-4-carboxamide;
4'-[(2,3-dihydro-1H-inden-2-yl-amino)methyl]-2-methylbiphenyl-4-carboxamide;
4'-[(2,3-dihydro-1H-inden-2-ylamino)-methyl]-2,6-dimethylbiphenyl-4-carboxamide;
4'-{[(1S)-2,3-dihydro-1H-inden-1-ylamino]methyl}-2-methylbiphenyl-4-carboxamide; and
4'-[(2,3-dihydro-1H-inden-1-yl-amino)methyl]-2-methylbiphenyl-4-carboxamide;
or a pharmaceutically acceptable salt thereof.

12. The compound of claim 1 wherein
$R^1$ is a non-linear $(C_4$-$C_6)$ alkyl, a fully saturated $(C_5$-$C_6)$ carbocycle fused to a benzene ring, or a $(C_1$-$C_3)$alkyl substituted with a chemical moiety selected from the group consisting of
  (i) fully saturated $(C_3$-$C_6)$carbocycle optionally fused to a benzene ring,
  (ii) $(C_1$-$C_4)$alkoxy,
  (iii) fully saturated 5- to 6-membered heterocycle containing an oxygen atom optionally fused to a benzene ring,
  (iv) phenyl optionally substituted with a chloro or fluoro, and
  (v) phenoxy;
V is N; W is C—$R^{10}$; and X is C—$R^{11}$;
where $R^{10}$ and $R^{11}$ are as defined in claim 1 above;
or a pharmaceutically acceptable salt thereof.

13. The compound of claim 12 selected from the group consisting of
  5-methyl-6-(4-{[(3-methylbutyl)amino]-methyl}phenyl)-nicotinamide;
  6-{4-[(2,3-dihydro-1H-inden-2-yl-amino)-methyl]-phenyl}-5-methyl-nicotinamide; and
  5-chloro-6-{4-[(2,3-dihydro-1H-inden-2-yl-amino)-methyl]phenyl}-nicotinamide;
or a pharmaceutically acceptable salt thereof.

14. A pharmaceutical composition comprising
  (a) a compound of claim 1; and
  (b) a pharmaceutically acceptable excipient, diluent, or carrier.

15. The composition of claim 14 wherein said compound is 3',5'-difluoro-2-methyl-4'-[(3-methyl-butylamino)-methyl]-biphenyl-4-carboxylic acid amide or a hydrochloride salt thereof.

* * * * *